US009765073B2

(12) United States Patent
Pettersson et al.

(10) Patent No.: US 9,765,073 B2
(45) Date of Patent: Sep. 19, 2017

(54) CYCLOPROPABENZOFURANYL PYRIDOPYRAZINEDIONES

(71) Applicant: Pfizer Inc., New York, NY (US)

(72) Inventors: Martin Youngjin Pettersson, Littleton, MA (US); Christopher William am Ende, Mystic, CT (US); Douglas Scott Johnson, Concord, MA (US); Gregory Wayne Kauffman, East Greenwich, RI (US); Antonia Friederike Stepan, Brookline, MA (US); Patrick Robert Verhoest, Newton, MA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 15/382,778

(22) Filed: Dec. 19, 2016

(65) Prior Publication Data

US 2017/0096428 A1    Apr. 6, 2017

Related U.S. Application Data

(63) Continuation of application No. 15/012,954, filed on Feb. 2, 2016, now abandoned.

(60) Provisional application No. 62/111,222, filed on Feb. 3, 2015.

(51) Int. Cl.
*C07D 471/04*   (2006.01)
*A61K 31/4985*   (2006.01)

(52) U.S. Cl.
CPC ........ *C07D 471/04* (2013.01); *A61K 31/4985* (2013.01)

(58) Field of Classification Search
None
See application file for complete search history.

(56) References Cited

U.S. PATENT DOCUMENTS

| | | |
|---|---|---|
| 5,616,585 A | 4/1997 | Bright |
| 5,700,810 A | 12/1997 | Natsugari et al. |
| 6,489,315 B1 | 12/2002 | Natsugari et al. |
| 7,238,721 B2 | 7/2007 | Chen et al. |
| 7,253,180 B2 | 8/2007 | Chen et al. |
| 7,253,195 B2 | 8/2007 | Chen et al. |
| 7,342,118 B2 | 3/2008 | Brodney et al. |
| 7,517,532 B2 | 4/2009 | Wai et al. |
| 7,638,629 B2 | 12/2009 | Hannam et al. |
| 7,741,315 B2 | 6/2010 | Vacca et al. |
| 7,812,040 B2 | 10/2010 | Wager |
| 7,897,632 B2 | 3/2011 | Kimura et al. |
| 7,902,195 B2 | 3/2011 | Hughes et al. |
| 7,923,450 B2 | 4/2011 | Baumann et al. |
| 8,097,621 B2 | 1/2012 | Bell et al. |
| 8,697,673 B2 | 4/2014 | Pettersson et al. |
| 8,916,564 B2 | 12/2014 | Pettersson et al. |
| 2002/0132817 A1 | 9/2002 | Natsugari et al. |
| 2003/0195205 A1 | 10/2003 | DeNinno et al. |
| 2004/0220186 A1 | 11/2004 | Bell et al. |
| 2006/0106035 A1 | 5/2006 | Hendrix et al. |
| 2006/0111372 A1 | 5/2006 | Hendrix et al. |
| 2007/0031416 A1 | 2/2007 | Shoji et al. |
| 2007/0117798 A1 | 5/2007 | Kimura et al. |
| 2007/0117839 A1 | 5/2007 | Kimura et al. |
| 2007/0155731 A1 | 7/2007 | Butora et al. |
| 2007/0197581 A1 | 8/2007 | Asberom et al. |
| 2008/0009490 A1 | 1/2008 | Williams et al. |
| 2008/0076738 A1 | 3/2008 | Cai et al. |

(Continued)

FOREIGN PATENT DOCUMENTS

| | | |
|---|---|---|
| EP | 1145714 | 10/2001 |
| GB | 1419789 | 12/1975 |

(Continued)

OTHER PUBLICATIONS

Caldwell, J.P., et al., "Iminoheterocycles as □-secretase modulators", Bioorganic & Medicinal Chemistry Letters, Sep. 15, 2010, pp. 5380-5384; 20(18).
Eiden, F, et al., "1-Pyrono-und 1-Pyridono-[3,4-b]chinoxaline. 33. Mitt. über Untersuchungen an 4-Pyronen", Archly der Pharmazie, 1972, pp. 2-9; 305(1).
Eiden, F., et al., Pyrono-Chinoxaline AUS 3-Hydroxy-4-Pyronen1), Tetrahedron Letters, 1968, pp. 2903-2904, 9(24).
Garbaccio, R.M., et al., "Discovery of Oxazolobenzimidazoles as Positive Allosteric Modulators for the mGluR2 Receptors", ACS Medicinal Chemistry Letters, 2010, pp. 406-410; 1(8).
Gillman, K., et al., "Discovery and Evaluation of BMS-708163, a Potent Selective and Orally Bioavailable y-Secretase Inhibitor", ACS Medicinal Chemistry Letters, Mar. 22, 2010, pp. 120-124; 1(3).
Goel, A., et al., "Amberlyst 15-Catalyzed Efficient synthesis of 5-Acetyl-4-hydroxy-coumarone and 5-Acetyl-6-hydroxy-coumarone: Crucial Precursors for Several Naturally Occurring Furanoflavones1", Synlett, 2004, pp. 1990-1994; vol. 11.

(Continued)

*Primary Examiner* — Karl J Puttlitz
(74) *Attorney, Agent, or Firm* — J. Michael Dixon

(57) ABSTRACT

Compounds and pharmaceutically acceptable salts of the compounds are disclosed, wherein the compounds have the structure of Formula I Formula I wherein X, $R^1$, $R^{2a}$, $R^{2b}$, $R^{4a}$, $R^{4b}$, $R^{5a}$, $R^{5b}$, $R^6$, $R^7$, $R^{10}$, $R^{11}$, and y are as defined in the specification. Corresponding pharmaceutical compositions, methods of treatment, methods of synthesis, and intermediates are also disclosed.

53 Claims, No Drawings

(56) References Cited

U.S. PATENT DOCUMENTS

| | | |
|---|---|---|
| 2008/0194591 A1 | 8/2008 | Entwistle et al. |
| 2008/0207900 A1 | 8/2008 | Kimura et al. |
| 2008/0280948 A1 | 11/2008 | Baumann et al. |
| 2009/0062529 A1 | 3/2009 | Kimura et al. |
| 2009/0163482 A1 | 6/2009 | McHardy et al. |
| 2009/0215759 A1 | 8/2009 | Baumann et al. |
| 2009/0306054 A1 | 12/2009 | Cai et al. |
| 2010/0016373 A1 | 1/2010 | Khilevich et al. |
| 2010/0041680 A1 | 2/2010 | Rivkin |
| 2010/0093731 A1 | 4/2010 | Goetschi et al. |
| 2010/0105904 A1 | 4/2010 | Kimura et al. |
| 2010/0120874 A1 | 5/2010 | Baumann et al. |
| 2010/0130495 A1 | 5/2010 | Forsblom et al. |
| 2010/0137320 A1 | 6/2010 | Huang et al. |
| 2010/0204230 A1 | 8/2010 | Blurton et al. |
| 2010/0222320 A1 | 9/2010 | Fischer et al. |
| 2010/0247514 A1 | 9/2010 | Zhu et al. |
| 2010/0255005 A1 | 10/2010 | Zhu et al. |
| 2010/0256128 A1 | 10/2010 | Zhu et al. |
| 2010/0297128 A1 | 11/2010 | Huang et al. |
| 2010/0298359 A1 | 11/2010 | Huang et al. |
| 2010/0298372 A1 | 11/2010 | Huang et al. |
| 2010/0298381 A1 | 11/2010 | Zhu et al. |
| 2011/0009392 A1 | 1/2011 | Zhu et al. |
| 2011/0009619 A1 | 1/2011 | Kimura et al. |
| 2011/0015175 A1 | 1/2011 | Marcin et al. |
| 2011/0027264 A1 | 2/2011 | Huang et al. |
| 2011/0053918 A1 | 3/2011 | Zhu et al. |
| 2011/0070297 A1 | 3/2011 | Cao et al. |
| 2011/0082153 A1 | 4/2011 | Aslanian et al. |
| 2011/0118234 A1 | 5/2011 | Biswas et al. |
| 2011/0166132 A1 | 7/2011 | Hitchcock et al. |
| 2011/0172427 A1 | 7/2011 | Nakamura et al. |
| 2011/0207733 A1 | 8/2011 | Rivkin et al. |
| 2011/0237580 A1 | 9/2011 | Gijsen et al. |
| 2011/0251172 A1 | 10/2011 | Rivkin et al. |
| 2011/0257156 A1 | 10/2011 | Zhu et al. |
| 2011/0263529 A1 | 10/2011 | Xu et al. |
| 2011/0275822 A1 | 11/2011 | Minamisono et al. |
| 2011/0281881 A1 | 11/2011 | Gijsen et al. |
| 2011/0294784 A1 | 12/2011 | Asberom et al. |
| 2011/0313001 A1 | 12/2011 | Fischer et al. |
| 2012/0022044 A1 | 1/2012 | Fischer et al. |
| 2012/0022090 A1 | 1/2012 | Gijsen et al. |
| 2012/0053165 A1 | 3/2012 | Allen et al. |
| 2012/0252758 A1 | 10/2012 | Pettersson et al. |
| 2014/0045790 A1 | 2/2014 | Pettersson et al. |
| 2014/0088111 A1 | 3/2014 | Pettersson et al. |
| 2015/0274721 A1* | 10/2015 | Pettersson ............ C07D 471/04 514/249 |

FOREIGN PATENT DOCUMENTS

| | | |
|---|---|---|
| WO | 9944955 | 10/1999 |
| WO | 2004024078 | 3/2004 |
| WO | 2006126081 | 11/2006 |
| WO | 2006126082 | 11/2006 |
| WO | 2006126083 | 11/2006 |
| WO | 2007063385 | 6/2007 |
| WO | 2007088450 | 8/2007 |
| WO | 2007088462 | 8/2007 |
| WO | 2007099423 | 9/2007 |
| WO | 2007138431 | 12/2007 |
| WO | 2008137102 | 11/2008 |
| WO | 2009050227 | 4/2009 |
| WO | 2009061699 | 5/2009 |
| WO | 2010075204 | 7/2010 |
| WO | 2010098332 | 9/2010 |
| WO | 2010098488 | 9/2010 |
| WO | 2010098495 | 9/2010 |
| WO | 2010098496 | 9/2010 |
| WO | 2011048525 | 4/2011 |
| WO | 2012131539 | 10/2012 |
| WO | 2013171712 A1 | 11/2013 |
| WO | 2014047372 A1 | 3/2014 |
| WO | 2014096212 A1 | 6/2014 |
| WO | 2014111457 | 7/2014 |
| WO | 2015049616 | 4/2015 |

OTHER PUBLICATIONS

Grunewald, G.L, et al., "Binding Requirements of Phenolic Phenylethylamines in the Benzonorbomene skeleton at the Active site of Phenylethanolamine N-Methyltransferase1a,b", Journal Medical Chemistry, Sep. 1986, pp. 1972-1982; 29(10).

Haleblian, et al., "Characterization of Habits and Crystalline Modification of Solids and Their Pharmaceutical Applications", Journal of Pharmaceutical Science, Aug. 1975, pp. 1269-1288; 64(8).

Hashimoto, T., et al., "A Novel Gamma-secretase Modulator-Pharmacology Part", Journal of Alzheimer's & Dementia, Jul. 2010, Supplemental, pp. S242 (PI-236); 6(4).

Huang, X, et al., "The Discovery of Pyridone and Pyridazone Heterocycles as □-Secretase Modulators", ACS Medicinal Chemistry Letters, 2010, pp. 184-187; 1(4).

Hughes, J.D., et al., "Physiochemical drug properties associated with in vivo toxicological outcomes", Bioorganic & Medicinal Chemistry Letters, Sep. 1, 2008, pp. 4872-4875; 18(17).

Inamoto, K., et al., "Palladium-Catalyzed Synthesis of 2-Substituted Benzothiazoles via a C-H Functionalization/Intramolecular C-S Bond Formation Process", Organic Letters, 2008, pp. 5147-5150; 10(22).

Kato, D., et al.,"Microbial Deracemization of α-Substituted Carboxylic Acids: Substrate Specificity and Mechanistic Investigation", Journal Organic Chemistry, Sep. 19, 2003, pp. 7234-7242; 68(19).

Kawahara, N., et al., "A simple synthesis of dimethyl 2-pyridone-4, 5-dicarboxylate derivatives", Journal of Heterocyclic Chemistry, 1989, pp. 847-852; 26(3).

Kawahara, N., et al., "Synthesis and Thermal Cyclization Reactions of Methyl Isocrotonate Derivatives", Chemical & Pharmaceutical Bulletin, Feb. 1987, pp. 457-467; 35(2).

Kounnas, Maria Z., et al., "Modulation of ?-Secretase Reduces β-Amyloid Deposition in a Transgenic Mouse Model of Alzheimer's Disease", Neuron, Sep. 9, 2010, pp. 769-780; 67(5).

Lee. J.C., et al. "Facile Synthesis of Oxazoles Starting from Ketones", Synthetic Communications 2003, pp. 1611-1614; 33(9).

Lin, Y., et al., "New Synthesis of Isoxazoles and Isothiazoles. A Convenient Synthesis of Thioenaminones from Enaminones", Journal of Organic Chemistry, Nov. 1980, pp. 4857-4860; 45(24).

Liu, J., et al., "Synthesis and Photophysical Properties of New Fluorinated Benzo[c]xanthene Dyes as Intracellular pH Indicators", Bioorganic & Medicinal Chemistry Letters, 2001, pp. 2903-2905; 11(22).

Liu, W., et al., "Total synthesis of Isoprekinamycin: Structural Evidence for Enhanced Diazonium Ion Character and Growth Inhibitory Activity toward Cancer Cells", Organic Letters, 2007, pp. 2915-2918; 9(15).

Morphy, Richard, "The Influence of Target Family and Functional Activity on the Physicochemical Properties of Pre-Clinical Compounds", Journal of Medicinal Chemistry, 2006, pp. 2969-2978; 49(10).

Narender, N., et al., "Highly Efficient, Para-selective Oxychlorination of Aromatic Compound Using Potassium Chloride and Oxone", Synthetic Communication 2002, pp. 279-286; 32(2).

Oliveira, M.M., et al., "Synthesis and photochromic behavior under flash photolysis and continuous irradiation of novel 2H-chromenes derived from hydroxydibenzothiophenes", Tetrahedron, Feb. 25, 2002, pp. 1709-1718; 58(9).

Olsen, R., et al., "Secretase Inhibitors and Modulators for the Treatment of Alzheimer's Disease", Annual Report in Medicinal Chemistry, 2007, pp. 27-47; vol. 42.

Platonov, D., et al., "Synthesis of substituted 2-alkyl-5-hydroxy-1-oxo-1,2-dihydroisoquinolines and their new condensed structures", Mendeleev Communications, 2010, pp. 83-85; vol. 20.

Rivkin, A. et al., "Piperazinyl Pyrimidine Derivatives as Potent □-Secretase Modulators", Bioorganic & Medicinal Chemistry Letters, Feb. 1, 2010, pp. 1269-1271; 20(3).

(56) References Cited

OTHER PUBLICATIONS

Rivkin, X., et al., "Purine Derivatives as Potent □-Secretase Modulators", Bioorganic & Medicinal Chemistry Letters, Apr. 1, 2010, pp. 2279-2282; 20( 7).

Sanz, R., et al., "Regioselective Synthesis of 4- and 7-Alkoxyindoles from 2,3-Dihalophenols: Application to the Preparation of Indole Inhibitors of Phospholipase A2"Journal Organic Chemistry, Jun. 6, 2007, pp. 5113-5118; 72(14).

Shen, L., et al., "Synthesis and structure-activity relationships of thiadiazole-derivatives as potent and orally active peroxisome proliferator-activated receptors α/? dual agonists", Bioorganic Medicinal Chemistry, Mar. 15, 2008, pp. 3321-3341; 16(6).

Shtarev, A.B., et al., "Partially Bridge-Fluorinated Dimethyl Bicyclo[1.1.1.]pentane-1,3-dicarboxylates: Preparation and NMR Spectra", Journal American Chemical Society, 2001, pp. 3484-3492; 123(15).

Shultz, D.A., et al., "Design, Synthesis, and Properties of Conformationally Fixed Semiquinone Monoradical Species", Journal Organic Chemistry, Nov. 24, 2006, pp. 9104-9113; 71(24).

Tsunoda, T., et al., "1,1'-(Azodicarbonyl)dipiperidine-Tributylphosphines, A New Reagent System for Mitsunobu Reaction", Tetrahedron Letters, Mar. 5, 1993, pp. 1639-1642; 34(10).

Van Camp, J.A., et al., "Preparation of 4-aryl-2-trifluoromethylbenzonitrile derivatives as androgen receptor antagonists for topical suppression of sebum production", Bioorganic & Medicinal Chemistry Letters, 2007, pp. 5529-5532; 17(20).

Wager, T.T., et al., "Defining Desirable Central Nervous System Drug Space through the Alignment of Molecular Properties, in Vitro ADME, and Safety Attributes", ACS Chemical Neuroscience, 2010, pp. 420-434; 1(6).

Wai, J.S., et al., "Dihydroxypryridopyrazine-1,6-dione HIV-1 integrase inhibitors", Bioorganic & Medicinal Chemistry Letters, 2007, pp. 5595-5599; 17(20).

Zhang J. et al., "TiCl4-Catalyzed Friedel-Crafts Reaction of Trifluoroacetaldehyde Ethyl Hemiacetal (TFAE)", Synthetic Communications, 2011, pp. 3045-3052; 41(20).

Zhu, Zhanoning, et al., "Discovery of Cyclic Acylguanidines as Highly Potent and Selective β-Site Amyloid Cleaving Enzyme (BACE) Inhibitors: Part 1-Inhibitor Design and Validation", Journal of Medicinal Chemistry Letters, 2010, pp. 951-965; 53(3).

Zoellinger, M., et al., "Skeleton Diversity by Cyclopropanation of Tricyclic Acylenamines", Journal of Chemical Sciences, 2009, pp. 617-623; 64(b).

Kawahara, N., et al., "A Synthesis of Pyrido[1,2-a]Quinoxalines and Pryrido[1,2-a]-Pyrazines1)", Heterocycles, 1983, pp. 1721-1725; 20(9).

International application No. PCT/IB2012/051348, filed Mar. 21, 2012, Search Report dated May 11, 2012, 4 pages.

International application No. PCT/IB2012/051348, filed Mar. 21, 2012, Written Opinion of International Searching Authority, dated May 11, 2012, 7 pages.

International application No. PCT/IB2013/058347, filed Sep. 6, 2013, Search Report and Written Opinion, dated Jan. 15, 2014, 10 pages.

International Search Report and the Written Opinion of the International Searching Authority, PCT/IB2015/051988, dated May 12, 2015.

Pettersson, M. et al., Design, Synthesis, and Pharmacological Evaluation of a Novel Series of Pyridopyrazine-1-6-dione y-Secretase Modulators, Journal of Medicinal Chemistry, Feb. 13, 2014, pp. 1046-1062, vol. 57(3).

Pettersson, M. et al., Design of Pyridopyrazine-1,6-dione γ-Secretase Modulators that Align Potency, MDR Efflux Ratio, and Metabolic Stability, ACS Medicinal Chemistry Letters, 2015, 6(5), pp. 596-601.

Pettersson, M. et al., Discovery of indole-derived pyridopyrazine-1,6-dione c-secretase modulators that target presenilin, Bioorganic & Medicinal Chemistry Letters, Feb. 15, 2015;25(4):908-13.

Tran, T. P. et al., Synthesis of Pyridopyrazine-1,6-diones from 6-Hydroxypicolinic Acids via a One-Pot Coupling/Cyclization Reaction, Organic Letters, 2013, vol. 15, No. 3, pp. 642-645.

International Search Report and th Written Opinion of the International Searching Authority, PCT/IB2014/064738 dated Dec. 15, 2014.

International Search Report and th Written Opinion of the International Searching Authority, PCT/IB2016/050384 dated Jan. 26, 2016.

\* cited by examiner

CYCLOPROPABENZOFURANYL PYRIDOPYRAZINEDIONES

CROSS REFERENCE

This application is a continuation of U.S. patent application Ser. No. 15/012,954, filed Feb. 2, 2016 which claims priority from U.S. Provisional Patent Application Ser. No. 62/111,222, filed Feb. 3, 2015, the contents of which are incorporated by reference

FIELD OF THE INVENTION

The present invention relates to novel cyclopropabenzofuranyl pyridopyrazinedione compounds of Formula I useful for the treatment of neurodegenerative and/or neurological disorders, such as Alzheimer's disease, etc.

BACKGROUND OF THE INVENTION

Dementia results from a wide variety of distinctive pathological processes. The most common pathological processes causing dementia are Alzheimer's disease (AD), cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD affects nearly half of all people past the age of 85, the most rapidly growing portion of the United States population. As such, the number of AD patients in the United States is expected to increase from about 4 million to about 14 million by 2050.

The present invention relates to a group of γ-secretase modulators, useful for the treatment of neurodegenerative and/or neurological disorders such as Alzheimer's disease and Down's syndrome. (see Ann. Rep. Med. Chem. 2007, Olsen et al., 42: 27-47).

SUMMARY OF THE INVENTION

The present invention is directed to γ-secretase modulators as described by Formula I:

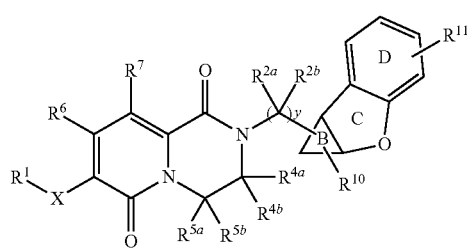

Formula I or pharmaceutically acceptable salts thereof, wherein:

X is a (5- to 14-membered)heteroaryl containing 1-3 heteroatoms;

$R^1$, where chemically permissible, is selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—O$R^4$;

$R^{2a}$ and $R^{2b}$, where chemically permissible, at each occurrence, are independently selected from the group consisting of hydrogen, halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—O$R^4$; or $R^{2a}$ and $R^{2b}$ together with the carbon atom(s) to which they are attached form a ($C_3$-$C_8$)cycloalkyl or a (4- to 10-membered)heterocycloalkyl, wherein the ($C_3$-$C_8$)cycloalkyl and the (4- to 10-membered)heterocycloalkyl are optionally substituted with one to three $R^8$;

$R^{4a}$ and $R^{4b}$, where chemically permissible, are each independently selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—O$R^4$; or $R^{4a}$ and $R^{4b}$ together with the carbon atom to which they are attached form a ($C_3$-$C_8$)cycloalkyl, wherein the ($C_3$-$C_8$)cycloalkyl is optionally substituted with one to three $R^8$;

$R^{5a}$ and $R^{6b}$, at each occurrence, are independently selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio ($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—O$R^4$; or $R^{5a}$ and $R^{6b}$ together with the carbon atom to which they are attached form a ($C_3$-$C_8$)cycloalkyl, wherein said ($C_3$-$C_8$)cycloalkyl is optionally substituted with one to three $R^8$;

$R^6$ and $R^7$ are each independently selected from the group consisting of hydrogen, halogen, cyano, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy ($C_1$-$C_6$)alkyl, optionally substituted ($C_3$-$C_8$)cycloalkyl, optionally substituted phenyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, —C(=O)—O$R^4$, and —O$R^9$; provided that $R^6$ and $R^7$ cannot both be hydroxy;

$R^8$, at each occurrence, is independently selected from the group consisting of cyano, halogen, hydroxy, —$SF_5$, nitro, optionally substituted ($C_1$-$C_6$)alkyl, optionally substituted ($C_1$-$C_6$)alkoxy, and optionally substituted ($C_1$-$C_6$)alkoxy ($C_1$-$C_6$)alkyl;

$R^9$ is selected from the group consisting of hydrogen and optionally substituted ($C_1$-$C_6$)alkyl;

y is an integer selected from 1, 2, 3 or 4;

ring B is optionally substituted with one to three $R^{10}$, wherein each $R^{10}$ is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, —C(=O)—O$R^4$; or two $R^{10}$ substituents taken together with the carbon atom(s) to which they are attached form an optionally substituted ($C_3$-$C_8$)cycloalkyl;

ring D is optionally substituted with one to four $R^{11}$, wherein each $R^{11}$ is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, optionally substituted (4- to 6-membered)heterocycloalkyl; —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—O$R^4$; and $R^4$ and $R^5$, at each occurrence, are each independently selected from hydrogen or optionally substituted ($C_1$-$C_6$)alkyl;

provided that the compound is not 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione.

Compounds of the invention include Examples 2-22, C22, C33, C40 and C44 or a pharmaceutically acceptable salt thereof as described herein.

Also provided herein are compositions comprising a pharmaceutically effective amount of one or more of the compounds described herein and a pharmaceutically acceptable vehicle, carrier or excipient.

The compounds of Formula I are γ-secretase modulators. γ-Secretase plays a role in the production of amyloid beta protein (Aβ) plaques associated with Alzheimer's disease. Accordingly, the compounds of Formula I are believed to be useful in treating a variety of neurodegenerative and/or neurological disorders related to Aβ production.

Other features and advantages of this invention will be apparent from this specification and the appending claims which describe the invention.

DETAILED DESCRIPTION OF THE INVENTION

The headings within this document are only being utilized to expedite its review by the reader. They should not be construed as limiting the invention or claims in any manner.
Definitions and Exemplifications As used throughout this application, including the claims, the following terms have the meanings defined below, unless specifically indicated otherwise. The plural and singular should be treated as interchangeable, other than the indication of number:

The term "($C_1$-$C_6$)alkyl" refers to a linear or branched-chain saturated hydrocarbyl substituent (i.e., a substituent obtained from a hydrocarbon by removal of a hydrogen) containing from 1 to 6 carbon atoms. Examples of such substituents include methyl, ethyl, propyl (including n-propyl and isopropyl), butyl (including n-butyl, isobutyl, sec-butyl and tert-butyl), pentyl, and hexyl.

The term "optionally substituted ($C_1$-$C_6$)alkyl", as used herein, refers to a ($C_1$-$C_6$)alkyl as defined above, in which one or more hydrogen atoms are replaced by a substituent selected from the group consisting of halogen, oxo, cyano, hydroxy, —$SF_5$, nitro, —N($R^4$)($R^5$), —N($R^4$)(C(=O)$R^5$), —N($R^4$)C(=O)—O$R^5$, —C(=O)—N($R^4$)($R^5$), —O—C(=O)N($R^4$)($R^5$), —C(=O)—$R^4$, —C(=O)—O$R^4$, and ($C_3$-$C_8$)cycloalkyl, in which $R^4$ and $R^5$ are each independently hydrogen or optionally substituted ($C_1$-$C_6$)alkyl. For example, a ($C_1$-$C_6$)alkyl moiety can be substituted with one or more halogen atoms to form a "halo($C_1$-$C_6$)alkyl". Representative examples of a halo($C_1$-$C_6$)alkyl include, but are not limited to, fluoromethyl, difluoromethyl, trifluoromethyl, fluoroethyl, difluoroethyl, pentafluoroethyl, and the like.

The term "($C_1$-$C_3$)alkyl" refers to a linear or branched-chain saturated hydrocarbyl substituent (i.e., a substituent obtained from a hydrocarbon by removal of a hydrogen) containing from 1 to 3 carbon atoms. Examples of such substituents include methyl, ethyl, and propyl (including n-propyl and isopropyl).

The term "($C_2$-$C_6$)alkenyl" refers to an aliphatic hydrocarbon having from 2 to 6 carbon atoms and having at least one carbon-carbon double bond, including straight chain or branched-chain groups having at least one carbon-carbon double bond. Representative examples include, but are not limited to, ethenyl, 1-propenyl, 2-propenyl (allyl), isopropenyl, 2-methyl-1-propenyl, 1-butenyl, and 2-butenyl. When the compounds of the invention contain a ($C_2$-$C_6$) alkenyl group, the compound may exist as the pure E (entgegen) form, the pure Z (zusammen) form, or any mixture thereof.

The term "optionally substituted ($C_2$-$C_6$)alkenyl" refers to a ($C_2$-$C_6$)alkenyl as defined above, in which one or more hydrogen atoms are replaced by a substituent selected from the group consisting of halogen, oxo, cyano, hydroxy, —$SF_5$, nitro, —N($R^4$)($R^5$), —N($R^4$)(C(=O)$R^5$), —($R^4$)C(=O)—O$R^5$, —C(=O)—N($R^4$)($R^5$), —O—C(=O)N($R^4$)($R^5$), —C(=O)—$R^4$, —C(=O)—O$R^4$, and ($C_3$-$C_8$)cycloalkyl, in which $R^4$ and $R^5$ are each independently hydrogen or optionally substituted ($C_1$-$C_6$)alkyl.

The term "($C_2$-$C_6$)alkynyl" refers to an aliphatic hydrocarbon having from 2 to 6 carbon atoms and having at least one carbon-carbon triple bond, including straight chain or branched chain groups having at least one carbon-carbon triple bond. Representative examples of an alkynyl include, but are not limited to, acetylenyl, 1-propynyl, 2-propynyl, 3-butynyl, 2-pentynyl, and 1-butynyl.

The term "optionally substituted ($C_2$-$C_6$)alkynyl" refers to a ($C_2$-$C_6$)alkynyl as defined above, in which one or more hydrogen atoms are replaced by a substituent selected from the group consisting of halogen, oxo, cyano, hydroxy, —$SF_5$, —N($R^4$)($R^5$), —N($R^4$)(C(=O)$R^5$), —N($R^4$)C(=O)—O$R^5$, —C(=O)—N($R^4$)($R^5$), —O—C(=O)N($R^4$)($R^5$), —C(=O)—$R^4$, —C(=O)—O$R^4$, and ($C_3$-$C_8$)cycloalkyl, in which $R^4$ and $R^5$ are each independently hydrogen or optionally substituted ($C_1$-$C_6$)alkyl.

The term "halogen" refers to fluorine (which may be depicted as —F), chlorine (which may be depicted as —Cl), bromine (which may be depicted as —Br), or iodine (which may be depicted as —I).

The term "($C_1$-$C_6$)alkoxy" as used herein, means a ($C_1$-$C_6$)alkyl group, as defined above, attached to the parent molecular moiety through an oxygen atom. Examples include, but are not limited to, methoxy, ethoxy, propoxy, 2-propoxy, butoxy, tert-butoxy, pentyloxy, and hexyloxy.

The term "optionally substituted ($C_1$-$C_6$)alkoxy" as used herein, refers to a ($C_1$-$C_6$)alkoxy group, as defined above, in which one or more hydrogen atoms are replaced by a substituent selected from the group consisting of halogen, oxo, cyano, hydroxy, —$SF_5$, nitro, —N($R^4$)($R^5$), —N($R^4$)(C(=O)$R^5$), —($R^4$)C(=O)—O$R^5$, —C(=O)—N($R^4$)($R^5$), —O—C(=O)N($R^4$)($R^5$), —C(=O)—$R^4$, —C(=O)—O$R^4$, and ($C_3$-$C_8$)cycloalkyl, in which $R^4$ and $R^5$ are each independently hydrogen or optionally substituted $(C_1-C_6)$ alkyl. For example, a $(C_1-C_6)$alkoxy can be substituted with one or more halogen atoms to form a "halo$(C_1-C_6)$alkoxy". Representative examples of a halo$(C_1-C_6)$alkoxy include, but are not limited to, fluoromethoxy, difluoromethoxy, trifluoromethoxy, fluoroethoxy, and pentafluoroethoxy, and the like.

The term "$(C_1-C_6)$alkoxy$(C_1-C_6)$alkyl" as used herein, means a $(C_1-C_6)$alkoxy group, as defined above, attached to the parent moiety through a $(C_1-C_6)$alkyl group, as defined above. Examples include, but are not limited to, methoxymethyl, methoxyethyl and the like.

The term "optionally substituted $(C_1-C_6)$alkoxy$(C_1-C_6)$alkyl" as used herein, means a $(C_1-C_6)$alkoxy$(C_1-C_6)$alkyl group, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$O$—$C(=O)N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

The term "thio$(C_1-C_6)$alkyl" as used herein, means a $(C_1-C_6)$alkyl group, as defined above, appended to the parent molecular moiety through a sulfur atom. Representative examples of thio$(C_1-C_6)$alkylthio include, but are not limited to, thiomethyl, thioethyl, thio(tert-butyl), and thiohexyl.

The term "optionally substituted thio$(C_1-C_6)$alkyl", as used herein, refers to a thio$(C_1-C_6)$alkyl group, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$O$—$C(=O)N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

The term "$(C_3-C_8)$cycloalkyl" refers to a carbocyclic substituent obtained by removing a hydrogen from a saturated carbocyclic molecule having from 3 to 8 carbon atoms. A "$(C_3-C_6)$cycloalkyl" refers to a carbocyclic substituent obtained by removing a hydrogen from a saturated carbocyclic molecule having from 3 to 6 carbon atoms. A "$(C_3-C_8)$cycloalkyl" may be a monocyclic ring, examples of which include cyclopropyl, cyclobutyl, cyclopentyl, cyclohexyl, cycloheptyl, and cyclooctyl. Alternatively, a cycloalkyl may contain more than one ring, such as a $(C_4-C_8)$bicycloalkyl. The term "$(C_4-C_8)$bicycloalkyl" refers to a bicyclic system containing 4 to 8 carbon atoms. The bicycloalkyl may be fused, such as bicyclo[1.1.0]butane, bicyclo[2.1.0]pentane, bicyclo[2.2.0]hexane, bicyclo[3.1.0]hexane, bicyclo[3.2.0]heptane and bicyclo[3.3.0]octane. The term "bicycloalkyl" also includes bridged bicycloalkyl systems such as, but not limited to, bicyclo[2.2.1]heptane and bicyclo[1.1.1]pentane.

The term "optionally substituted "$(C_3-C_8)$cycloalkyl" refers to a $(C_3-C_8)$cycloalkyl, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$O$—$C(=O)N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

The term "$(C_6-C_{10})$aryl" refers to an aromatic substituent containing from 6 to 10 carbon atoms, consisting of one ring or two fused rings. Examples of such aryl substituents include, but are not limited to, phenyl and naphthyl. The $(C_6-C_{10})$aryl may also include phenyl and naphthyl substituents that are optionally fused to a $(C_3-C_6)$cycloalkyl ring (e.g., bicyclo[4.2.0]octa-1,3,5-trienyl) or a (5- to 6-membered)heterocycloalkyl ring (e.g., dihydrobenzofuranyl, benzodioxolyl, and oxoisoindolinyl) as defined herein, wherein a group having such a fused aryl group as a substituent is attached to a carbon atom of the aryl. When the aryl is phenyl, it is also referred to herein as an "optionally substituted phenyl".

The term "optionally substituted $(C_6-C_{10})$aryl" refers to a $(C_6-C_{10})$aryl, as defined above, in which one or more hydrogen atoms are replaced by a substituent selected from the group consisting of halogen, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$O$—$C(=O)N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

The term "heterocycloalkyl," as used herein, refers to a cycloalkyl as defined above, wherein at least one of the ring carbon atoms is replaced with a heteroatom selected from nitrogen, oxygen or sulfur. A "(4- to 10-membered)heterocycloalkyl" refers to a heterocycloalkyl substituent as defined above containing a total of 4 to 10 ring atoms, wherein at least one of the ring atoms is a heteroatom selected from oxygen, nitrogen, or sulfur. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is attached to the group may be the at least one heteroatom, when the heteroatom is a nitrogen having the appropriate valence, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom when the heteroatom is a nitrogen having the appropriate valence, or it may be bound to a ring carbon atom, where the ring carbon atom may be in the same ring as the at least one heteroatom or where the ring carbon atom may be in a different ring from the at least one heteroatom.

Also included in the definition of "heterocycloalkyl" are heterocycloalkyls that are fused to a $(C_6-C_{10})$aromatic ring or a (5- to 10-membered)heteroaromatic ring. When such a fused heterocycloalkyl group is substituted with one or more substituents, the one or more substituents, unless otherwise specified, are each bound to a heteroatom of the heterocycloalkyl group when the heteroatom is nitrogen having the appropriate valence or to a carbon atom of the heterocycloalkyl group. Examples of heterocycloalkyl rings include, but are not limited to, azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydrooxazolyl, morpholinyl, oxetanyl, tetrahydrodiazinyl, oxazinyl, oxathiazinyl, quinuclidinyl, chromanyl, isochromanyl, dihydrobenzoxazinyl, indolinyl, isoindolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo [4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-4-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like.

The term "optionally substituted heterocycloalkyl" [e.g., optionally substituted (4- to 6-membered)heterocycloalkyl] refers to a heterocycloalkyl, as defined above, in which one or more hydrogen atoms, where chemically permissible, are replaced by a substituent selected from the group consisting of halogen, oxo, cyano, hydroxy, —SF$_5$, nitro, —N(R$^4$)(R$^5$), —N(R$^4$)(C(=O)R$^5$), —N(R$^4$)C(=O)—OR$^5$, —C(=O)—N(R$^4$)(R$^5$), —O—C(=O)N(R$^4$)(R$^5$), —C(=O)—R$^4$, —C(=O)—OR$^4$, and (C$_3$-C$_8$)cycloalkyl, in which R$^4$ and R$^5$ are each independently hydrogen or optionally substituted (C$_1$-C$_8$)alkyl.

The term "(5- to 14-membered)heteroaryl" refers to a heteroaryl ring having from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)heteroaryl" refers to a heteroaryl ring having from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(6-membered)heteroaryl" refers to a hetroaryl ring having 6 ring atoms. A "(5-membered)heteroaryl" refers to a heteroaryl ring having 5 ring atoms in which at least one of the ring atoms is a heteroatom. A heteroaryl may consist of a single ring or 2 or 3 fused rings. Examples of heteroaryls include, but are not limited to, 6-membered ring substituents such as pyridinyl, pyrazinyl, pyrimidinyl and pyridazinyl; 5-membered heteroaryls such as triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, and pyrazolyl; 6/5-membered fused ring substituents such as indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, furanopyridinyl, purinyl, imidazopyridinyl, pyrrolopyridinyl, pyrazolopyridinyl, thienopyridinyl, triazolopyrimidinyl, triazolopyridinyl (e.g., [1,2,4]triazolo[1,5-a]pyridin-2-yl), and anthranilyl; and 6/6-membered fused ring substituents such as quinolinyl, isoquinolinyl, cinnolinyl, quinazolinyl, oxochromenyl, and 1,4-benzoxazinyl. In a group that has a heteroaryl substituent, the ring atom of the heteroaryl substituent that is bound to the group may be the at least one heteroatom when the heteroatom is nitrogen having the appropriate valence, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom when the heteroatom is a nitrogen having the appropriate valence or it may be bound to a ring carbon atom, where the ring carbon atom may be in the same ring as the at least one heteroatom, or where the ring carbon atom may be in a different ring from the at least one heteroatom.

It is to be understood that the "(5- to 14-membered)heteroaryl" may be optionally fused to a (C$_3$-C$_8$)cycloalkyl group, or to a (4- to 10-membered)heterocycloalkyl group, as defined herein. A group having such a fused heteroaryl group as a substituent is attached to an aromatic carbon of the heteroaryl group or to a heteroatom of the heteroaryl group when the heteroatom is nitrogen having the appropriate valence. Such a fused heteroaryl group may be substituted with up to four substituents; the substituents, unless otherwise specified, are each bound to an aromatic carbon of the heteroaryl group or to a heteroatom of the heteroaryl group when the heteroatom is nitrogen having the appropriate valence.

The terms "optionally substituted (5- to 14-membered)heteroaryl", "optionally substituted (5- to 6-membered)heteroaryl" and "optionally substituted (5- to 6-membered) nitrogen-containing heteroaryl" refer to a (5- to 14-membered)heteroaryl, a (5- to 6-membered)heteroaryl, and a (5- to 6-membered)nitrogen-containing heteroaryl, as defined above, in which one or more hydrogen atoms are replaced, where chemically permissible, by a substituent selected from the group consisting of halogen, oxo, cyano, hydroxy, —SF$_5$, nitro, —N(R$^4$)(R$^5$), —N(R$^4$)(C(=O)R$^5$), —N(R$^4$)C(=O)—OR$^5$, —C(=O)—N(R$^4$)(R$^5$), —O—C(=O)N(R$^4$)(R$^5$), —C(=O)—R$^4$, —C(=O)—OR$^4$, and (C$_3$-C$_8$)cycloalkyl, in which R$^4$ and R$^5$ are each independently hydrogen or optionally substituted (C$_1$-C$_6$)alkyl. The substituent can be attached to the heteroaryl moiety at any available carbon atom or to a heteroatom when the heteroatom is nitrogen having the appropriate valence.

The term "hydrogen" refers to a hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents are attached include, for example, alcohols, enols and phenol.

The term "cyano" (also referred to as "nitrile") means —CN, which also may be depicted:

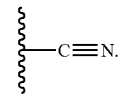

The term "oxo" means a =O group.

If a substituent is described as being "substituted," a non-hydrogen substituent is in the place of a hydrogen substituent on a carbon or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. As a further example, when there are optional substituents that can be present, e.g., $R^{10}$ or $R^{11}$, those substituents are as specified in the present specification, and when not present, the atom to which the optional substituent could be attached (i.e., C or N) would have the requisite number of hydrogens attached.

This specification uses the terms "substituent," "radical," and "group" interchangeably.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

If substituents are described as being "independently selected" from a group, each substituent is selected independent of the other(s). Each substituent therefore may be identical to or different from the other substituent(s).

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

"Patient" refers to warm-blooded animals such as, for example, pigs, cows, chickens, horses, guinea pigs, mice, rats, gerbils, cats, rabbits, dogs, monkeys, chimpanzees, and humans.

"Treating" or "treat", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Pharmaceutically acceptable" indicates that the substance or composition must be compatible, chemically and/or toxicologically, with the other ingredients comprising a formulation, and/or the mammal being treated therewith.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

As used herein the terms "Formula I", "Formula II", and "Formula III" may be hereinafter referred to as "compound(s) of the invention." Such terms are also defined to include all forms of the compounds of Formulas I through III including hydrates, solvates, isomers, crystalline and non-crystalline forms, isomorphs, polymorphs, and metabolites thereof. For example, the compounds of Formulas I through III, or pharmaceutically acceptable salts thereof, may exist in unsolvated and solvated forms with pharmaceutically acceptable solvents such as water, ethanol and the like. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. In general, the solvated forms are considered equivalent to the unsolvated forms for the purposes of the present invention.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the present invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

Compounds of the invention may exist as geometric isomers. The compounds of the invention may possess one or more asymmetric centers, thus existing as two, or more, stereoisomeric forms. The present invention includes all the individual stereoisomers and geometric isomers of the compounds of the invention and mixtures thereof. Individual enantiomers can be obtained by resolution, chiral chromatography, or other methods well-known to those skilled in the art, or by using the relevant enantiomeric reactant or reagent in the synthesis.

The carbon-carbon bonds of the compounds of the invention may be depicted herein using a solid line ( —— ), a solid wedge ( ▬ ), or a dotted wedge ( ....... ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry are marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropisomers, and mixtures thereof. The compounds of the invention may exhibit more than one type of isomerism, and consist of mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention also includes all pharmaceutically acceptable isotopically labeled compounds, which are identical to those recited in Formulas I through III except that one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention, for example those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by conventional techniques known to those skilled in the art or by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$. Compounds of the present invention, as well as the compounds exemplified in Examples 1-22 described below, include isotopically labeled versions of these compounds, such as, but not limited to, the deuterated and tritiated isotopes and all other isotopes discussed above.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the invention with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine (N-methylglucamine), olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine, and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of the present invention with certain moieties known to those skilled in the art as "pro-moieties" as described, for example, in "Design of Prodrugs" by H. Bundgaard (Elsevier, 1985).

This invention also encompasses compounds of the invention containing protective groups. One skilled in the art will appreciate that compounds of the invention can also be prepared with certain protecting groups that are useful for purification or storage and can be removed before administration to a patient. The protection and deprotection of functional groups is described in "Protective Groups in Organic Chemistry", edited by J. F. W. McOmie, Plenum Press (1973) and "Protective Groups in Organic Synthesis", 3rd edition, T. W. Greene and P. G. M. Wuts, Wiley-Interscience (1999).

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

Compounds

The compounds of Formula I, as depicted above, have a fused bicyclic core represented by 3,4-dihydro-2H-pyrido[1,2-a]pyrazine-1,6-dione. On the left side of the core, the pyridinone ring is substituted with $R^6$, $R^7$, and a (5- to 14-membered)heteroaryl moiety represented by X, wherein X is further substituted with $R^1$; and on the right side of the core the pyrazinone ring is substituted with $R^{4a}$, $R^{4b}$, $R^{5a}$, $R^{5b}$ and a pendant cyclopropabenzofuranyl moiety represented by the following structure:

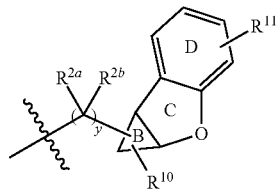

In certain embodiments, in Formula I as depicted above, $R^1$, $R^{2a}$, $R^{2b}$, $R^{4a}$, $R^{4b}$, $R^{5a}$, $R^{5b}$, $R^6$, $R^7$, $R^{10}$, $R^{11}$, and y are as defined above; and X is represented by:
  Xi) a (5- to 6-membered)heteroaryl containing 1-3 heteroatoms;
  Xii) a (6-membered)heteroaryl containing 1-3 heteroatoms; or
  Xiii) a (5-membered)heteroaryl containing 1-3 heteroatoms.

In certain other embodiments, the (5- to 6-membered) heteroaryl is selected from the group consisting of triazolyl, imidazolyl, furanyl, thiophenyl, pyrazolyl, isothiazolyl, thiazolyl, isoxazolyl, oxazolyl, pyridinyl, pyrimidinyl, pyrazinyl, and pyridazinyl.

In certain embodiments, the (6-membered)heteroaryl is selected from the group consisting of pyridinyl, pyrimidinyl, pyrazinyl, and pyridazinyl.

In certain other embodiments, the (5-membered)heteroaryl is selected from the group consisting of triazolyl, imidazolyl, furanyl, thiophenyl, pyrazolyl, isothiazolyl, thiazolyl, isoxazolyl, and oxazolyl.

In certain other embodiments, X is a (5-membered)heteroaryl, wherein the heteroaryl is imidazolyl.

In certain other embodiments, X is a (5-membered)heteroaryl, wherein the heteroaryl is triazolyl.

In certain other embodiments, in Formula I as depicted above, X is represented by one of the embodiments as immediately described above, wherein:

$R^1$, where chemically permissible, is selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—$OR^4$;

$R^{2a}$ and $R^{2b}$, where chemically permissible, at each occurrence, are independently selected from the group consisting of hydrogen, halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—$OR^4$; or $R^{2a}$ and $R^{2b}$ together with the carbon atom(s) to which they are attached form a ($C_3$-$C_8$)cycloalkyl or a (4- to 10-membered)heterocycloalkyl, wherein the ($C_3$-$C_8$)cycloalkyl and the (4- to 10-membered)heterocycloalkyl are optionally substituted with one to three $R^8$;

$R^{4a}$ and $R^{4b}$, where chemically permissible, are each independently selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —N($R^4$)($R^5$), —N($R^4$)(C(=O)$R^5$), —C(=O)N($R^4$)($R^5$), —O—C(=O)N($R^4$)($R^5$), —C(=O)—$R^4$, and —C(=O)—$OR^4$; or $R^{4a}$ and $R^{4b}$ together with the carbon atom to which they are attached form a ($C_3$-$C_8$)cycloalkyl, wherein the ($C_3$-$C_8$)cycloalkyl is optionally substituted with one to three $R^8$;

$R^{5a}$ and $R^{6b}$, at each occurrence, are independently selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —N($R^4$)($R^6$), —N($R^4$)(C(=O)$R^5$), —C(=O)N($R^4$)($R^5$), —O—C(=O)N($R^4$)($R^5$), —C(=O)—$R^4$, and —C(=O)—OR$^4$; or R$^{5a}$ and R$^{6b}$ together with the carbon atom to which they are attached form a (C$_3$-C$_8$)cycloalkyl, wherein said (C$_3$-C$_8$)cycloalkyl is optionally substituted with one to three R$^8$;

R$^6$ and R$^7$ are each independently selected from the group consisting of hydrogen, halogen, cyano, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_1$-C$_6$)alkoxy (C$_1$-C$_6$)alkyl, optionally substituted (C$_3$-C$_8$)cycloalkyl, optionally substituted phenyl, —N(R$^4$)(R$^5$), —N(R$^4$)(C=(O)R$^5$), —C(=O)N(R$^4$)(R$^5$), —O—C(=O)N(R$^4$)(R$^5$), —C(=O)—R$^4$, —C(=O)—OR$^4$, and —OR$^9$; provided that R$^6$ and R$^7$ cannot both be hydroxy;

R$^8$, at each occurrence, is independently selected from the group consisting of cyano, halogen, hydroxy, —SF$_5$, nitro, optionally substituted (C$_1$-C$_6$)alkyl, optionally substituted (C$_1$-C$_6$)alkoxy, and optionally substituted (C$_1$-C$_6$)alkoxy (C$_1$-C$_6$)alkyl;

R$^9$ is selected from the group consisting of hydrogen and optionally substituted (C$_1$-C$_6$)alkyl;

y is an integer selected from 1, 2, 3 or 4;

ring B is optionally substituted with one to three R$^{10}$, wherein each R$^{10}$ is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_3$-C$_8$)cycloalkyl, —N(R$^4$)(R$^5$), —N(R$^4$)(C=(O)R$^5$), —C(=O)N(R$^4$)(R$^5$), —O—C(=O)N(R$^4$)(R$^5$), —C(=O)—R$^4$, —C(=O)—OR$^4$; or two R$^{10}$ substituents taken together with the carbon atom(s) to which they are attached form an optionally substituted (C$_3$-C$_8$)cycloalkyl;

ring D is optionally substituted with one to four R$^{11}$, wherein each R$^{11}$ is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_3$-C$_8$)cycloalkyl, optionally substituted (4- to 6-membered)heterocycloalkyl; —N(R$^4$)(R$^5$), —N(R$^4$)(C=(O)R$^5$), —C(=O)N(R$^4$)(R$^5$), —O—C(=O)N(R$^4$)(R$^5$), —C(=O)—R$^4$, —C(=O)—OR$^4$; and R$^4$ and R$^5$, at each occurrence, are each independently selected from hydrogen or optionally substituted (C$_1$-C$_6$)alkyl;

provided that the compound is not 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione.

In certain other embodiments, in Formula I as depicted above, X is a (5-membered)heteroaryl selected from the group consisting of triazolyl, imidazolyl, furanyl, thiophenyl, pyrazolyl, isothiazolyl, thiazolyl, isoxazolyl, and oxazolyl, wherein:

R$^1$ is selected from the group consisting of hydrogen, halogen, cyano, hydroxy, optionally substituted (C$_1$-C$_6$)alkyl, and optionally substituted (C$_1$-C$_6$)alkoxy; wherein the (C$_1$-C$_6$)alkyl and (C$_1$-C$_6$)alkoxy are optionally substituted with one to three substituents selected from halogen, oxo, cyano, hydroxy, or —SF$_5$;

R$^{2a}$ and R$^{2b}$ are each independently selected from hydrogen, halogen, cyano, hydroxy or optionally substituted (C$_1$-C$_8$)alkyl;

R$^{4a}$, R$^{4b}$, R$^{5a}$ and R$^{5b}$ are each independently selected from the group consisting of hydrogen, halogen, cyano, hydroxy, oxo, —SF$_5$, optionally substituted (C$_1$-C$_6$)alkyl, and optionally substituted (C$_1$-C$_6$)alkoxy, wherein the (C$_1$-C$_6$)alkyl and (C$_1$-C$_6$)alkoxy are optionally substituted with one to three substituents selected from halogen, oxo, cyano, hydroxy, or —SF$_5$;

R$^6$ and R$^7$ are each independently selected from the group consisting of hydrogen, cyano, halogen, —SF$_5$, optionally substituted (C$_1$-C$_6$)alkyl, and optionally substituted (C$_1$-C$_8$)alkoxy, wherein the (C$_1$-C$_6$)alkyl and (C$_1$-C$_6$)alkoxy are optionally substituted with one to three substituents selected from halogen, oxo, cyano, hydroxy, or —SF$_5$;

y is 1, ring B is optionally substituted with one to two R$^{10}$, wherein each R$^{10}$ is independently selected from halogen, cyano, hydroxy, —SF$_5$, optionally substituted (C$_1$-C$_6$)alkyl, and optionally substituted (C$_1$-C$_8$)alkoxy, wherein the (C$_1$-C$_8$)alkyl and (C$_1$-C$_8$)alkoxy are optionally substituted with one to three substituents selected from halogen, oxo, cyano, hydroxy, or —SF$_5$; and ring D is optionally substituted with one to three R$^{11}$, wherein each R$^{11}$ is independently selected from the group consisting of halogen, cyano, hydroxy, optionally substituted (C$_1$-C$_8$)alkyl, optionally substituted (C$_1$-C$_8$)alkoxy, —SF$_5$, —N(R$^4$)(R$^5$), nitro, and optionally substituted (C$_3$-C$_8$)cycloalkyl, wherein the (C$_1$-C$_8$)alkyl, (C$_1$-C$_8$)alkoxy, and (C$_3$-C$_8$)cycloalkyl are optionally substituted with one to three substituents independently selected from halogen, cyano, hydroxy, —SF$_5$, and optionally substituted (C$_1$-C$_6$)alkyl, wherein R$^4$ and R$^5$ are each independently selected from hydrogen or optionally substituted (C$_1$-C$_6$)alkyl;

provided that the compound is not 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione.

In certain embodiments, in Formula I as immediately described above:

R$^1$ is an optionally substituted (C$_1$-C$_6$)alkyl, wherein the (C$_1$-C$_6$)alkyl is substituted with one to three substituents selected from halogen, oxo, cyano, hydroxy, or —SF$_5$; and R$^{2a}$, R$^{2b}$, R$^{4a}$, R$^{4b}$, R$^{5a}$ and R$^{5b}$ are each independently i) hydrogen; or ii) optionally substituted (C$_1$-C$_6$)alkyl, wherein the (C$_1$-C$_6$)alkyl is substituted with one to three substituents selected from halogen, oxo, cyano, hydroxy, or —SF$_5$.

In certain other embodiments, R$^1$ is methyl; and R$^{2a}$, R$^{2b}$, R$^{4a}$, R$^{4b}$, R$^{5a}$ and R$^{5b}$ are each independently hydrogen.

In certain other embodiments, R$^1$ is methyl; R$^{2a}$, R$^{2b}$, R$^{5a}$ and R$^{5b}$ are each independently hydrogen; and one of R$^{4a}$ and R$^{4b}$ is hydrogen and the other is methyl.

In another embodiment, R$^1$ is methyl; one of R$^{2a}$ and R$^{2b}$ is hydrogen and the other is methyl; and R$^{4a}$, R$^{4b}$, R$^{5a}$ and R$^{5b}$ are each independently hydrogen.

To further elucidate the compounds of the present invention, wherein X is a (5-membered)heteroaryl ring and the (5-membered)heteroaryl ring is imidazolyl or triazolyl, the following subgenuses are described below:

Formula II, as depicted below, is a subset of Formula I, as depicted above, wherein X is a (5-membered)heteroaryl wherein the heteroaryl is imidazolyl, R$^1$ is a (C$_1$-C$_6$)alkyl wherein the (C$_1$-C$_6$)alkyl is methyl, R$^6$ and R$^7$ are each hydrogen, y is 1, and the cyclopropabenzofuranyl moiety is attached via the benzylic position of the cyclopropabenzofuranyl moiety:

Formula II

In certain embodiments, in Formula II, as depicted above, or a pharmaceutically acceptable salt thereof:

$R^1$ is selected from the group consisting of hydrogen, halogen, cyano, hydroxy, optionally substituted $(C_1-C_6)$ alkyl, and optionally substituted $(C_1-C_6)$alkoxy; wherein the $(C_1-C_6)$alkyl and $(C_1-C_6)$alkoxy are optionally substituted with one to three substituents selected from halogen, oxo, cyano, hydroxy, or —SF$_5$;

$R^{2a}$, $R^{2b}$, $R^{4a}$, $R^{4b}$, $R^{5a}$ and $R^{5b}$ are each independently selected from hydrogen, halogen, cyano, hydroxy or optionally substituted $(C_1-C_6)$alkyl;

ring B is optionally substituted with one to two $R^{10}$, wherein each $R^{10}$ is independently selected from halogen or optionally substituted $(C_1-C_6)$alkyl; and ring D is optionally substituted with one to three $R^{11}$, wherein each $R^{11}$ is independently selected from halogen, optionally substituted $(C_1-C_6)$alkyl, and optionally substituted $(C_1-C_6)$alkoxy;

provided that the compound is not 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione.

In certain embodiments, Formula II is as immediately described above:

$R^1$ is selected from the group consisting of hydrogen, halogen, cyano, hydroxy, $(C_1-C_6)$alkyl, and $(C_1-C_6)$alkoxy; wherein the $(C_1-C_6)$alkyl and $(C_1-C_6)$alkoxy are optionally substituted with one to three fluoro atoms;

$R^{2a}$, $R^{2b}$, $R^{4a}$, $R^{4b}$, $R^{5a}$ and $R^{5b}$ are each independently selected from hydrogen or $(C_1-C_6)$alkyl, wherein the $(C_1-C_6)$alkyl is methyl;

ring B is optionally substituted with one to two $R^{10}$, wherein each $R^{10}$ is selected from:
i) halogen selected from fluoro or chloro, or
ii) $(C_1-C_6)$alkyl, wherein the $(C_1-C_6)$alkyl is methyl; and
ring D is optionally substituted with one to three $R^{11}$, wherein each $R^{11}$ is selected from:
i) halogen selected from fluoro or chloro;
ii) optionally substituted $(C_1-C_6)$alkyl, wherein the $(C_1-C_6)$alkyl is methyl and the methyl is optionally substituted with one to three fluoro (e.g., fluoromethyl, difluoromethyl, or trifluoromethyl); and
iii) optionally substituted $(C_1-C_6)$alkoxy, wherein the $(C_1-C_6)$alkoxy is methoxy and the methoxy is optionally substituted with one to three fluoro (e.g., fluoromethoxy, difluoromethoxy, or trifluoromethoxy).

In any of the above-mentioned embodiments for Formula II, $R^1$ is a $(C_1-C_6)$alkyl wherein the alkyl is methyl. In certain embodiments, when $R^1$ is methyl, the $R^1$—X moiety of Formula I is 4-methyl-1H-imidazol-1-yl.

Formula III, as depicted below, is a subset of Formula I as depicted above, wherein X is a (5-membered)heteroaryl, wherein the heteroaryl is triazolyl, $R^1$ is a $(C_1-C_6)$alkyl, wherein the $(C_1-C_6)$alkyl is methyl, $R^6$ and $R^7$ are each hydrogen, y is 1, and the cyclopropabenzofuranyl moiety is attached via the benzylic position of the cyclopropabenzofuranyl moiety:

Formula III

In certain embodiments, in Formula III, as depicted above, or a pharmaceutically acceptable salt thereof:

$R^1$ is selected from the group consisting of hydrogen, halogen, cyano, hydroxy, optionally substituted $(C_1-C_6)$ alkyl, and optionally substituted $(C_1-C_6)$alkoxy; wherein the $(C_1-C_6)$alkyl and $(C_1-C_6)$alkoxy are optionally substituted with one to three substituents selected from halogen, oxo, cyano, hydroxy, or —SF$_5$;

$R^{2a}$, $R^{2b}$, $R^{4a}$, $R^{4b}$, $R^{5a}$ and $R^{5b}$ are each independently selected from hydrogen, halogen, cyano, hydroxy or optionally substituted $(C_1-C_6)$alkyl;

ring B is optionally substituted with one to two $R^{10}$, wherein each $R^{10}$ is independently selected from halogen or optionally substituted $(C_1-C_6)$alkyl; and ring D is optionally substituted with one to three $R^{11}$, wherein each $R^{11}$ is independently selected from halogen, optionally substituted $(C_1-C_6)$alkyl, and optionally substituted $(C_1-C_6)$alkoxy;

In certain embodiments, Formula III is as immediately described above:

$R^1$ is selected from the group consisting of hydrogen, halogen, cyano, hydroxy, $(C_1-C_6)$alkyl, and $(C_1-C_6)$alkoxy; wherein the $(C_1-C_6)$alkyl and $(C_1-C_6)$alkoxy are optionally substituted with one to three fluoro atoms;

$R^{2a}$, $R^{2b}$, $R^{4a}$, $R^{4b}$, $R^{5a}$ and $R^{5b}$ are each independently selected from hydrogen or $(C_1-C_6)$alkyl, wherein the $(C_1-C_6)$alkyl is methyl;

ring B is optionally substituted with one to two $R^{10}$, wherein each $R^{10}$ is selected from:
i) halogen selected from fluoro or chloro, or
ii) $(C_1-C_6)$alkyl, wherein the $(C_1-C_6)$alkyl is methyl; and
ring D is optionally substituted with one to three $R^{11}$, wherein each $R^{11}$ is selected from:
i) halogen selected from fluoro or chloro;
ii) optionally substituted $(C_1-C_6)$alkyl, wherein the $(C_1-C_6)$alkyl is methyl and the methyl is optionally substituted with one to three fluoro (e.g., fluoromethyl, difluoromethyl, or trifluoromethyl); and
iii) optionally substituted $(C_1-C_6)$alkoxy, wherein the $(C_1-C_6)$alkoxy is methoxy and the methoxy is optionally substituted with one to three fluoro (e.g., fluoromethoxy, difluoromethoxy, or trifluoromethoxy).

In any of the above-mentioned embodiments for Formula III, $R^1$ is a $(C_1-C_6)$alkyl wherein the alkyl is methyl. In certain embodiments, when $R^1$ is methyl, the $R^1$—X moiety is 3-methyl-1H-1,2,4-triazol-1-yl.

In certain other embodiments, compounds of the present invention are selected from the group consisting of:

7-(4-methyl-1H-imidazol-1-yl)-2-{[1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione;

7-(4-methyl-1H-imidazol-1-yl)-2-{[(1aS,6bS)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione;

7-(4-methyl-1H-imidazol-1-yl)-2-{[(1aR,6bR)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione;

2-{[3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione;

2-{[(1aS,6bS)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione;

2-{[(1aR,6bR)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione;

2-{[(1aS,6bS)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-4-fluoro-1a-methyl-5-(trifluoromethoxy)-1,1a-dihydro-6bH-cyclopropa[b][1]benzofuran-6b-yl]methyl}-7-[4-(hydroxymethyl)-1H-imidazol-1-yl]-3,4-dihydro-2H-pyrido[1,2-a]pyrazine-1,6-dione;

7-(4-methyl-1H-imidazol-1-yl)-2-{[(1aS,6bS)-1a-methyl-5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione;

7-(4-methyl-1H-imidazol-1-yl)-2-{[(1aR,6bR)-1a-methyl-5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione;

2-{[(1aS,6bS)-4-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-4-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-3-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-3-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-3-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione; and 2-{[(1aR,6bR)-3-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione; or the pharmaceutically acceptable salts thereof.

In another embodiment, selected compounds of the present invention, or pharmaceutically acceptable salts thereof, may be useful for the treatment of neurodegeneration and psychiatric disorders, including Alzheimer's disease or Niemann-Pick disease type C.

In certain embodiments, selected compounds of the present invention may be useful for use in reducing the production of amyloid beta (Aβ) proteins in a subject in need thereof.

In certain embodiments, selected compounds of the present invention may be useful for treating Alzheimer's disease or Niemann-Pick disease type C in a patient, the method comprising administering a therapeutically effective amount of a compound of the present invention or a pharmaceutically acceptable salt thereof, to a patient in need thereof.

In certain embodiments, the present invention is directed to a pharmaceutical composition comprising selected compounds of the present invention, or a pharmaceutically acceptable salt thereof, and a pharmaceutically acceptable excipient.

In certain embodiments, the present invention is directed to a method for reducing the production of amyloid beta (Aβ) proteins in a subject in need thereof, the method comprising administering to said subject a therapeutically effective amount of a compound of Formula I, Formula II or Formula III, or a pharmaceutically acceptable salt thereof.

In certain other embodiments, the present invention is directed to a method of treating Alzheimer's disease in a subject in need thereof, the method comprising administering to said subject a therapeutically effective amount of a compound of Formula I, Formula II or Formula III, or a pharmaceutically acceptable salt thereof.

Pharmacology

Alzheimer's disease (AD) research indicates that the disease is associated with the buildup of plaques in variable shapes and sizes in the brain. The primary plaques associated with AD are composed of amyloid beta peptides (Aβ). Aβ is produced when the amyloid precursor protein (APP) undergoes successive proteolysis by the aspartyl proteases β- and γ-secretase (Haas et al., "*Trafficking and proteolytic processing of APP.*" Cold Spring Harbor Perspect. Med., 2011). γ-Secretase is a large complex consisting of at least four different integral proteins, one of which is presenilin and has been identified as the catalytic component that harbors the catalytic aspartates (De Strooper, Bart et al., "*Presenilins and γ-Secretase: Structure, Function, and Role in Alzheimer's Disease.* "Cold Spring Harbor Perspect. Med. 2012; 2:a006304). Presenilin 1 and 2 were first discovered as sites of missense mutations responsible for early-onset Alzheimer's disease. The encoded multipass membrane proteins were subsequently found to be the catalytic components of γ-secretases, membrane-embedded aspartyl protease complexes responsible for generating the carboxyl terminus of the amyloid beta protein from the amyloid protein precursor. (De Strooper, Bart et al.; 2012). Accordingly, targeting the γ-secretase complex for drug discovery has become a main focus of Alzheimer's disease research.

The compounds of the present invention are believed to be γ-secretase modulators, which modulate the γ-secretase complex such that longer pathogenic Aβ peptides (i.e., Aβ42) are reduced and shorter Aβ species (i.e., Aβ37 and/or Aβ38) are increased. γ-Secretase modulators can be used for treating conditions or diseases of the central nervous system involving the γ-secretase complex, such as Niemann-Pick disease type C; neurological disorders (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, myoclonus, dystonia, delirium, Pick's disease, Creutzfeldt-Jacob disease, HIV disease, Gilles de la Tourette's syndrome, epilepsy, and mild cognitive impairment); tardive dyskinesia; muscular spasms and disorders associated with muscular spasticity or weakness including tremors; mental deficiency (including spasticity, Down's syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorders (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, premenstrual syndrome (PMS), premenstrual dysphoric disorder (PDD), and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye; tinnitus, hearing impairment and loss; and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of the present invention or a pharmaceutically acceptable salt thereof.

In certain embodiments, the compounds of the present invention can be utilized for treating a neurological disorder (such as migraine; epilepsy; Alzheimer's disease; Parkinson's disease; Niemann Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of the invention or pharmaceutically acceptable salt thereof.

Compounds of the present invention may also be useful for improving memory (both short term and long term) and learning ability.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV and that terminology and classification systems evolve with medical scientific progress.

Formulations

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a γ-secretase modulator compound as provided by the compounds of the invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as $Aβ_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis(4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g. ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), prednisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRI DOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-aminobutyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenyl]cyclobutanecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINO- MIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H,1'H-2,2'-bipyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (L-deprenyl, ELDEPRYL, ZELAPAR), desmethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazid (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, 2,3,4,9-tetrahydro-1H-carbazol-3-one oxime, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742), (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilast, roflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxy}methyl)quinoline (PF-2545920), and SCH-1518291, and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS- 782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER (N$^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A (5-HT$_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT$_{2c}$) receptor agonists, such as vabicaserin, and zicronapine;

(xxxv) serotonin (5-hydroxytryptamine) 4 (5-HT$_4$) receptor agonists, such as PRX-03140 (Epix);

(xxxvi) serotonin (5-hydroxytryptamine) 6 (5-HT$_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, and N-{(3S,4S)-4-[4-(5-cyanothiophen-2-yl)phenoxy] tetrahydrofuran-3-yl}propane-2-sulfonamide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The compounds of the present invention, or their pharmaceutically acceptable salts, may be prepared by the methods described below, together with synthetic methods known in the art of organic chemistry, or modifications and derivatizations that are familiar to those of ordinary skill in the art. The starting materials used herein are commercially available or may be prepared by routine methods known in the art [such as those methods disclosed in standard reference books such as the Compendium of Organic Synthetic Methods, Vol. I-XII (published by Wiley-Interscience)]. Preferred methods include, but are not limited to, those described below.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of the present invention, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Schemes

When intermediates used to synthesize compounds of the present invention incorporate a basic center, their suitable acid addition salts may be employed in synthetic pathways. Such suitable addition salts include but are not limited to those derived from inorganic acids, such as hydrochloric, hydrobromic, hydrofluoric, hydroiodic, boric, fluoroboric, phosphoric, nitric, carbonic, and sulfuric acids, and organic acids such as acetic, benzenesulfonic, benzoic, ethanesulfonic, fumaric, lactic, maleic, methanesulfonic, trifluoromethanesulfonic, succinic, toluenesulfonic, and trifluoroacetic acids. Suitable organic acids generally include but are not limited to aliphatic, cycloaliphatic, aromatic, aralphatic, heterocyclic, carboxylic, and sulfonic classes of organic acids.

Specific examples of suitable organic acids include but are not limited to acetate, trifluoroacetate, formate, propionate, succinate, lactate, maleate, fumarate, benzoate, p-hydroxybenzoate, phenylacetate, mandelate, methanesulfonate, ethanesulfonate, benzenesulfonate, toluenesulfonate, adipate, butyrate, camphorate, cyclopentanepropionate, dodecylsulfate, heptanoate, hexanoate, nicotinate, 2-naphthalenesulfonate, oxalate, 3-phenylpropionate, pivalate, and undecanoate.

Furthermore, where intermediates used to prepare compounds of the invention carry an acidic moiety, suitable salts thereof may be employed for synthesis. Such salts include alkali metal salts, e.g., lithium, sodium, or potassium salts; alkaline earth metal salts, e.g., calcium or magnesium salts; and salts formed with suitable organic ligands such as amines or quaternary ammonium cations. Organic salts of such acidic intermediates may be made from primary, secondary or tertiary amines such as methylamine, diethylamine, ethylenediamine or trimethylamine. Quaternary amines may be prepared by reaction of tertiary amines with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), arylalkyl halides (e.g., benzyl and phenethyl bromides), and others.

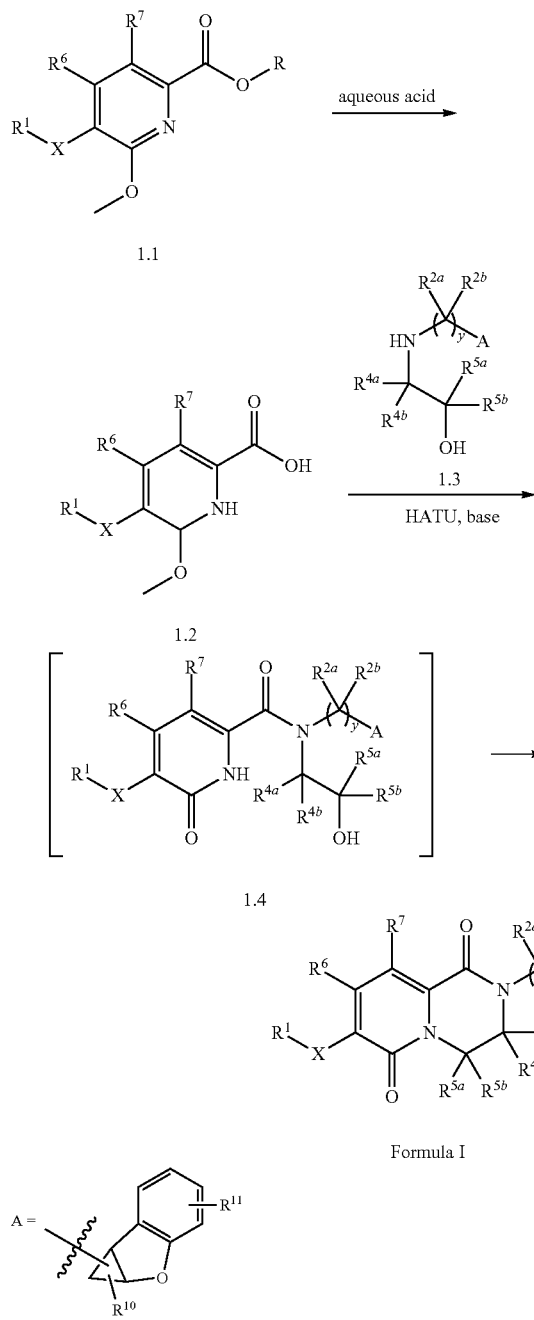

of a compound of Formula 1.1, wherein $R^1$ is typically a ($C_1$-$C_6$)alkyl such as methyl, ethyl, tert-butyl and the like, is heated in the presence of an aqueous acid such as hydrochloric acid to furnish the corresponding pyridinone acid of Formula 1.2. During this initial step, the $R^1$—X, $R^6$ and $R^7$ substituents of Formula 1.1 should be represented by the same moieties as are desired in the final product, or a protected variation thereof. For example, the final product of Example 1 can be prepared utilizing reaction Scheme 1, where $R^1$ is represented by methyl, X is represented by imidazolyl, and $R^6$ and $R^7$ of Formula 1.1 are each represented by hydrogen.

Next, the acid intermediate of Formula 1.2 is subjected to an amide coupling and in situ cyclization reaction with an amino alcohol of Formula 1.3 using an appropriate amide coupling reagent such as HATU [O-(7-azabenzotriazol-1-yl)-N,N,N',N'-tetramethyluronium hexafluorophosphate]. The reaction is carried out in the presence of a suitable base such as N,N-diisopropylethylamine, and in a solvent such as dichloromethane or N,N-dimethylformamide. During this step, y of Formula 1.3 should be represented by an integer as desired in the final product, and the A, $R^{2a}$, $R^{2b}$, $R^{4a}$, $R^{4b}$, $R^{5a}$, $R^{5b}$ substituents should be represented by the same moieties as are desired in the final product, or a protected variation thereof. For example, the final product of Example 1 can be prepared utilizing reaction Scheme 1, where $R^{2a}$, $R^{2b}$, $R^{4a}$, $R^{4b}$, $R^{5a}$, and $R^{5b}$ are each hydrogen, y is 1, and A represents 5-(trifluoromethyl)-1,1a-dihydro-6bH-cyclopropa[b][1]benzofuran-6b-yl.

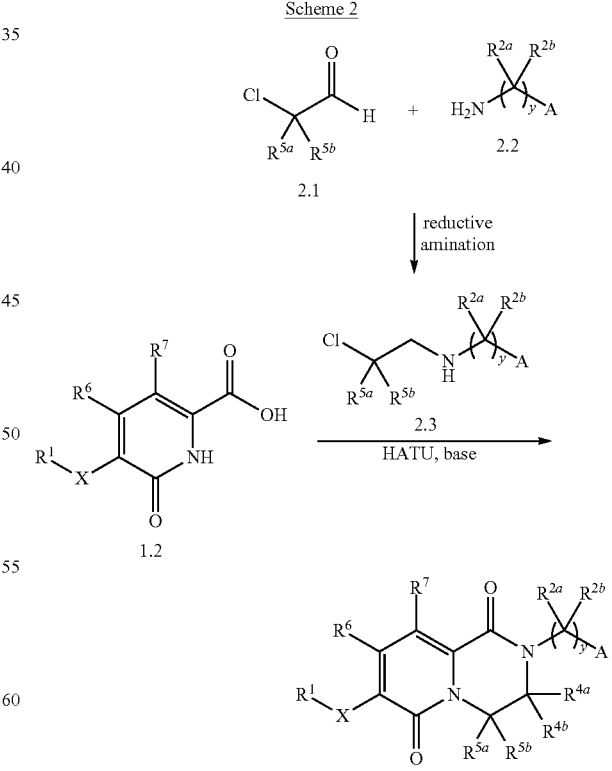

Scheme 1 above illustrates one synthetic sequence for the preparation of compounds depicted by Formula I. In the initial step of the synthesis, as depicted, an appropriate ester

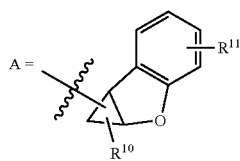

Scheme 2 illustrates another synthetic sequence for the preparation of compounds of Formula I. Reaction of a chloroaldehyde of Formula 2.1 and an amine of Formula 2.2

2.3, the acid of Formula 1.2 (Scheme 1), and a base such as N,N-diisopropylethylamine with a suitable amide coupling reagent such as BOP-Cl [bis(2-oxo-3-oxazolidinyl)phosphonic chloride], T3P [2,4,6-tripropyl-1,3,5,2,4,6-trioxatriphosphinane 2,4,6-trioxide] or HATU (preferably HATU) in a solvent such as dichloromethane. During this step the $R^1$—X, $R^6$ and $R^7$ substituents of Formula 1.2 should be represented by the same moieties as are desired in the final product, or a protected variation thereof.

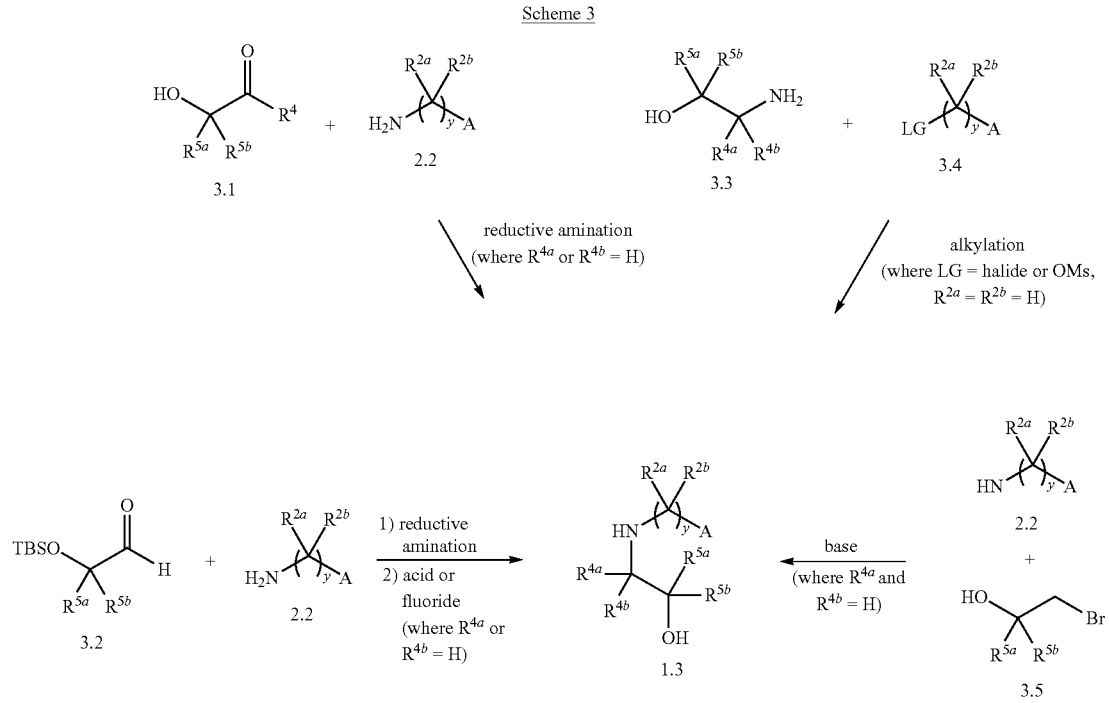

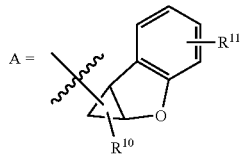

using one of many reductive amination protocols known to those skilled in the art provides the chloroalkylamine of Formula 2.3. For example, this reaction may be carried out by using a reducing agent such as sodium triacetoxyborohydride in a suitable solvent such as methanol. During this step, y of the amine of Formula 2.2 should be represented by an integer as desired in the final product. The $R^{5a}$ and $R^{5b}$ substituents of Formula 2.1 and the A, $R^{2a}$, and $R^{2b}$ substituents of the amine of Formula 2.2 should also be represented by the same moieties as are desired in the final product, or a protected variation thereof.

Following purification, the resultant chloroalkylamine of Formula 2.3 may be isolated and stored as its hydrochloride salt. The final compound of Formula I may then be prepared by treating a mixture of the chloroalkylamine of Formula Scheme 3 represents several synthetic sequences for the preparation of the aminoalcohol of Formula 1.3, which can readily be envisioned and developed by one skilled in the art. For example, the aminoalcohol of Formula 1.3 may be prepared by carrying out a reductive amination of a ketone of Formula 3.1 with an amine of Formula 2.2 using one of many procedures well known to those skilled in the art.

Another method involves reductive amination of an aldehyde of Formula 3.2 with an amine of Formula 2.2, followed by removal of the tert-butyl(dimethyl)silyl (TBS) protecting group by using a suitable procedure including treatment with methanolic hydrogen chloride or tetrabutylammonium fluoride.

Another method for the synthesis of an aminoalcohol of Formula 1.3 involves alkylation of an amine of Formula 3.3 with a halide or mesylate of Formula 3.4.

Yet another method involves alkylation of an amine of Formula 2.2 with a bromoalcohol of Formula 3.5. Methods of synthesis for various amines of Formula 2.2, as well as alternative methods of preparation of aminoalcohols of Formula 1.3, are exemplified in the Experimental Section.

A person skilled in the art, utilizing these disclosures in combination with what is commonly known in the art, may further generalize those syntheses to allow access to a wide variety of amines of Formula 2.2 and aminoalcohols of Formula 1.3, including but not limited to variations in which y is represented by an integer as desired in the final product, and A, $R^{2a}$, $R^{2b}$, $R^{4a}$, $R^{4b}$, $R^{5a}$, and $R^{5b}$ substituents are represented by the same moieties as are desired in the final product, or a protected variation thereof.

Scheme 4

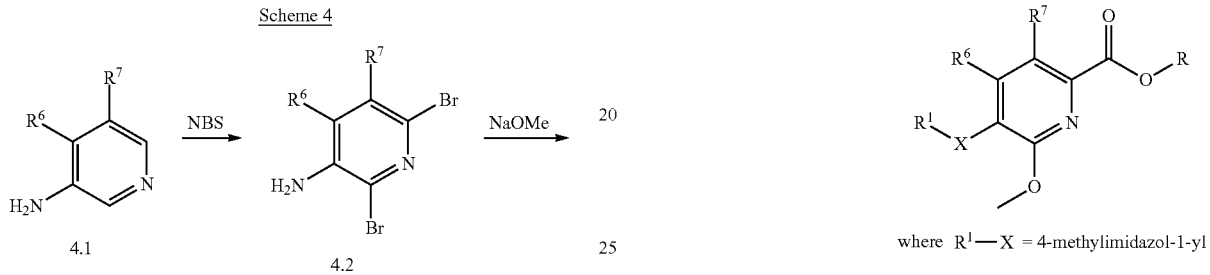

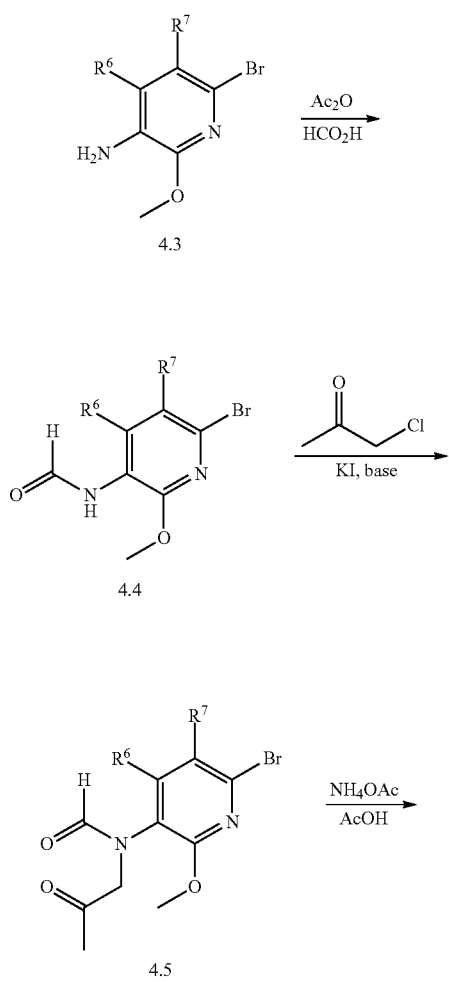

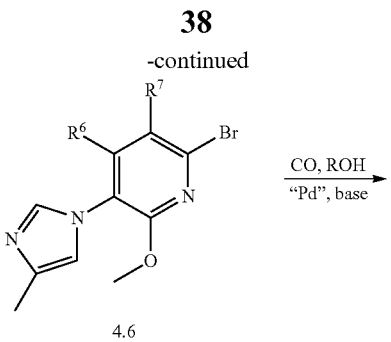

Scheme 4 illustrates one synthetic sequence for the preparation of compounds of Formula 1.1 where $R^1$—X=4-methylimidazol-1-yl or 3-methyltriazol-1-yl. A 3-aminopyridine compound of Formula 4.1 is brominated using N-bromosuccinimide (NBS) in a solvent such as a mixture of DMSO and water. During this initial step the $R^6$ and $R^7$ substituents are represented by the same moieties as are desired in the final product, or a protected variation thereof. The resulting intermediate of Formula 4.2 is then heated with sodium methoxide in a suitable solvent such as 1,4-dioxane to afford the methoxy compound of Formula 4.3. The intermediate of Formula 4.3 is then treated with a mixture of acetic anhydride and formic acid to afford a formamide of Formula 4.4, which is alkylated with chloroacetone in the presence of potassium iodide and a base such as cesium carbonate in a suitable solvent such as N,N-dimethylformamide. The resulting intermediate of Formula 4.5 is then heated in the presence of $NH_4OAc$ in acetic acid to furnish the imidazole derivative of Formula 4.6. Finally, the compound of Formula 1.1 can be prepared by subjecting the intermediate of Formula 4.6 to a carbonylation/esterification reaction. This transformation may be carried out by heating a solution of the bromo compound of Formula 4.6 and a base such as triethylamine in an appropriate alcohol solvent ("ROH"), wherein R is typically a $(C_1-C_6)$alkyl such as methyl or ethyl, under an atmosphere of CO in the presence of a suitable palladium catalyst such as Pd(dppf)$Cl_2$.dichloromethane {[1,1'-bis(diphenylphosphino)ferrocene] dichloropalladium(II), dichloromethane complex} to provide the ester of Formula 1.1.

Scheme 5

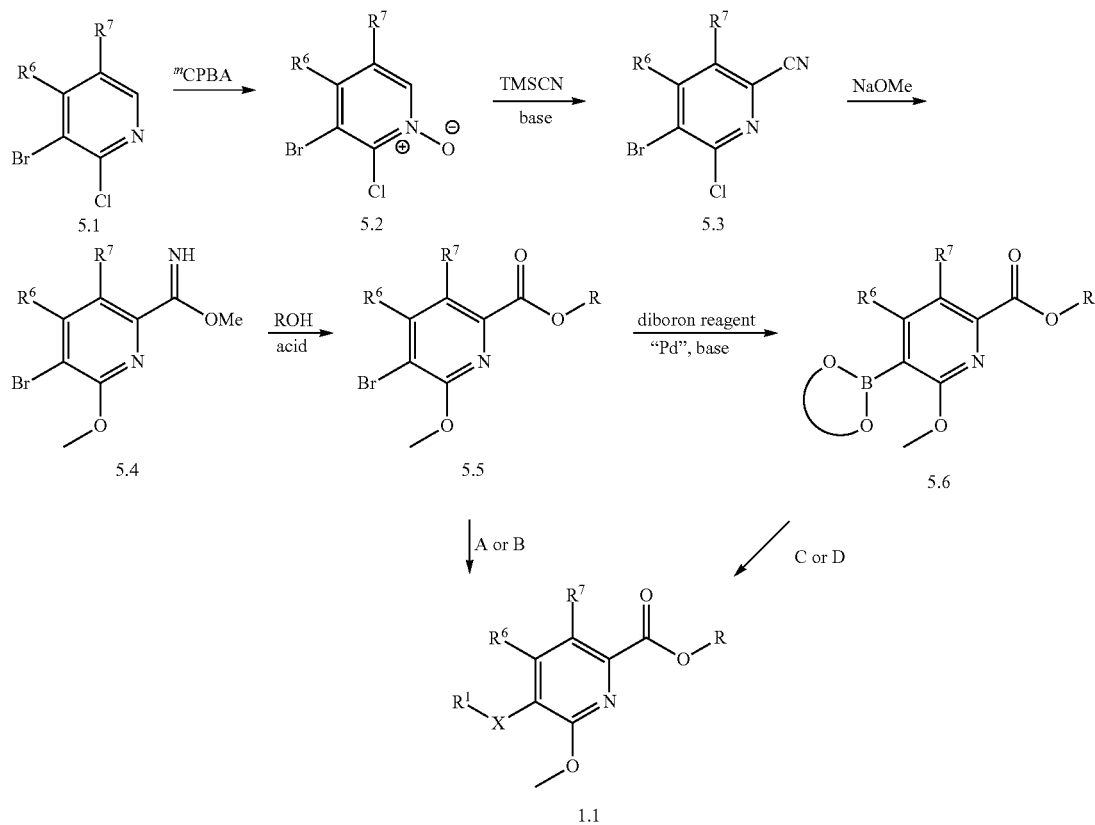

A) Suzuki coupling: R¹X—B(OH)₂, "Pd", base

B) CH-activation: "Pd", 5-membered heteroaryls such as 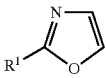
5.7 provide compounds of Formula 1.1 wherein R¹—X— is 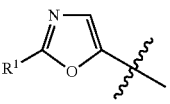

C) Chan-Lam coupling: Cu₂O or Cu(OAc)₂, 5-membered heteroaryls such as 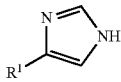 
5.8    5.9 provide compounds of Formula 1.1 wherein R¹—X— is 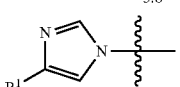

D) Suzuki coupling R¹X—Br, "Pd", base where X = a 5- to 6-membered heteroaryl ring Scheme 5 depicts alternative synthetic sequences for the preparation of compounds of Formula 1.1. In a first step, a pyridyl derivative of Formula 5.1 is oxidized with an oxidizing agent such as mCPBA [3-chloroperoxybenzoic acid] in a suitable solvent such as dichloroethane to afford the corresponding N-oxide of Formula 5.2. During this initial step the R⁶ and R⁷ substituents of Formula 5.1 are represented by the same moieties as are desired in the final product, or a protected variation thereof. The N-oxide of Formula 5.2 is then heated in the presence of TMSCN [trimethylsilyl cyanide] and a base such as triethylamine in a solvent such as acetonitrile to afford the nitrile intermediate of Formula 5.3. The corresponding ester may then be prepared from Formula 5.3 in two steps by subjecting Formula 5.3 to sodium methoxide in a solvent such as THF, followed by treatment with an appropriate alcohol solvent ("ROH"), wherein R is typically a (C₁-C₆)alkyl such as methyl, ethyl and the like, and an acid such as hydrochloric acid. The ester of Formula 5.5 is a versatile intermediate that allows introduction of a variety of heterocycles R¹—X. For example, Formula 5.5 may be subjected to a Suzuki coupling with a heteroarylboronic acid, using methods well known to those skilled in the art [see *Tetrahedron* 2002, 58, 9633-9695]. Alternatively, the compound of Formula 5.5 may be coupled to a heterocycle X using a direct arylation approach [see D. Lapointe et al., *J. Org. Chem.* 2011, 76, 749-759, and references therein]. For example, the compound of Formula 5.5 may be coupled to 2-methyl-1,3-oxazole [Formula 5.7 where $R^1$=Me] by heating in the presence of a suitable palladium catalyst such as allylpalladium chloride dimer and a base such as potassium carbonate in a solvent such as 1,4-dioxane, to afford the intermediate of Formula 1.1 where $R^1$—X=2-methyl-1,3-oxazol-5-yl.

Alternatively, the compound of Formula 5.5 may be converted to the corresponding boronate of Formula 5.6, using a palladium-catalyzed cross coupling with a diboron reagent such as 5,5,5',5'-tetramethyl-2,2'-bi-1,3,2-dioxaborinane in the presence of potassium acetate and a palladium catalyst such as Pd(dppf)Cl$_2$.dichloromethane in a solvent such as 1,4-dioxane. The resulting boronate intermediate of Formula 5.6 can in turn be subjected to a Suzuki coupling with a heteroaryl halide to afford the final compound of Formula 1.1. Another method for the introduction of a heterocycle X involves the use of a Chan-Lam coupling [see *Tetrahedron Lett.* 2003, 44, 3863-3865, and *Synthesis* 2008, 5, 795-799]. For example, the boronate of Formula 5.6 may be coupled to a substituted imidazole of Formula 5.8 or to a substituted triazole of Formula 5.9. by heating with a suitable copper source such as copper(I) oxide or copper(II) acetate in a solvent such as methanol in the presence of air to afford the intermediate of Formula 1.1 where X=imidazol-1-yl or triazol-1-yl.

Scheme 6

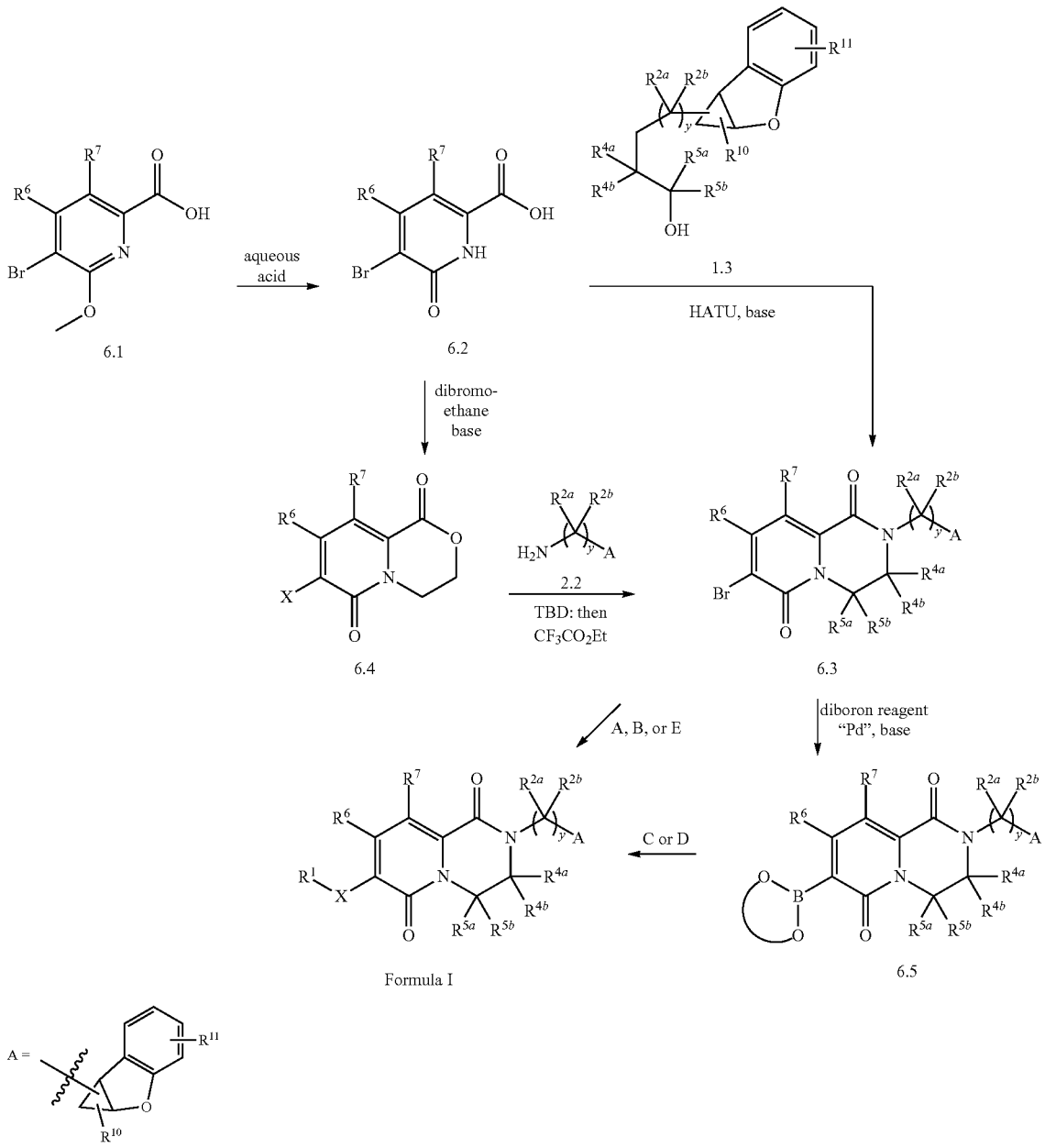

A) Suzuki coupling: R¹X—B(OH)₂, "Pd", base

B) CH-activation: "Pd", 5-membered heteroaryls such as 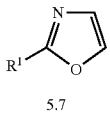
5.7 provide compounds of Formula 1 wherein R¹—X— is 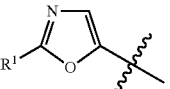

C) Chan-Lam coupling: Cu₂O or Cu(OAc)₂, 5-membered heteroaryls such as 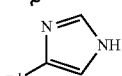
5.8 provide compounds of Formula 1 wherein R¹—X— is 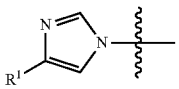

D) Suzuki coupling R¹X—Br, "Pd", base where X = a 5- to 6-membered heteroaryl ring E) "Pd", and heteroaryl such as 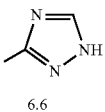 or 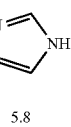
6.6    5.8 provide compounds of Formula 1 wherein R¹—X— is 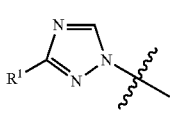 or 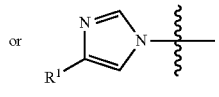

Scheme 6 illustrates yet another set of synthetic sequences for the preparation of compounds of Formula I. Heating an intermediate of Formula 6.1 in an acid such as hydrochloric acid affords the pyridinone acid intermediate of Formula 6.2. During this initial step, the $R^6$ and $R^7$ substituents of Formula 6.1 are represented by the same moieties as are desired in the final product, or a protected variation thereof. Next, the acid of Formula 6.2 may be subjected to a coupling/cyclization reaction with an aminoalcohol of Formula 1.3 (Scheme 1) to afford an intermediate of Formula 6.3 using chemistry described in Scheme 1. During this step, y of Formula 1.3 should be represented by an integer as desired in the final product, and the $R^{2a}$, $R^{2b}$, $R^{4a}$, $R^{4b}$, $R^{5a}$, $R^{5b}$, $R^{10}$ and $R^{11}$ substituents should be represented by the same moieties as are desired in the final product, or a protected variation thereof.

An alternative synthesis of the intermediate of Formula 6.3 involves heating a mixture of the intermediate of Formula 6.2, dibromoethane, and a base such as cesium carbonate in a solvent such as N,N-dimethylformamide to afford a lactone of Formula 6.4. During this initial step, the $R^6$ and $R^7$ substituents of Formula 6.1 are represented by the same moieties as are desired in the final product, or a protected variation thereof. The resultant intermediate of Formula 6.3 may then be subjected to an amidation reaction with an amine of Formula 2.2 (Scheme 2). This transformation may be carried using a number of different conditions. For example, the lactone of Formula 6.2 and the amine of Formula 2.2 may be heated in the presence of a base such as 1,3,4,6,7,8-hexahydro-2H-pyrimido[1,2-a]pyrimidine (TBD) in a solvent such as N,N-dimethylformamide, followed by addition of ethyl trifluoroacetate to afford the lactam of Formula 6.3 wherein $R^{4a}$=$R^{4b}$=$R^{5a}$=$R^{5b}$=H. During the amidation step, y of Formula 2.2 should be represented by an integer as desired in the final product.

The final compound, Formula I, may then be formed directly from Formula 6.3 or via the boronate of Formula 6.5, using the strategies discussed in Scheme 5. Alternatively, compounds of Formula I where heterocycle X is linked to the pyridinone ring via a C—N bond may be formed by palladium-catalyzed cross coupling. For example, the triazole of Formula 6.6 may be coupled to Formula 6.3 by heating in the presence of a palladium catalyst such as tris(dibenzylideneacetone)dipalladium(0) and a suitable ligand such as di-tert-butyl[3,4,5,6-tetramethyl-2',4',6'-tri(propan-2-yl)biphenyl-2-yl]phosphane and base such as potassium phosphate in a solvent such as toluene to afford the final compound of Formula I where X=1,2,4-triazol-1-yl.

Scheme 7

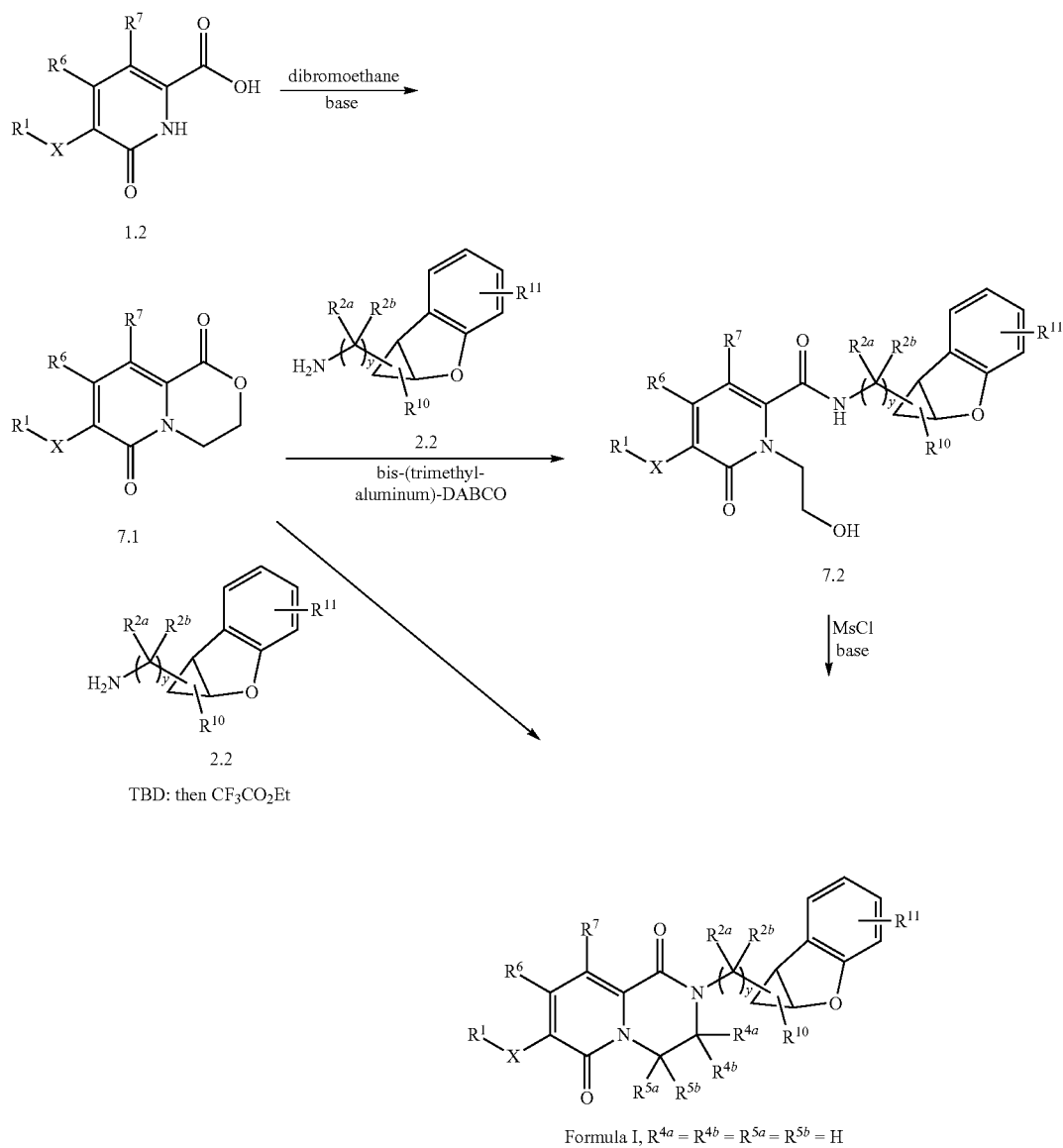

Scheme 7 illustrates another synthetic sequence for the preparation of compounds of Formula I, where $R^{4a}=R^{4b}=R^{5a}=R^{5b}=H$. The method involves heating a mixture of a compound of Formula 1.2 (Scheme 1), dibromoethane, and a base such as cesium carbonate in a solvent such as N,N-dimethylformamide to afford the lactone intermediate of Formula 7.1. During this initial step, the $R^1$—X, $R^6$ and $R^7$ substituents of Formula 1.2 are represented by the same moieties as are desired in the final product, or a protected variation thereof. The lactone of Formula 7.1 may then be reacted with an amine of Formula 2.2 (from Scheme 2) in the presence of a reagent such as DIBAL (diisobutylaluminum hydride) or bis(trimethylaluminum)-1,4-diazabicyclo[2.2.2]octane adduct in a solvent such as THF to afford the amide alcohol of Formula 7.2. During this step, y of Formula 2.2 should be represented by an integer as desired in the final product, and the $R^{2a}$, $R^{2b}$, $R^{10}$ and $R^{11}$ substituents should be represented by the same moieties as are desired in the final product, or a protected variation thereof. The intermediate of Formula 7.2 may be reacted with methanesulfonyl chloride in the presence of a base such as triethylamine in a solvent such as THF, followed by treatment with a base such as 1,3,4,6,7,8-hexahydro-2H-pyrimido[1,2-a]pyrimidine (TBD) to afford the compound of Formula I wherein $R^{4a}=R^{4b}=R^{5a}=R^{5b}=H$. Alternatively, the ring closure may be carried out in a stepwise fashion by first converting the alcohol of Formula 7.2 into the corresponding chloride by treatment with thionyl chloride, followed by deprotonation of the amide NH with a suitable base such as lithium bis(trimethylsilyl)amide to afford the final compound of Formula I. Alternatively, a solution of lactam 7.1 and amine 2.2 in N,N-dimethylformamide may be treated with 1,3,4,6,7,8-hexahydro-2H-pyrimido[1,2-a]pyrimidine (TBD) in N,N-dimethylformamide to form intermediate 7.2, which is then directly converted to Formula I in the same pot via addition of ethyl trifluoroacetate.

Scheme 8

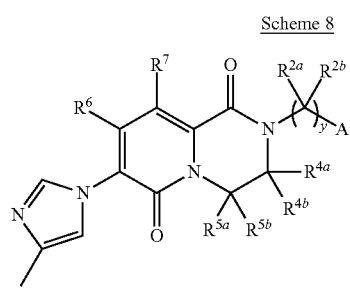

Formula I
where X = imidazol-1-yl and
R¹ = methyl microsomes or hepatocytes

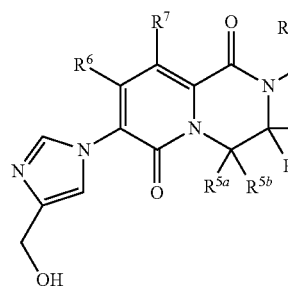

Formula I
where X = imidazol-1-yl and
R¹ = hydroxymethyl

Compounds of Formula I where X is imidazolyl and R¹ is hydroxymethyl may be prepared in one step from the corresponding compound of Formula I where X is imidazolyl and R¹ is methyl. This transformation can be carried out via incubation with microsomes from a suitable species such as monkey in the presence of magnesium chloride and nicotinamide adenine dinucleotide phosphate (NADPH) in a suitable buffer such as potassium phosphate (pH 7.4).

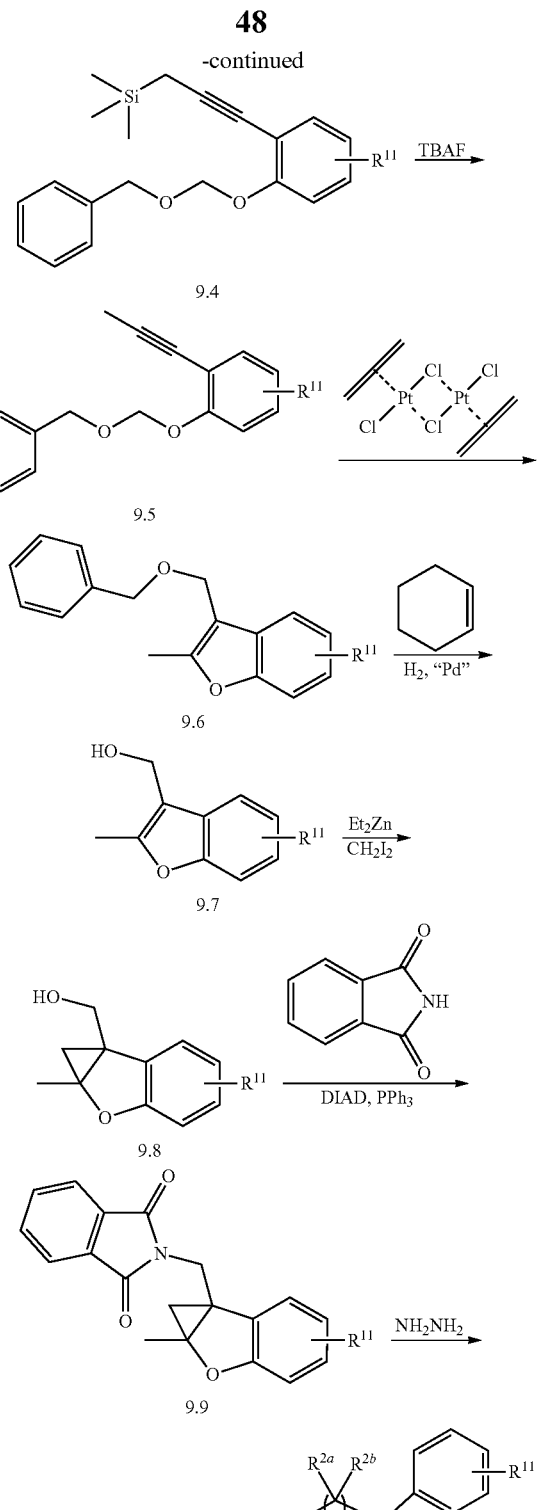

A number of routes can be envisioned to access intermediates of Formula 2.2, where $R^{2a}=R^{2b}=H$, $R^{10}=$methyl, y=1, $R^{10}$ is connected to the quaternary carbon atom adjacent to the benzofuran oxygen atom, and the aminomethyl substituent is connected to the benzylic position. One approach commences with bromination or iodination of a phenol of Formula 9.1 using a suitable halogenating reagent such as N-bromosuccinamide (NBS) or N-iodosuccinamide (NIS). During this step, the $R^{11}$ substituent should be represented by the same moiety as is desired in the final product, or a protected variation thereof. The resultant phenol intermediate of Formula 9.2 is then reacted with benzyl chloromethyl ether in the presence of a suitable base such as potassium carbonate and in a solvent such as acetonitrile to afford an intermediate of Formula 9.3. This compound is then subjected to a Sonogashira coupling with trimethyl(prop-2-yn-1-yl)silane using a copper source such as copper(I) iodide and a palladium catalyst such as dichlorobis(triphenylphosphine)palladium(II) in triethylamine. The trimethylsilyl protecting group is subsequently removed using a fluoride source such as tetra-N-butylammonium fluoride (TBAF) in a solvent such as tetrahydrofuran to afford an intermediate of Formula 9.5. This compound can then be heated in the presence of a platinum catalyst such as di-p-chloro-dichlorobis(ethylene)diplatinum(III) in a solvent such as toluene to afford benzofuran intermediate 9.6. The benzyl protecting group is then removed via hydrogenolysis using palladium hydroxide on carbon in cyclohexene. Cyclopropanation of the benzofuran 2,3-double bond can be carried under a number of conditions such as the Simmons-Smith reaction. For example, the intermediate of Formula 9.7 is treated with diethylzinc and diiodomethane in a suitable solvent such as dichloromethane to afford the cyclopropyl benzofuran alcohol intermediate of Formula 9.8. The primary alcohol in the intermediate of Formula 9.8 may then be converted to the corresponding primary amine using a number of procedures well known to those skilled in the art. For example, this functional group interconversion can be accomplished via a Mitsunobu reaction with phthalimide followed by deprotection using a reagent such as hydrazine monohydrate in a solvent such as dichloromethane and methanol to afford the desired amine of Formula 2.2.

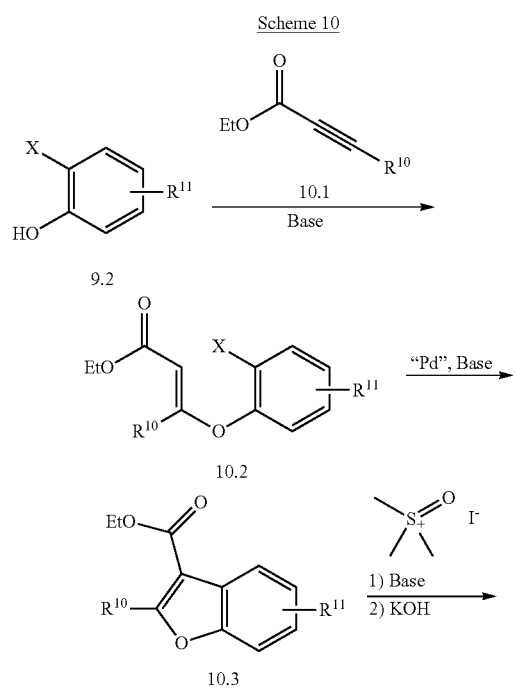

X = Br or I

Scheme 10 displays an alternative synthetic route to intermediates of Formula 2.2 where $R^{2a}$=$R^{2b}$=H, y=1, $R^{10}$ is connected to the quaternary carbon atom adjacent to the benzofuran oxygen atom, and the aminomethyl substituent is connected to the benzylic position. In this approach, the phenol of Formula 9.2 undergoes a 1,4-addition to an alkyne derivative of Formula 10.1 in the presence of a base such as potassium carbonate in a solvent such as acetonitrile. During this step, the $R^{10}$ and $R^{11}$ substituents should be represented by the same moiety as is desired in the final product, or a protected variation thereof. The resulting compound of Formula 10.2 is then subjected to an intramolecular Heck reaction using a suitable palladium catalyst such as bis(tri-tert-butylphosphine)palladium(0) in the presence of a base such as triethylamine in a solvent such as acetonitrile. The resultant benzofuran intermediate of Formula 10.3 is then subjected to cyclopropanation using trimethylsulfoxonium iodide in dimethyl sulfoxide in the presence of a base such as potassium tert-butoxide. The ester is immediately hydrolyzed to the corresponding acid of Formula 10.4 using a suitable base such as potassium hydroxide or potassium tert-butoxide. The final step in the sequence involves conversion of the carboxylic acid of Formula 10.4 to the amine of Formula 2.2. This functional group interconversion can be carried out under a number of different conditions known to those skilled in the art. For example, amide coupling of acid 10.4 with ammonium hydroxide and a coupling reagent such as 1,1'-carbonyldiimidazole delivers the primary amide of Formula 10.5, which is subsequently reduced using a suitable reducing agent such as bis(2-methoxyethoxy)aluminum hydride in a solvent such as toluene.

EXPERIMENTAL PROCEDURES AND WORKING EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

7-(4-Methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione (1)

(The compound of Example 1 was previously disclosed in U.S. Provisional Patent Application No. 61/973,436, filed on Apr. 1, 2014 as Example 19. While this compound is not encompassed by the claims of the present application, it is being exemplified herein to provide additional synthetic methodology).

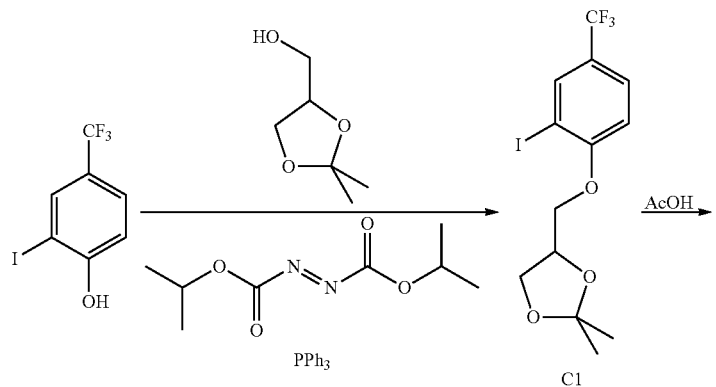

-continued
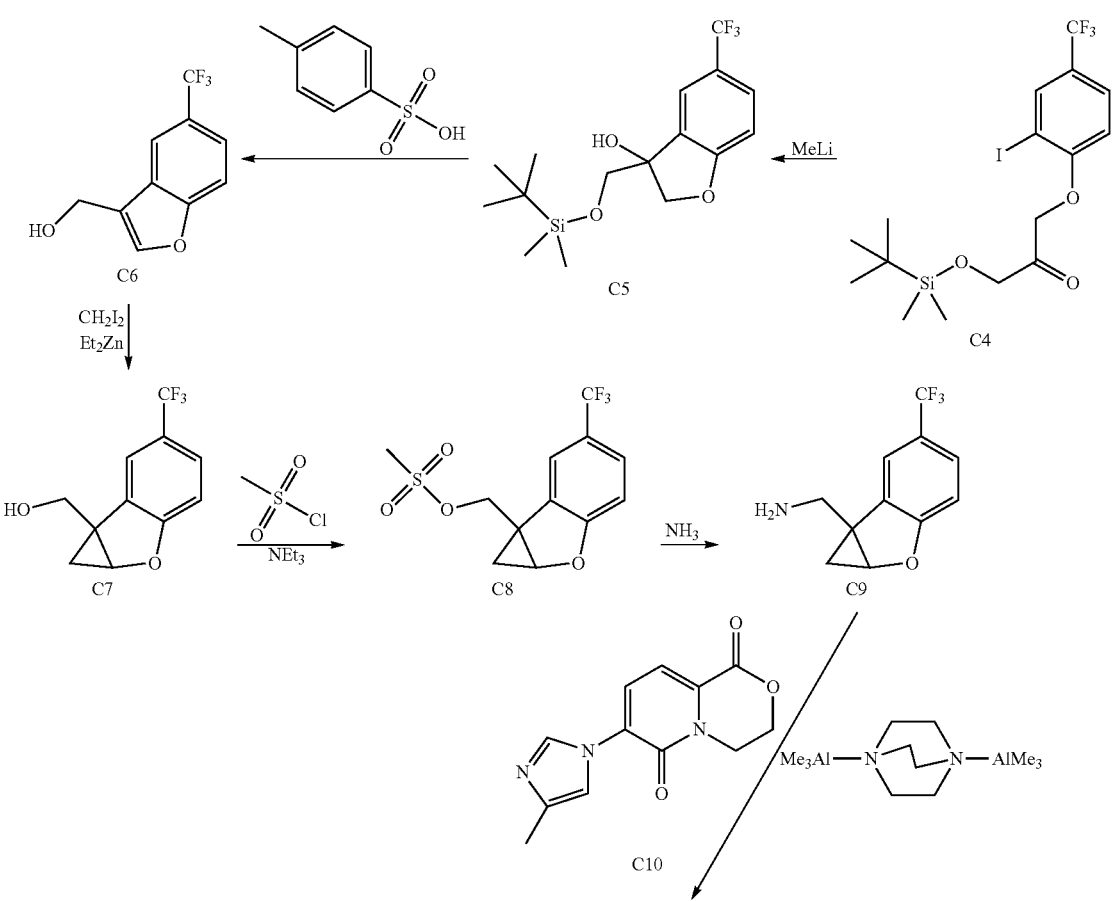

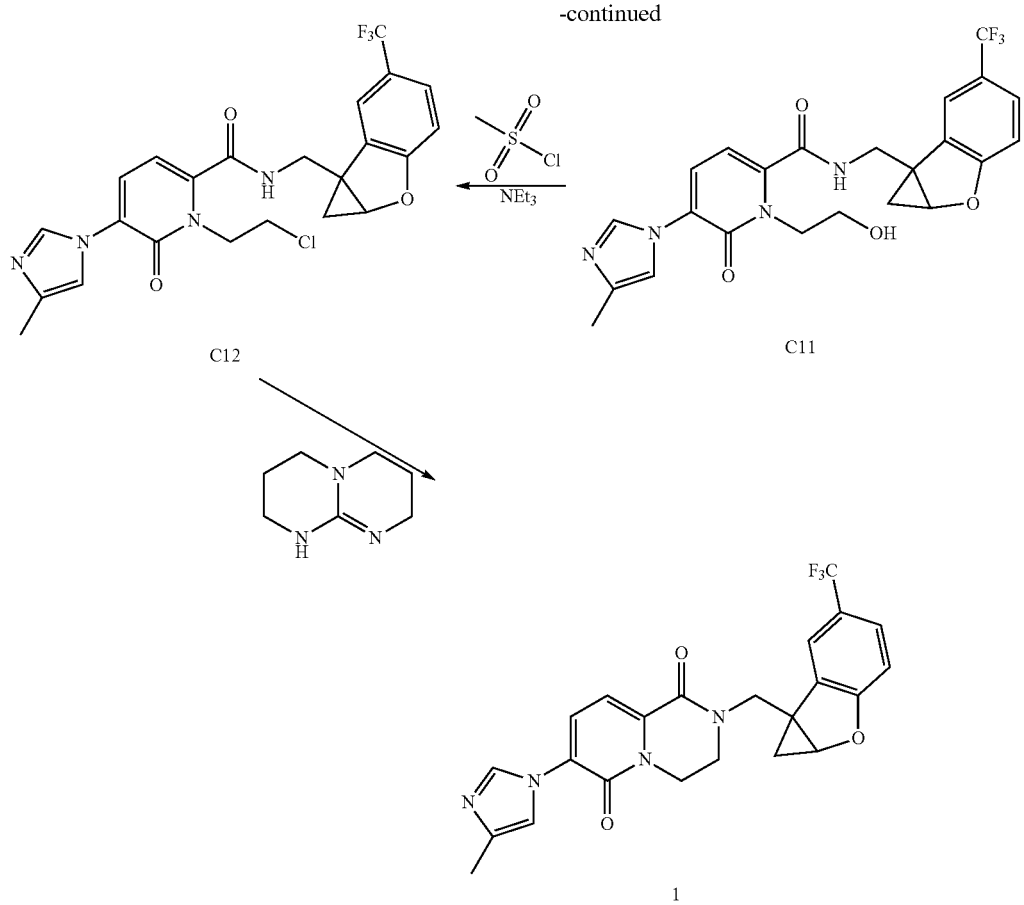

Step 1. Synthesis of 4-{[2-iodo-4-(trifluoromethyl)phenoxy]methyl}-2,2-dimethyl-1,3-dioxolane (C1)

Diisopropyl azodicarboxylate (8.2 mL, 42 mmol) was added slowly, in a drop-wise manner, to a 0° C. solution of (2,2-dimethyl-1,3-dioxolan-4-yl)methanol (5.5 g, 42 mmol) and triphenylphosphine (10.9 g, 42 mmol) in tetrahydrofuran (80 mL). 2-Iodo-4-(trifluoromethyl)phenol (8.0 g, 28 mmol) was slowly added to the 0° C. reaction mixture, which was then allowed to stir at room temperature for 6 hours. After removal of solvent in vacuo, the residue was partitioned between water and ethyl acetate, and the organic layer was washed with water, dried over sodium sulfate, filtered, and concentrated under reduced pressure. Silica gel chromatography (Eluent: 10% ethyl acetate in hexane) afforded the product as a light yellow liquid. Yield: 6.5 g, 16 mmol, 57%. $^1$H NMR (400 MHz, CDCl$_3$) δ 8.02 (br s, 1H), 7.58 (br d, J=8.6 Hz, 1H), 6.88 (d, J=8.6 Hz, 1H), 4.48-4.56 (m, 1H), 4.23 (dd, J=8.4, 6.2 Hz, 1H), 4.18 (dd, half of ABX pattern, J=9.5, 4.2 Hz, 1H), 4.04-4.11 (m, 2H), 1.49 (s, 3H), 1.42 (s, 3H).

Step 2. Synthesis of 3-[2-iodo-4-(trifluoromethyl)phenoxy]propane-1,2-diol (C2)

A solution of C1 (6.5 g, 16 mmol) in acetic acid (3.2 mL, 56 mmol) and water (0.29 mL, 16 mmol) was stirred at room temperature for 18 hours, whereupon it was concentrated under reduced pressure. The residue was washed with pentane, and the resulting solid was taken into the following step without further purification. Yield: 5.25 g, 14.5 mmol, 91%. GCMS m/z 362 [M$^+$]. $^1$H NMR (400 MHz, CDCl$_3$) δ 8.01-8.04 (m, 1H), 7.60 (br d, J=8.6 Hz, 1H), 6.89 (d, J=8.6 Hz, 1H), 4.13-4.23 (m, 3H), 3.83-3.97 (m, 2H), 2.71 (d, J=4.5 Hz, 1H), 2.05 (dd, J=6.2, 6.0 Hz, 1H).

Step 3. Synthesis of 1-{[tert-butyl(dimethyl)silyl]oxy}-3-[2-iodo-4-(trifluoromethyl)phenoxy]propan-2-ol (C3)

To a solution of C2 (5.25 g, 14.5 mmol) in N,N-dimethylformamide (50 mL) was added imidazole (1.1 g, 16 mmol), followed by slow addition of tert-butyl(dimethyl)silyl chloride (2.4 g, 16 mmol). After 6 hours at room temperature, the reaction mixture was diluted with ice water and then extracted with ethyl acetate. The combined organic layers were dried over sodium sulfate, filtered, and concentrated in vacuo; silica gel chromatography (Eluent: 5% ethyl acetate in hexanes) provided the product as a light yellow liquid. Yield: 4.12 g, 8.65 mmol, 60%. NMR (400 MHz, CDCl$_3$) δ 8.01-8.03 (m, 1H), 7.58 (br d, J=8.6 Hz, 1H), 6.88 (d, J=8.6 Hz, 1H), 4.05-4.17 (m, 3H), 3.84-3.92 (m, 2H), 2.58 (d, J=5.8 Hz, 1H), 0.91 (s, 9H), 0.10 (s, 3H), 0.09 (s, 3H).

Step 4. Synthesis of 1-{[tert-butyl(dimethyl)silyl]oxy}-3-[2-iodo-4-(trifluoromethyl)phenoxy]propan-2-one (C4)

Dess-Martin periodinane [1,1,1-tris(acetyloxy)-1,1-dihydro-1,2-benziodoxol-3-(1H)-one; 11.0 g, 25.9 mmol] was added to a 0° C. solution of C3 (4.12 g, 8.65 mmol) in dichloromethane (40 mL), and the reaction mixture was stirred for 14 hours. Excess oxidant was removed via filtration through a pad of diatomaceous earth; the filtrate was diluted with water and extracted with dichloromethane. The combined organic layers were concentrated in vacuo, and the crude product was used in the following step without additional purification. Yield: 3.7 g, 7.8 mmol, 90%. $^1$H NMR (400 MHz, CDCl$_3$) δ 8.05-8.07 (m, 1H), 7.57 (br d, J=8.6 Hz, 1H), 6.70 (d, J=8.6 Hz, 1H), 4.94 (s, 2H), 4.59 (s, 2H), 0.96 (s, 9H), 0.15 (s, 6H).

Step 5. Synthesis of 3-({[tert-butyl(dimethyl)silyl] oxy}methyl)-5-(trifluoromethyl)-2,3-dihydro-1-benzofuran-3-ol (C5)

Methyllithium (1.6 M solution in diethyl ether, 9.2 mL, 15 mmol) was slowly added to a −78° C. solution of C4 (3.5 g, 7.4 mmol) in tetrahydrofuran (30 mL), and the reaction mixture was stirred at this temperature for 5 hours. Aqueous ammonium chloride solution was then slowly added, and the resulting mixture was extracted with ethyl acetate. The combined organic layers were dried over sodium sulfate, filtered, and concentrated in vacuo to provide the crude product (2.1 g), which was used directly in the next step. $^1$H NMR (400 MHz, CDCl$_3$), product peaks only: δ 7.62-7.65 (m, 1H), 7.51-7.55 (m, 1H), 6.91 (d, J=8.6 Hz, 1H), 4.49 (s, 2H), 3.84 (AB quartet, $J_{AB}$=9.8 Hz, $\Delta v_{AB}$=11.3 Hz, 2H), 0.94 (s, 9H), 0.12 (s, 3H), 0.10 (s, 3H).

Step 6. Synthesis of [5-(trifluoromethyl)-1-benzofuran-3-yl]methanol (C6)

An aqueous solution of p-toluenesulfonic acid (10%, 11 mL) was slowly added to a solution of C5 (from the previous step; 2.1 g, mmol) in acetone (20 mL), and the reaction mixture was allowed to stir at room temperature for 14 hours. Acetone was removed via concentration in vacuo, and the aqueous residue was extracted with ethyl acetate. The combined organic layers were dried over sodium sulfate, filtered, and concentrated under reduced pressure; silica gel chromatography (Eluent: 5% ethyl acetate in hexane) afforded the product (435 mg) as a light yellow liquid. Also isolated was the tert-butyl(dimethyl)silyl-protected derivative of C6; this was subjected to p-toluenesulfonic acid in a similar manner, providing an additional 150 mg of the product. Total yield: 585 mg, 2.71 mmol, 37% over two steps. $^1$H NMR (400 MHz, CDCl$_3$) δ 8.00 (br s, 1H), 7.73 (br s, 1H), 7.56-7.63 (m, 2H), 4.90 (br d, J=5.3 Hz, 2H), 1.68 (t, J=5.6 Hz, 1H).

Step 7. Synthesis of [5-(trifluoromethyl)-1,1a-dihydro-6bH-cyclopropa[b][1]benzofuran-6b-yl] methanol (C7)

To a 0° C. solution of C6 (100 mg, 0.46 mmol) in dichloromethane (10 mL) was added diiodomethane (744 mg, 2.78 mmol), followed by slow addition of diethylzinc (1 M solution in hexanes, 1.39 mL, 1.39 mmol) at the same temperature. The reaction mixture was allowed to slowly warm to room temperature, whereupon it was stirred for 3 hours. It was then quenched via addition of saturated sodium thiosulfate solution, and extracted with dichloromethane; the combined organic layers were washed with saturated aqueous sodium chloride solution, dried over sodium sulfate, filtered, and concentrated in vacuo. Silica gel chromatography (Gradient: 0% to 30% ethyl acetate in hexanes) provided the product as a yellow oil. Yield: 50 mg, 0.22 mmol, 48%. GCMS m/z 230 [M$^+$]. $^1$H NMR (400 MHz, DMSO-d$_6$) δ 7.75-7.78 (m, 1H), 7.47 (br d, J=8.3 Hz, 1H), 7.00 (d, J=8.8 Hz, 1H), 4.98 (dd, J=5.9, 5.4 Hz, 1H), 4.93 (dd, J=5.5, 1.8 Hz, 1H), 3.93 (dd, half of ABX pattern, J=11.8, 5.9 Hz, 1H), 3.73 (dd, half of ABX pattern, J=11.9, 5.3 Hz, 1H), 1.26 (dd, J=6.2, 5.8 Hz, 1H), 0.40 (dd, J=6.5, 1.8 Hz, 1H).

Step 8. Synthesis of [5-(trifluoromethyl)-1,1a-dihydro-6bH-cyclopropa[b][1]benzofuran-6b-yl] methyl methanesulfonate (C8)

Triethylamine (0.27 mL, 1.9 mmol) and methanesulfonyl chloride (61 μL, 0.79 mmol) were added to a 0° C. solution of C7 (150 mg, 0.65 mmol) in dichloromethane (10 mL), and the reaction mixture was allowed to slowly warm to room temperature. After it had stirred for 6 hours, the reaction mixture was quenched via addition of saturated aqueous sodium bicarbonate solution, and extracted with dichloromethane. The combined organic layers were washed with saturated aqueous sodium chloride solution, dried over sodium sulfate, filtered, and concentrated in vacuo to afford the product (120 mg). This material was used directly in the following step.

Step 9. Synthesis of 1-[5-(trifluoromethyl)-1,1a-dihydro-6bH-cyclopropa[b][1]benzofuran-6b-yl] methanamine (C9)

To a 0° C. solution of C8 (from the previous step; 120 mg, ≤0.39 mmol) in methanol (1 mL) was added methanolic ammonia (5 mL) and the reaction mixture was heated at 70° C. for 16 hours in a sealed tube. It was then evaporated to dryness; the residue was mixed with water and extracted with ethyl acetate. The combined organic layers were washed with saturated aqueous sodium chloride solution, dried over sodium sulfate, filtered, and concentrated in vacuo. Chromatography on silica gel (Eluent: 10% methanol in dichloromethane) afforded the product as a light yellow gum. Yield: 50 mg, 0.22 mmol, 34% over two steps.

Step 10. Synthesis of 1-(2-hydroxyethyl)-5-(4-methyl-1H-imidazol-1-yl)-6-oxo-N-{[5-(trifluoromethyl)-1,1a-dihydro-6bH-cyclopropa[b][1]benzofuran-6b-yl]methyl}-1,6-dihydropyridine-2-carboxamide (C11)

To a solution of C9 (115 mg, 0.502 mmol) in tetrahydrofuran (1 L) was added bis(trimethylaluminum)-1,4-diazabicyclo[2.2.2]octane adduct (270 mg, 1.05 mmol). The reaction mixture was heated to 40° C. for 45 minutes, whereupon it was treated with 7-(4-methyl-1H-imidazol-1-yl)-3,4-dihydropyrido[2,1-c][1,4]oxazine-1,6-dione (C10, which may be prepared via the method of C. W. amEnde et al., PCT Int. Appl., WO 2012131539, Oct. 4, 2012) (120 mg, 0.49 mmol) and heated to 65° C. for 5 hours. The reaction was quenched via addition of 1 M aqueous sodium hydroxide solution, and the resulting slurry was diluted with water and extracted with 5% methanol in dichloromethane; the combined organic layers were washed with saturated aqueous sodium chloride solution, dried over sodium sulfate, filtered, and concentrated in vacuo. Trituration with 10% ethyl acetate in hexanes afforded the product as an off-white solid (100 mg), which was used in the next step without additional purification. LCMS m/z 475.0 [M+H]$^+$.

Step 11. Synthesis of 1-(2-chloroethyl)-5-(4-methyl-1H-imidazol-1-yl)-6-oxo-N-{[5-(trifluoromethyl)-1,1a-dihydro-6bH-cyclopropa[b][1]benzofuran-6b-yl]methyl}-1,6-dihydropyridine-2-carboxamide (C12)

To a −10° C. solution of C11 (from the previous step; 100 mg, ≤0.21 mmol) in dichloromethane (10 mL) was added triethylamine (90 μL, 0.65 mmol), followed by drop-wise addition of methanesulfonyl chloride (70 mg, 0.61 mmol). The reaction mixture was then allowed to warm to room temperature and stir for 2 hours, whereupon it was diluted with dichloromethane, washed with aqueous sodium bicarbonate solution and with saturated aqueous sodium chloride solution, dried over sodium sulfate, filtered, and evaporated in vacuo. The product was obtained as a sticky brown solid (100 mg), which was used in the next step without additional purification.

Step 12. Synthesis of 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione (1)

To a solution of C12 (from the previous step; 100 mg, <1.20 mmol) in tetrahydrofuran (10 mL) was added 1,3,4,6,7,8-hexahydro-2H-pyrimido[1,2-a]pyrimidine (99 mg, 0.71 mmol) and the reaction mixture was allowed to stir at room temperature for 16 hours. Ice water was added, and the mixture was evaporated to dryness under reduced pressure; the residue was diluted with water and extracted with ethyl acetate. The combined organic layers were washed with saturated aqueous sodium chloride solution, dried over sodium sulfate, filtered, and concentrated in vacuo. Reversed phase HPLC (Column: YMC-Actus Triart C18, 5 μm; Mobile phase A: 20 mM ammonium bicarbonate in water; Mobile phase B: acetonitrile; Gradient: 10% to 55% B) afforded the product as an off-white solid. Yield: 18 mg, 39 μmol, 8% over three steps. LCMS m/z 457.0 [M+H]$^+$. $^1$H NMR (400 MHz, CDCl$_3$) δ 8.20 (s, 1H), 7.62-7.65 (m, 1H), 7.43 (d, J=7.6 Hz, 1H), 7.40-7.45 (m, 1H), 7.24-7.3 (m, 1H, assumed; partially obscured by solvent peak), 7.09-7.13 (m, 1H), 6.91 (d, J=8.6 Hz, 1H), 4.90-4.94 (m, 1H), 4.86 (d, J=14.7 Hz, 1H), 4.26-4.35 (m, 1H), 4.11-4.20 (m, 1H), 3.54-3.64 (m, 2H), 3.43 (d, J=14.8 Hz, 1H), 2.28 (s, 3H), 1.25 (dd, J=6.7, 5.8 Hz, 1H), 0.62 (dd, J=7, 2 Hz, 1H).

Examples 2 and 3

7-(4-Methyl-1H-imidazol-1-yl)-2-{[(1aS,6bS)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione (2) and 7-(4-Methyl-1H-imidazol-1-yl)-2-{[(1aR,6bR)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione (3)

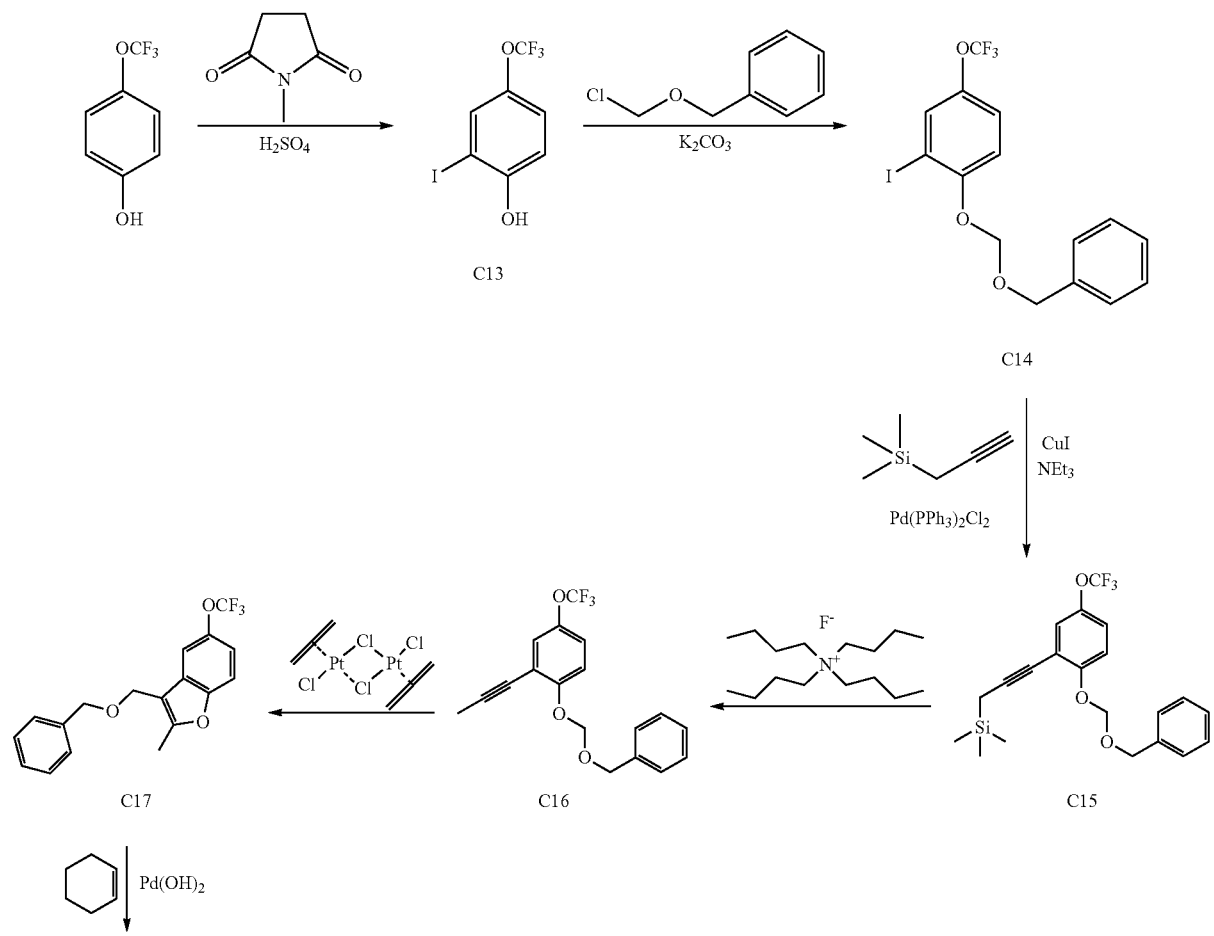

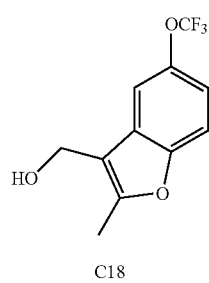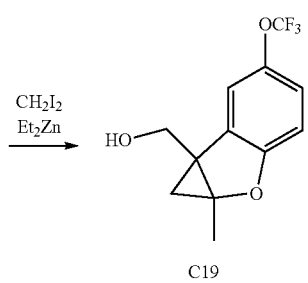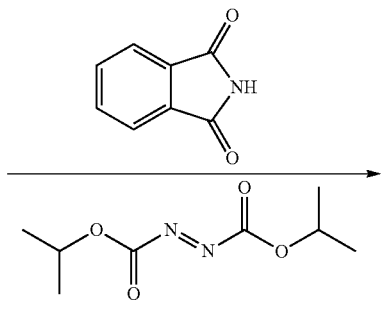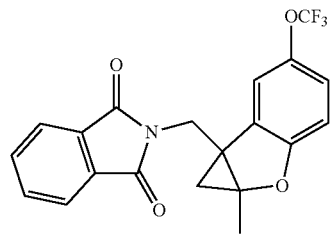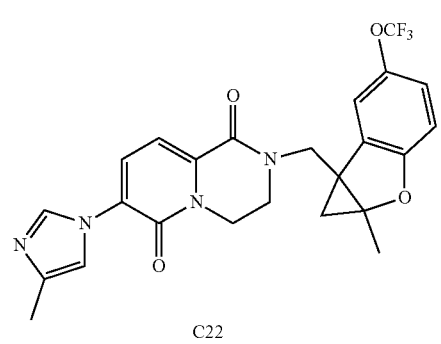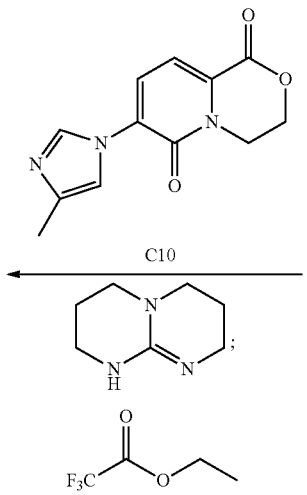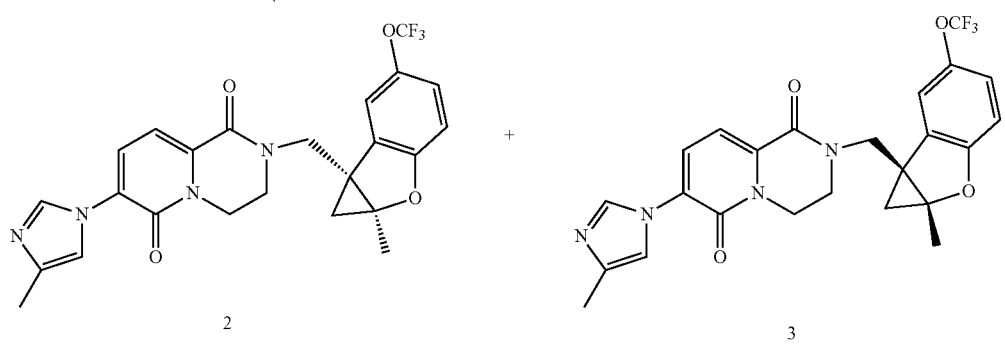

Step 1. Synthesis of 2-iodo-4-(trifluoromethoxy)phenol (C13)

4-(Trifluoromethoxy)phenol (4.0 mL, 31 mmol) was added to a suspension of N-iodosuccinimide (95%, 6.95 g, 29.3 mmol) in acetic acid (2.0 mL, 35 mmol), and the mixture was stirred for 5 minutes. Sulfuric acid (98%, 0.5 mL, 9 mmol) was introduced, and stirring was continued at room temperature for 48 hours, whereupon the reaction mixture was poured into water (100 mL) and extracted with diethyl ether. The combined organic layers were washed with water, washed twice with 1 M aqueous sodium thiosulfate solution, treated with decolorizing carbon, and dried over magnesium sulfate. After the mixture had been filtered through a pad of diatomaceous earth and silica gel, the filtrate was concentrated in vacuo to provide the product as an oil (13.2 g). By $^1$H NMR analysis, this product contained a significant quantity of ethyl acetate. Yield, corrected for ethyl acetate: 8.5 g, 28 mmol, 96%. $^1$H NMR (400 MHz, CDCl$_3$) δ 7.54 (br d, J=2.6 Hz, 1H), 7.15 (br dd, J=8.9, 2.6 Hz, 1H), 6.99 (d, J=8.9 Hz, 1H).

Step 2. Synthesis of 1-[(benzyloxy)methoxy]-2-iodo-4-(trifluoromethoxy)benzene (C14)

A solution of C13 (9.30 g, 30.6 mmol) in acetonitrile (100 mL) was treated with potassium carbonate (8.46 g, 61.2 mmol), followed by benzyl chloromethyl ether (6.38 mL, 45.9 mmol). The reaction mixture was allowed to stir at room temperature overnight, whereupon it was partitioned between water and diethyl ether. The combined organic layers were washed with water, dried over magnesium sulfate, filtered, and concentrated in vacuo; purification via silica gel chromatography (Gradient: 0% to 5% ethyl acetate in heptane) provided the product as an oil. Yield: 10.8 g, 25.5 mmol, 83%. $^1$H NMR (400 MHz, CDCl$_3$) δ 7.67 (br d, J=2.2 Hz, 1H), 7.30-7.40 (m, 5H), 7.19 (br dd, half of ABX pattern, J=9, 2 Hz, 1H), 7.14 (d, half of AB quartet, J=9.0 Hz, 1H), 5.35 (s, 2H), 4.76 (s, 2H).

Step 3. Synthesis of (3-{2-[(benzyloxy)methoxy]-5-(trifluoromethoxy)phenyl}prop-2-yn-1-yl)(trimethyl)silane (C15)

A mixture of C14 (2.80 g, 6.60 mmol), copper(I) iodide (254 mg, 1.33 mmol), and dichlorobis(triphenylphosphine)palladium(II) (99%, 468 mg, 0.660 mmol) in triethylamine (20 mL) was stirred for 5 minutes, whereupon trimethyl(prop-2-yn-1-yl)silane (80%, 1.85 mL, 9.9 mmol) was added and the reaction mixture was heated to 50° C. After 5 hours, it was cooled to room temperature and partitioned between diethyl ether and saturated aqueous ammonium chloride solution. The organic layer was washed with 1 M aqueous hydrochloric acid, dried over magnesium sulfate, filtered, and concentrated in vacuo. The product was obtained as a thick oil, which was used without additional purification. Yield: 2.69 g, 6.58 mmol, quantitative. GCMS m/z 408.2 [M$^+$].

Step 4. Synthesis of 1-[(benzyloxy)methoxy]-2-(prop-1-yn-1-yl)-4-(trifluoromethoxy)benzene (C16)

Tetrabutylammonium fluoride (1 M solution in tetrahydrofuran; 10 mL, 10 mmol) was added to a solution of C15 (2.60 g, 6.36 mmol) in tetrahydrofuran (25 mL), and the reaction mixture was stirred at room temperature. After 2 hours, it was partitioned between water and diethyl ether; the organic layer was washed with water, dried over magnesium sulfate, filtered, and concentrated under reduced pressure. Silica gel chromatography (Gradient: 0% to 5% ethyl acetate in heptane) afforded the product as an oil. Yield: 1.99 g, 5.92 mmol, 93%. $^1$H NMR (400 Hz, CDCl$_3$) δ 7.29-7.40 (m, 5H), 7.24-7.27 (m, 1H, assumed; partially obscured by solvent peak), 7.17 (d, half of AB quartet, J=9.0 Hz, 1H), 7.08 (br d, half of AB quartet, J=9 Hz, 1H), 5.36 (s, 2H), 4.78 (s, 2H), 2.12 (s, 3H).

Step 5. Synthesis of 3-[(benzyloxy)methyl]-2-methyl-5-(trifluoromethoxy)-1-benzofuran (C17)

Compound C16 (1.99 g, 5.92 mmol) and di-mu-chloro-dichlorobis(ethylene)diplatinum(II) (Zeise's dimer; 190 mg, 0.32 mmol) were combined in toluene (20 mL) and heated to 35° C. for 3 hours. After the reaction mixture had cooled to room temperature, silica gel chromatography (Gradient: 0% to 5% ethyl acetate in heptane) provided the product as a solid. Yield: 1.50 g, 4.46 mmol, 75%. $^1$H NMR (400 MHz, CDCl$_3$) δ 7.29-7.42 (m, 7H), 7.09 (br d, J=8.8 Hz, 1H), 4.61 (s, 2H), 4.57 (s, 2H), 2.44 (s, 3H).

Step 6. Synthesis of [2-methyl-5-(trifluoromethoxy)-1-benzofuran-3-yl]methanol (C18)

A solution of C17 (1.80 g, 5.35 mmol) in ethanol (25 mL) was treated with palladium hydroxide on carbon (20%, 1.0 g). Cyclohexene (6 mL, 60 mmol) was added, and the reaction mixture was heated at reflux for 5 hours, whereupon it was cooled and treated with additional palladium hydroxide on carbon (1.0 g) and cyclohexene (6 mL, 60 mmol). After being heated overnight at reflux, the reaction mixture was filtered through diatomaceous earth, and the filtrate was concentrated in vacuo. Silica gel chromatography (Gradient: 0% to 50% ethyl acetate in heptane) afforded the product as a white solid. Yield: 787 mg, 3.20 mmol, 60%. GCMS m/z 246.1 [M$^+$]. $^1$H NMR (400 MHz, CDCl$_3$) δ 7.47 (br s, 1H), 7.38 (d, J=8.8 Hz, 1H), 7.10 (br d, J=8.8 Hz, 1H), 4.77 (s, 2H), 2.48 (s, 3H).

Step 7. Synthesis of [1a-methyl-5-(trifluoromethoxy)-1,1a-dihydro-6bH-cyclopropa[b][1]benzofuran-6b-yl]methanol (C19)

Diethylzinc (1.0 M solution in hexane; 10.4 mL, 10.4 mmol) was cooled in an ice bath, diluted with dichloromethane (10 mL), and treated with a solution of diiodomethane (1.67 mL, 20.7 mmol) in dichloromethane (2 mL). After 5 minutes, a solution of C18 (510 mg, 2.07 mmol) in dichloromethane (10 mL) was added, and stirring was continued for 5 minutes at 0° C. The reaction mixture was then allowed to warm to room temperature and stir for 4 hours, whereupon it was quenched with saturated aqueous ammonium chloride solution. The mixture was extracted with diethyl ether, and the combined organic layers were dried over magnesium sulfate, filtered, concentrated in vacuo, and purified via silica gel chromatography (Gradient: 5% to 30% ethyl acetate in heptane). The product was obtained as a solid. Yield: 500 mg, 1.9 mmol, 92%. GCMS m/z 260.1 [M$^+$]. $^1$H NMR (400 MHz, CDCl$_3$) δ 7.26-7.30 (m, 1H, assumed; largely obscured by solvent peak), 6.98 (br d, J=8.8 Hz, 1H), 6.79 (d, J=8.7 Hz, 1H), 4.14 (d, J=12.1 Hz, 1H), 3.87 (d, J=12.0 Hz, 1H), 1.76 (s, 3H), 1.07 (d, J=6.2 Hz, 1H), 0.62 (d, J=6.2 Hz, 1H).

Step 8. Synthesis of 2-{[1a-methyl-5-(trifluoromethoxy)-1,1a-dihydro-6bH-cyclopropa[b][1]benzofuran-6b-yl]methyl}-1H-isoindole-1,3(2H)-dione (C20)

1H-Isoindole-1,3(2H)-dione (1.64 g, 11.1 mmol) and triphenylphosphine (2.89 g, 11.0 mmol) were added to a solution of C19 (2.40 g, 9.22 mmol) in tetrahydrofuran (50 mL). Diisopropyl azodicarboxylate (95%, 2.07 mL, 10.2 mmol) was added drop-wise, and the reaction mixture was allowed to stir at room temperature for 2 hours. It was then partitioned between diethyl ether and saturated aqueous sodium chloride solution, and the organic layer was dried over magnesium sulfate, filtered, and concentrated in vacuo. Silica gel chromatography (Gradient: 5% to 50% ethyl acetate in heptane) afforded the product as a thick oil. Yield: 1.6 g, 4.1 mmol, 44%. LCMS m/z 389.8 [M+H]$^+$. $^1$H NMR (400 MHz, CDCl$_3$) δ 7.86-7.90 (m, 2H), 7.73-7.77 (m, 2H), 7.61-7.65 (m, 1H), 6.94 (br d, J=8.7 Hz, 1H), 6.75 (d, J=8.7 Hz, 1H), 4.24 (d, J=15.2 Hz, 1H), 3.98 (d, J=15.3 Hz, 1H), 1.92 (s, 3H), 1.12 (d, J=6.3 Hz, 1H), 0.52 (d, J=6.3 Hz, 1H).

Step 9. Synthesis of 1-[1a-methyl-5-(trifluoromethoxy)-1,1a-dihydro-6bH-cyclopropa[b][1]benzofuran-6b-yl]methanamine (C21)

Hydrazine monohydrate (2.0 mL, 41 mmol) was added to a solution of C20 (1.6 g, 4.1 mmol) in dichloromethane (10 mL) and methanol (10 mL). The reaction mixture was stirred overnight at room temperature, whereupon it was partitioned between 1 M aqueous sodium hydroxide solution and diethyl ether. The aqueous layer was extracted with diethyl ether, and the combined organic layers were dried over sodium sulfate, filtered, and concentrated under reduced pressure, providing the product as a thick oil. Yield: 1.0 g, 3.9 mmol, 95%. $^1$H NMR (400 MHz, CDCl$_3$) δ 7.20-7.24 (m, 1H), 6.97 (br d, J=8.7 Hz, 1H), 6.78 (d, J=8.7 Hz, 1H), 3.39 (d, J=14.2 Hz, 1H), 2.86 (d, J=14.0 Hz, 1H), 1.75 (s, 3H), 0.95 (d, J=6.2 Hz, 1H), 0.55 (d, J=6.2 Hz, 1H).

Step 10. Synthesis of 7-(4-methyl-1H-imidazol-1-yl)-2-{[1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione (C22)

1,3,4,6,7,8-Hexahydro-2H-pyrimido[1,2-a]pyrimidine (97%, 830 mg, 5.78 mmol) was added to a solution of C21 (1.00 g, 3.86 mmol) and C10 (1.26 g, 5.14 mmol) in N,N-dimethylformamide (4 mL). After 3 hours at room temperature, the reaction mixture was treated with ethyl trifluoroacetate (1.1 mL, 9.2 mmol) and allowed to stir overnight. Aqueous sodium hydroxide solution (1 M, 6 mL, 6 mmol) was added, and the mixture was stirred for 15 minutes at room temperature. The solid was collected via filtration, rinsed with water and with diethyl ether, and azeotroped 3 times with toluene, affording the product as an off-white solid. Yield: 1.68 g, 3.45 mmol, 89%. LCMS m/z 487.4 [M+H]$^+$. $^1$H NMR (400 MHz, CDCl$_3$), characteristic peaks: δ 8.21 (s, 1H), 7.45 (d, J=7.7 Hz, 1H), 7.11-7.14 (m, 1H), 6.98 (br d, J=9 Hz, 1H), 6.81 (d, J=8.7 Hz, 1H), 5.05 (d, J=15.2 Hz, 1H), 4.23 (d, half of ABXY pattern, J=14, 8, 4 Hz, 1H), 4.15 (ddd, half of ABXY pattern, J=14, 7, 4 Hz, 1H), 3.56 (ddd, half of ABXY pattern, J=13, 7, 4 Hz, 1H), 3.46 (ddd, half of ABXY pattern, J=13, 8, 4 Hz, 1H), 3.18 (d, J=15.2 Hz, 1H), 2.29 (s, 3H), 1.84 (s, 3H), 1.00 (d, J=6.5 Hz, 1H), 0.68 (d, J=6.4 Hz, 1H).

Step 11. Isolation of 7-(4-methyl-1H-imidazol-1-yl)-2-{[(1aS,6bS)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione (2) and 7-(4-methyl-1H-imidazol-1-yl)-2-{[(1aR,6bR)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione (3)

Compound C22 (1.68 g, 3.45 mmol) was separated into its component enantiomers via supercritical fluid chromatography (Column: Chiral Technologies Chiralpak AD-H, 5 µm; Mobile phase: 30% [0.2% ammonium hydroxide in methanol] in carbon dioxide). Each enantiomer was then dissolved in ethyl acetate (10 mL), passed through a syringe filter, and concentrated in vacuo. The first-eluting enantiomer was triturated with diethyl ether to afford 3 as a solid. The second-eluting enantiomer was recrystallized from ethyl acetate/heptane to provide 2 as a solid.

3: Yield: 435 mg, 0.894 mmol, 26%. LCMS m/z 487.4 [M+H]$^+$. $^1$H NMR (400 MHz, CD$_3$OD) δ 8.28 (br s, 1H), 7.77 (d, J=7.8 Hz, 1H), 7.28-7.32 (m, 2H), 7.28 (d, J=7.8 Hz, 1H), 6.96-7.01 (m, 1H), 6.83 (d, J=8.7 Hz, 1H), 4.93 (d, J=15.1 Hz, 1H), 4.13-4.25 (m, 2H), 3.72 (ddd, J=13, 6, 5 Hz, 1H), 3.50 (ddd, J=13, 8, 5 Hz, 1H), 3.39 (d, J=15.2 Hz, 1H), 2.23 (d, J=0.9 Hz, 3H), 1.85 (s, 3H), 1.14 (d, J=6.4 Hz, 1H), 0.57 (d, J=6.5 Hz, 1H).

2: Yield: 447 mg, 0.919 mmol, 27%. LCMS m/z 487.4 [M+H]$^+$. $^1$H NMR (400 MHz, CD$_3$OD) δ 8.28 (br s, 1H), 7.77 (d, J=7.8 Hz, 1H), 7.28-7.32 (m, 2H), 7.28 (d, J=7.8 Hz, 1H), 6.96-7.01 (m, 1H), 6.83 (d, J=8.8 Hz, 1H), 4.93 (d, J=15.1 Hz, 1H), 4.13-4.25 (m, 2H), 3.72 (ddd, J=13, 6, 5 Hz, 1H), 3.50 (ddd, J=13, 8, 5 Hz, 1H), 3.39 (d, J=15.2 Hz, 1H), 2.23 (d, J=0.8 Hz, 3H), 1.85 (s, 3H), 1.14 (d, J=6.4 Hz, 1H), 0.57 (d, J=6.4 Hz, 1H). Compound 2 was subjected to X-ray structural analysis (see below), which established its absolute stereochemistry. Compound 2 was more potent than its enantiomer 3 (see Table 7); this potency difference was observed for all of the separated enantiomers in these Examples, and was used to assign the absolute stereochemistry in all cases, in direct analogy with 2 and 3.

Single Crystal X-Ray Analysis of Compound 2

Data collection was performed on a Bruker APEX diffractometer at room temperature. Data collection consisted of omega and phi scans.

The structure was solved by direct methods using SHELX software suite in the space group P1. The structure was subsequently refined by the full-matrix least squares method. All non-hydrogen atoms were found and refined using anisotropic displacement parameters.

The conformations of the two molecules in the asymmetric unit are slightly different from one other. Both molecules have the same stereochemistry.

All hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). The results indicate that the absolute structure has been correctly assigned. The method calculates that the probability that the structure is correct is 100.0%. The Hooft parameter is reported as 0.07 with an esd of 0.06.

The final R-index was 5%. A final difference Fourier revealed no missing or misplaced electron density.

Pertinent crystal, data collection, and refinement information is summarized in Table 1. Atomic coordinates, bond lengths, bond angles, and displacement parameters are listed in Tables 2-5.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Strayer, and A. L. Spek, *J. Appl. Cryst.* 2008, 41, 96-103.
H. D. Flack, *Acta Cryst.* 1983, A39, 867-881.

TABLE 1

Crystal data and structure refinement for 2.

| | |
|---|---|
| Empirical formula | $C_{24}H_{21}F_3N_4O_4 \cdot H_2O$ |
| Formula weight | 486.45•18.02 |
| Temperature | 296(2) K |
| Wavelength | 1.54178 Å |
| Crystal system | Triclinic |
| Space group | P1 |
| Unit cell dimensions | a = 6.6264(13) Å α = 85.796(14)°. |
| | b = 7.8303(18) Å β = 85.470(13)°. |
| | c = 22.676(5) Å γ = 69.694(12)°. |
| Volume | 1098.7(4) Å$^3$ |
| Z | 2 |
| Density (calculated) | 1.531 Mg/m$^3$ |
| Absorption coefficient | 1.070 mm$^{-1}$ |
| F(000) | 528 |
| Crystal size | 0.44 × 0.28 × 0.02 mm$^3$ |
| Theta range for data collection | 3.92 to 75.44° |
| Index ranges | −7 <= h <= 8, −9 <= k <= 9, −28 <= l <= 28 |
| Reflections collected | 47975 |
| Independent reflections | 8409 [R(int) = 0.0591] |
| Completeness to theta = 67.42° | 94.9% |
| Absorption correction | Empirical |
| Max. and min. transmission | 0.9789 and 0.6502 |
| Refinement method | Full-matrix least-squares on F$^2$ |
| Data/restraints/parameters | 8409/3/653 |
| Goodness-of-fit on F$^2$ | 1.045 |
| Final R indices [I > 2sigma(I)] | R1 = 0.0498, wR2 = 0.1078 |
| R indices (all data) | R1 = 0.0776, wR2 = 0.1205 |
| Absolute structure parameter | 0.010(15) |
| Largest diff. peak and hole | 0.350 and −0.205 e.Å$^{-3}$ |

TABLE 2

Atomic coordinates (×10$^4$) and equivalent isotropic displacement parameters (Å$^2$ × 10$^3$) for 2. U(eq) is defined as one third of the trace of the orthogonalized U$^{ij}$ tensor.

| | x | y | z | U(eq) |
|---|---|---|---|---|
| O(1) | 6220(3) | 3512(4) | 5522(1) | 66(1) |
| O(2) | −850(3) | 3297(4) | 7118(1) | 65(1) |
| O(3) | 1088(4) | 3538(3) | 9359(1) | 59(1) |
| O(4) | 8843(4) | −1958(3) | 9402(1) | 58(1) |
| O(5) | 6668(3) | −649(3) | 4986(1) | 58(1) |

TABLE 2-continued

Atomic coordinates (×10$^4$) and equivalent isotropic displacement parameters (Å$^2$ × 10$^3$) for 2. U(eq) is defined as one third of the trace of the orthogonalized U$^{ij}$ tensor.

| | x | y | z | U(eq) |
|---|---|---|---|---|
| O(6) | 1207(3) | 3621(3) | 3150(1) | 58(1) |
| O(7) | 6354(4) | 1725(3) | 1207(1) | 63(1) |
| O(8) | 9200(4) | 7429(3) | 1072(1) | 58(1) |
| F(1) | 10879(5) | −962(5) | 8784(2) | 130(1) |
| F(2) | 12248(4) | −3031(4) | 9426(1) | 92(1) |
| F(3) | 10687(5) | −347(4) | 9649(2) | 120(1) |
| F(4) | 11615(7) | 6781(6) | 1706(2) | 148(2) |
| F(5) | 12563(5) | 6046(5) | 857(2) | 153(2) |
| F(6) | 11462(5) | 8765(4) | 1046(1) | 108(1) |
| N(1) | 4964(5) | 6957(4) | 4069(1) | 58(1) |
| N(2) | 3148(4) | 6036(3) | 4798(1) | 41(1) |
| N(3) | 3684(4) | 3491(3) | 6227(1) | 42(1) |
| N(4) | 2597(4) | 2304(4) | 7349(1) | 51(1) |
| N(5) | 3814(6) | −2090(6) | 6465(2) | 84(1) |
| N(6) | 2854(4) | −310(3) | 5672(1) | 46(1) |
| N(7) | 4789(3) | 1192(3) | 4255(1) | 37(1) |
| N(8) | 4782(4) | 3031(3) | 3150(1) | 41(1) |
| C(1) | 5068(5) | 6128(5) | 4595(2) | 56(1) |
| C(2) | 2881(5) | 7380(4) | 3921(1) | 48(1) |
| C(3) | 2170(7) | 8349(5) | 3344(2) | 61(1) |
| C(4) | 1758(5) | 6858(5) | 4361(2) | 51(1) |
| C(5) | 2625(5) | 5349(5) | 5345(1) | 39(1) |
| C(6) | 563(5) | 5826(5) | 5557(1) | 50(1) |
| C(7) | 27(5) | 5093(5) | 6095(1) | 51(1) |
| C(8) | 1586(6) | 3941(4) | 6423(1) | 42(1) |
| C(9) | 4321(5) | 4075(4) | 5686(1) | 44(1) |
| C(10) | 5360(5) | 2221(6) | 6590(1) | 60(1) |
| C(11) | 4713(5) | 2404(6) | 7219(2) | 68(1) |
| C(12) | 1013(5) | 3146(5) | 6998(1) | 48(1) |
| C(13) | 2187(6) | 1483(5) | 7921(1) | 53(1) |
| C(14) | 2422(5) | 2490(4) | 8417(1) | 48(1) |
| C(15) | 1928(7) | 4516(5) | 8356(2) | 66(1) |
| C(16) | 553(6) | 3778(5) | 8767(2) | 57(1) |
| C(17) | −1751(7) | 4174(6) | 8698(2) | 79(1) |
| C(18) | 3087(5) | 2275(5) | 9402(1) | 50(1) |
| C(19) | 3966(5) | 1538(4) | 8876(1) | 46(1) |
| C(20) | 5883(5) | 134(5) | 8867(2) | 49(1) |
| C(21) | 6891(5) | −464(4) | 9392(2) | 50(1) |
| C(22) | 6053(6) | 289(5) | 9904(2) | 57(1) |
| C(23) | 4109(6) | 1687(5) | 9917(2) | 60(1) |
| C(24) | 10628(7) | −1590(6) | 9314(2) | 68(1) |
| C(25) | 4461(7) | −1528(6) | 5965(2) | 77(1) |
| C(26) | 1668(7) | −1189(5) | 6511(2) | 62(1) |
| C(27) | 474(9) | −1531(7) | 7047(2) | 97(2) |
| C(28) | 1075(6) | −119(6) | 6033(2) | 66(1) |
| C(29) | 2881(5) | 586(4) | 5113(1) | 41(1) |
| C(30) | 1022(5) | 1672(4) | 4875(1) | 48(1) |
| C(31) | 1049(5) | 2496(4) | 4318(1) | 46(1) |
| C(32) | 2914(4) | 2229(4) | 4007(1) | 36(1) |
| C(33) | 4925(5) | 299(4) | 4804(1) | 41(1) |
| C(34) | 6795(4) | 878(4) | 3901(1) | 44(1) |
| C(35) | 6645(4) | 2524(4) | 3506(1) | 45(1) |
| C(36) | 2898(5) | 3023(4) | 3398(1) | 40(1) |
| C(37) | 4864(5) | 4036(5) | 2593(1) | 50(1) |
| C(38) | 6253(5) | 2897(4) | 2125(1) | 45(1) |

TABLE 2-continued

Atomic coordinates (×10⁴) and equivalent isotropic displacement parameters ($Å^2 × 10^3$) for 2. U(eq) is defined as one third of the trace of the orthogonalized $U^{ij}$ tensor.

| | x | y | z | U(eq) |
|---|---|---|---|---|
| C(39) | 7514(6) | 886(5) | 2208(2) | 60(1) |
| C(40) | 5735(6) | 1526(5) | 1810(2) | 55(1) |
| C(41) | 3761(8) | 1048(7) | 1889(2) | 87(1) |
| C(42) | 7224(5) | 3046(4) | 1140(1) | 47(1) |
| C(43) | 7187(5) | 3847(4) | 1650(1) | 44(1) |
| C(44) | 7845(5) | 5304(4) | 1639(1) | 45(1) |
| C(45) | 8629(5) | 5859(4) | 1110(2) | 48(1) |
| C(46) | 8725(6) | 5031(5) | 612(2) | 58(1) |
| C(47) | 8045(7) | 3581(5) | 623(2) | 66(1) |
| C(48) | 11161(7) | 7242(6) | 1163(2) | 70(1) |
| O(1W) | 7768(5) | 6991(4) | 3086(1) | 84(1) |
| O(2W) | 6075(9) | 7130(10) | 7482(2) | 189(2) |

TABLE 3

Bond lengths [Å] and angles [°] for 2.

| | | | | |
|---|---|---|---|---|
| O(1)—C(9) | 1.217(4) | N(3)—C(9) | 1.364(4) |
| O(2)—C(12) | 1.209(4) | N(3)—C(10) | 1.469(4) |
| O(3)—C(18) | 1.356(4) | N(4)—C(12) | 1.321(4) |
| O(3)—C(16) | 1.398(4) | N(4)—C(11) | 1.438(4) |
| O(4)—C(24) | 1.308(5) | N(4)—C(13) | 1.454(4) |
| O(4)—C(21) | 1.412(4) | N(5)—C(25) | 1.282(5) |
| O(5)—C(33) | 1.221(3) | N(5)—C(26) | 1.350(5) |
| O(6)—C(36) | 1.220(3) | N(6)—C(25) | 1.342(5) |
| O(7)—C(42) | 1.343(4) | N(6)—C(28) | 1.351(4) |
| O(7)—C(40) | 1.409(4) | N(6)—C(29) | 1.406(4) |
| O(8)—C(48) | 1.288(5) | N(7)—C(32) | 1.365(3) |
| O(8)—C(45) | 1.402(4) | N(7)—C(33) | 1.375(4) |
| F(1)—C(24) | 1.286(5) | N(7)—C(34) | 1.451(3) |
| F(2)—C(24) | 1.285(5) | N(8)—C(36) | 1.330(4) |
| F(3)—C(24) | 1.290(5) | N(8)—C(37) | 1.446(4) |
| F(4)—C(48) | 1.285(5) | N(8)—C(35) | 1.450(4) |
| F(5)—C(48) | 1.269(5) | C(2)—C(4) | 1.322(5) |
| F(6)—C(48) | 1.282(5) | C(2)—C(3) | 1.488(5) |
| N(1)—C(1) | 1.311(4) | C(5)—C(6) | 1.344(4) |
| N(1)—C(2) | 1.366(4) | C(5)—C(9) | 1.449(4) |
| N(2)—C(1) | 1.341(4) | C(6)—C(7) | 1.384(4) |
| N(2)—C(4) | 1.372(4) | C(7)—C(8) | 1.345(4) |
| N(2)—C(5) | 1.384(4) | C(8)—C(12) | 1.482(4) |
| N(3)—C(8) | 1.356(4) | C(10)—C(11) | 1.461(5) |
| C(13)—C(14) | 1.469(5) | C(1)—N(1)—C(2) | 105.5(3) |
| C(14)—C(19) | 1.486(4) | C(1)—N(2)—C(4) | 105.8(3) |
| C(14)—C(15) | 1.502(5) | C(1)—N(2)—C(5) | 127.6(3) |
| C(14)—C(16) | 1.508(5) | C(4)—N(2)—C(5) | 126.5(3) |
| C(15)—C(16) | 1.478(5) | C(8)—N(3)—C(9) | 123.0(2) |
| C(16)—C(17) | 1.468(5) | C(8)—N(3)—C(10) | 119.3(2) |
| C(18)—C(19) | 1.361(4) | C(9)—N(3)—C(10) | 117.6(2) |
| C(18)—C(23) | 1.365(5) | C(12)—N(4)—C(11) | 121.0(3) |
| C(19)—C(20) | 1.361(5) | C(12)—N(4)—C(13) | 121.0(3) |
| C(20)—C(21) | 1.382(5) | C(11)—N(4)—C(13) | 117.4(3) |
| C(21)—C(22) | 1.332(5) | C(25)—N(5)—C(26) | 105.2(3) |
| C(22)—C(23) | 1.371(5) | C(25)—N(6)—C(28) | 104.4(3) |
| C(26)—C(28) | 1.318(5) | C(25)—N(6)—C(29) | 130.4(3) |
| C(26)—C(27) | 1.457(5) | C(28)—N(6)—C(29) | 125.2(3) |
| C(29)—C(30) | 1.357(4) | C(32)—N(7)—C(33) | 125.0(2) |
| C(29)—C(33) | 1.427(4) | C(32)—N(7)—C(34) | 118.2(3) |
| C(30)—C(31) | 1.379(4) | C(33)—N(7)—C(34) | 116.6(2) |
| C(31)—C(32) | 1.331(4) | C(36)—N(8)—C(37) | 120.1(3) |
| C(32)—C(36) | 1.471(4) | C(36)—N(8)—C(35) | 119.8(2) |
| C(34)—C(35) | 1.494(4) | C(37)—N(8)—C(35) | 117.5(2) |
| C(37)—C(38) | 1.479(4) | N(1)—C(1)—N(2) | 111.6(3) |
| C(38)—C(40) | 1.479(5) | C(4)—C(2)—N(1) | 109.8(3) |
| C(38)—C(43) | 1.481(4) | C(4)—C(2)—C(3) | 129.7(3) |
| C(38)—C(39) | 1.510(5) | N(1)—C(2)—C(3) | 120.4(3) |
| C(39)—C(40) | 1.466(5) | C(2)—C(4)—N(2) | 107.2(3) |
| C(40)—C(41) | 1.475(6) | C(6)—C(5)—N(2) | 120.6(3) |
| C(42)—C(43) | 1.350(4) | C(6)—C(5)—C(9) | 120.0(3) |
| C(42)—C(47) | 1.352(4) | N(2)—C(5)—C(9) | 119.4(3) |
| C(43)—C(44) | 1.353(4) | C(5)—C(6)—C(7) | 120.8(3) |
| C(44)—C(45) | 1.372(4) | C(8)—C(7)—C(6) | 120.0(3) |

TABLE 3-continued

Bond lengths [Å] and angles [°] for 2.

| | | | | |
|---|---|---|---|---|
| C(45)—C(46) | 1.328(5) | C(7)—C(8)—N(3) | 120.2(3) |
| C(46)—C(47) | 1.358(5) | C(7)—C(8)—C(12) | 120.0(3) |
| C(18)—O(3)—C(16) | 109.2(3) | N(3)—C(8)—C(12) | 119.8(3) |
| C(24)—O(4)—C(21) | 116.9(3) | O(1)—C(9)—N(3) | 119.3(3) |
| C(42)—O(7)—C(40) | 108.9(2) | O(1)—C(9)—C(5) | 124.8(3) |
| C(48)—O(8)—C(45) | 117.9(3) | N(3)—C(9)—C(5) | 115.9(3) |
| C(11)—C(10)—N(3) | 110.8(3) | F(3)—C(24)—O(4) | 112.7(4) |
| N(4)—C(11)—C(10) | 111.7(3) | N(5)—C(25)—N(6) | 112.9(4) |
| O(2)—C(12)—N(4) | 124.0(3) | C(28)—C(26)—N(5) | 109.6(3) |
| O(2)—C(12)—C(8) | 118.8(3) | C(28)—C(26)—C(27) | 132.6(4) |
| N(4)—C(12)—C(8) | 117.2(3) | N(5)—C(26)—C(27) | 117.9(4) |
| N(4)—C(13)—C(14) | 112.4(3) | C(26)—C(28)—N(6) | 108.0(3) |
| C(13)—C(14)—C(19) | 119.8(3) | C(30)—C(29)—N(6) | 120.9(3) |
| C(13)—C(14)—C(15) | 120.9(3) | C(30)—C(29)—C(33) | 121.5(3) |
| C(19)—C(14)—C(15) | 114.4(3) | N(6)—C(29)—C(33) | 117.7(3) |
| C(13)—C(14)—C(16) | 124.0(3) | C(29)—C(30)—C(31) | 120.7(3) |
| C(19)—C(14)—C(16) | 103.4(3) | C(32)—C(31)—C(30) | 119.9(3) |
| C(15)—C(14)—C(16) | 58.8(2) | C(31)—C(32)—N(7) | 119.3(3) |
| C(16)—C(15)—C(14) | 60.8(2) | C(31)—C(32)—C(36) | 119.1(3) |
| O(3)—C(16)—C(17) | 113.1(3) | N(7)—C(32)—C(36) | 121.6(2) |
| O(3)—C(16)—C(15) | 115.4(3) | O(5)—C(33)—N(7) | 120.8(3) |
| C(17)—C(16)—C(15) | 123.6(3) | O(5)—C(33)—C(29) | 125.6(3) |
| O(3)—C(16)—C(14) | 107.1(3) | N(7)—C(33)—C(29) | 113.6(2) |
| C(17)—C(16)—C(14) | 127.2(3) | N(7)—C(34)—C(35) | 109.6(2) |
| C(15)—C(16)—C(14) | 60.4(2) | N(8)—C(35)—C(34) | 111.2(2) |
| O(3)—C(18)—C(19) | 113.1(3) | O(6)—C(36)—N(8) | 123.9(3) |
| O(3)—C(18)—C(23) | 125.0(3) | O(6)—C(36)—C(32) | 119.6(3) |
| C(19)—C(18)—C(23) | 121.8(3) | N(8)—C(36)—C(32) | 116.5(3) |
| C(20)—C(19)—C(18) | 119.0(3) | N(8)—C(37)—C(38) | 113.4(3) |
| C(20)—C(19)—C(14) | 133.8(3) | C(37)—C(38)—C(40) | 125.6(3) |
| C(18)—C(19)—C(14) | 107.2(3) | C(37)—C(38)—C(43) | 116.5(3) |
| C(19)—C(20)—C(21) | 118.6(3) | C(40)—C(38)—C(43) | 103.8(3) |
| C(22)—C(21)—C(20) | 122.3(3) | C(37)—C(38)—C(39) | 124.5(3) |
| C(22)—C(21)—O(4) | 117.6(3) | C(40)—C(38)—C(39) | 58.7(2) |
| C(20)—C(21)—O(4) | 120.1(3) | C(43)—C(38)—C(39) | 114.0(3) |
| C(21)—C(22)—C(23) | 119.4(3) | C(40)—C(39)—C(38) | 59.5(2) |
| C(18)—C(23)—C(22) | 118.9(3) | O(7)—C(40)—C(39) | 115.1(3) |
| F(2)—C(24)—F(1) | 109.6(4) | O(7)—C(40)—C(41) | 112.0(3) |
| F(2)—C(24)—F(3) | 107.4(4) | C(39)—C(40)—C(41) | 124.5(3) |
| F(1)—C(24)—F(3) | 104.6(4) | O(7)—C(40)—C(38) | 107.0(3) |
| F(2)—C(24)—O(4) | 109.7(3) | C(39)—C(40)—C(38) | 61.7(2) |
| F(1)—C(24)—O(4) | 112.7(4) | C(41)—C(40)—C(38) | 127.5(3) |
| | | C(44)—C(45)—O(8) | 120.1(3) |
| O(7)—C(42)—C(43) | 113.0(3) | C(45)—C(46)—C(47) | 119.5(3) |
| O(7)—C(42)—C(47) | 125.4(3) | C(46)—C(47)—C(42) | 119.0(3) |
| C(43)—C(42)—C(47) | 121.6(3) | C(42)—C(43)—C(44) | 119.4(3) | F(5)—C(48)—F(6) | 107.9(4) |
| C(42)—C(43)—C(38) | 107.3(3) | F(5)—C(48)—O(8) | 114.1(4) |
| C(44)—C(43)—C(38) | 133.3(3) | F(6)—C(48)—O(8) | 109.6(4) |
| C(43)—C(44)—C(45) | 118.3(3) | F(5)—C(48)—F(4) | 105.8(4) |
| C(46)—C(45)—C(44) | 122.0(3) | F(6)—C(48)—F(4) | 106.5(4) |
| C(46)—C(45)—O(8) | 117.7(3) | O(8)—C(48)—F(4) | 112.5(4) |

TABLE 4

Anisotropic displacement parameters ($Å^2 × 10^3$) for 2. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| O(1) | 37(1) | 89(2) | 56(2) | 6(1) | 7(1) | −7(1) |
| O(2) | 42(1) | 104(2) | 52(1) | 19(1) | −6(1) | −32(1) |
| O(3) | 67(2) | 62(2) | 45(2) | −2(1) | 2(1) | −19(1) |
| O(4) | 62(2) | 54(1) | 63(2) | 9(1) | −15(1) | −26(1) |
| O(5) | 40(1) | 73(2) | 51(1) | 11(1) | −7(1) | −8(1) |
| O(6) | 34(1) | 84(2) | 48(1) | 13(1) | −11(1) | −14(1) |
| O(7) | 92(2) | 67(2) | 43(2) | −9(1) | 2(1) | −44(1) |
| O(8) | 59(2) | 52(1) | 65(2) | 8(1) | −2(1) | −21(1) |
| F(1) | 104(2) | 158(3) | 116(3) | 61(2) | 12(2) | −46(2) |
| F(2) | 66(1) | 85(2) | 119(2) | 0(2) | −22(1) | −15(1) |
| F(3) | 90(2) | 105(2) | 189(3) | −55(2) | −3(2) | −55(2) |
| F(4) | 166(3) | 185(4) | 120(3) | 63(3) | −81(2) | −92(2) |
| F(5) | 68(2) | 142(3) | 254(5) | −83(3) | 28(3) | −37(2) |
| F(6) | 110(2) | 105(2) | 138(3) | 9(2) | −10(2) | −74(2) |
| N(1) | 53(2) | 72(2) | 49(2) | −3(2) | 8(1) | −24(2) |

TABLE 4-continued

Anisotropic displacement parameters (Å² × 10³) for 2. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| N(2) | 39(1) | 46(2) | 38(1) | −3(1) | 1(1) | −15(1) |
| N(3) | 34(1) | 54(2) | 37(1) | 3(1) | −6(1) | −13(1) |
| N(4) | 43(1) | 76(2) | 34(2) | 7(1) | −9(1) | −22(1) |
| N(5) | 89(3) | 103(3) | 49(2) | 18(2) | −8(2) | −22(2) |
| N(6) | 49(2) | 49(2) | 35(2) | −4(1) | 1(1) | −10(1) |
| N(7) | 28(1) | 46(1) | 36(1) | 1(1) | −2(1) | −11(1) |
| N(8) | 36(1) | 49(2) | 36(1) | 1(1) | 3(1) | −15(1) |
| C(1) | 48(2) | 77(2) | 43(2) | −7(2) | 7(2) | −25(2) |
| C(2) | 55(2) | 48(2) | 38(2) | −7(2) | 4(2) | −17(2) |
| C(3) | 73(2) | 58(2) | 46(2) | −1(2) | 6(2) | −16(2) |
| C(4) | 46(2) | 55(2) | 49(2) | 4(2) | −2(2) | −15(2) |
| C(5) | 38(2) | 39(2) | 40(2) | −2(1) | 2(1) | −13(1) |
| C(6) | 37(2) | 56(2) | 51(2) | 8(2) | −5(1) | −10(2) |
| C(7) | 31(2) | 68(2) | 51(2) | 10(2) | −2(1) | −14(2) |
| C(8) | 32(2) | 54(2) | 41(2) | −2(1) | −1(1) | −17(1) |
| C(9) | 36(2) | 54(2) | 44(2) | −4(2) | −2(1) | −16(2) |
| C(10) | 37(2) | 89(3) | 45(2) | 10(2) | −10(1) | −13(2) |
| C(11) | 44(2) | 114(3) | 44(2) | 9(2) | −12(2) | −26(2) |
| C(12) | 41(2) | 61(2) | 43(2) | 1(2) | −3(1) | −20(2) |
| C(13) | 62(2) | 64(2) | 39(2) | 7(2) | −12(2) | −27(2) |
| C(14) | 56(2) | 54(2) | 36(2) | 6(1) | −4(1) | −23(2) |
| C(15) | 86(3) | 61(2) | 49(2) | 8(2) | −6(2) | −25(2) |
| C(16) | 64(2) | 60(2) | 46(2) | 8(2) | −7(2) | −22(2) |
| C(17) | 70(3) | 89(3) | 70(3) | 0(2) | −5(2) | −19(2) |
| C(18) | 56(2) | 57(2) | 43(2) | −3(2) | 0(2) | −26(2) |
| C(19) | 54(2) | 54(2) | 36(2) | 2(1) | −5(1) | −27(2) |
| C(20) | 59(2) | 56(2) | 41(2) | 1(2) | −6(2) | −30(2) |
| C(21) | 54(2) | 44(2) | 56(2) | 3(2) | −10(2) | −22(2) |
| C(22) | 73(2) | 66(2) | 39(2) | 5(2) | −14(2) | −33(2) |
| C(23) | 77(3) | 70(2) | 39(2) | −5(2) | −7(2) | −31(2) |
| C(24) | 65(3) | 63(2) | 78(3) | 3(2) | −9(2) | −26(2) |
| C(25) | 61(2) | 103(3) | 48(2) | 16(2) | −4(2) | −8(2) |
| C(26) | 87(3) | 59(2) | 38(2) | −2(2) | 10(2) | −25(2) |
| C(27) | 131(4) | 87(3) | 61(3) | 14(2) | 16(3) | −32(3) |
| C(28) | 63(2) | 76(3) | 48(2) | 11(2) | 14(2) | −15(2) |
| C(29) | 46(2) | 44(2) | 33(2) | −5(1) | −1(1) | −14(2) |
| C(30) | 36(2) | 65(2) | 41(2) | −3(2) | 6(1) | −17(2) |
| C(31) | 29(1) | 63(2) | 44(2) | −2(2) | −2(1) | −12(1) |
| C(32) | 29(1) | 41(2) | 37(2) | 0(1) | −3(1) | −10(1) |
| C(33) | 38(2) | 41(2) | 40(2) | −2(1) | −4(1) | −10(1) |
| C(34) | 26(1) | 53(2) | 50(2) | −1(2) | 2(1) | −10(1) |
| C(35) | 34(2) | 56(2) | 45(2) | 0(2) | −2(1) | −18(1) |
| C(36) | 36(2) | 45(2) | 37(2) | −2(2) | −1(1) | −11(1) |
| C(37) | 46(2) | 52(2) | 46(2) | 5(2) | 4(1) | −12(2) |
| C(38) | 49(2) | 47(2) | 40(2) | −1(1) | 3(1) | −19(2) |
| C(39) | 75(2) | 48(2) | 51(2) | 1(2) | 3(2) | −14(2) |
| C(40) | 72(2) | 59(2) | 41(2) | −2(2) | 5(2) | −34(2) |
| C(41) | 113(4) | 95(3) | 80(3) | −8(2) | 8(3) | −70(3) |
| C(42) | 63(2) | 47(2) | 36(2) | −1(2) | 0(1) | −25(2) |
| C(43) | 46(2) | 44(2) | 38(2) | −2(2) | 3(1) | −14(2) |
| C(44) | 47(2) | 47(2) | 40(2) | −1(1) | 2(1) | −15(2) |
| C(45) | 54(2) | 41(2) | 48(2) | 4(2) | 2(2) | −18(2) |
| C(46) | 76(2) | 61(2) | 40(2) | 3(2) | 7(2) | −29(2) |
| C(47) | 97(3) | 74(3) | 37(2) | −8(2) | 8(2) | −41(2) |
| C(48) | 66(3) | 68(3) | 79(3) | 5(2) | −15(2) | −26(2) |
| O(1W) | 78(2) | 82(2) | 83(2) | 9(2) | 15(2) | −24(2) |
| O(2W) | 152(4) | 250(6) | 138(4) | 1(4) | −35(3) | −31(4) |

TABLE 5

Hydrogen coordinates (×10⁴) and isotropic displacement parameters (Å² × 10³) for 2.

| | x | y | z | U(eq) |
|---|---|---|---|---|
| H(1) | 6316 | 5661 | 4802 | 67 |
| H(3A) | 832 | 8225 | 3259 | 92 |
| H(3B) | 3243 | 7830 | 3036 | 92 |
| H(3C) | 1974 | 9617 | 3364 | 92 |
| H(4) | 298 | 7018 | 4372 | 61 |
| H(6) | −516 | 6658 | 5339 | 60 |
| H(7) | −1411 | 5396 | 6230 | 62 |
| H(10A) | 5614 | 981 | 6486 | 72 |
| H(10B) | 6694 | 2468 | 6509 | 72 |
| H(11A) | 5744 | 1442 | 7447 | 81 |
| H(11B) | 4729 | 3563 | 7339 | 81 |
| H(13A) | 3183 | 239 | 7955 | 64 |
| H(13B) | 737 | 1441 | 7944 | 64 |
| H(15A) | 2898 | 5004 | 8527 | 79 |
| H(15B) | 1323 | 5146 | 7992 | 79 |
| H(17A) | −2547 | 5397 | 8808 | 118 |
| H(17B) | −2238 | 3334 | 8948 | 118 |
| H(17C) | −1975 | 4048 | 8293 | 118 |
| H(20) | 6501 | −411 | 8515 | 59 |
| H(22) | 6781 | −130 | 10249 | 68 |
| H(23) | 3497 | 2226 | 10270 | 72 |
| H(25) | 5893 | −1924 | 5821 | 92 |
| H(27A) | 1411 | −2507 | 7284 | 146 |
| H(27B) | −713 | −1861 | 6942 | 146 |
| H(27C) | −63 | −449 | 7269 | 146 |
| H(28) | −321 | 634 | 5957 | 80 |
| H(30) | −284 | 1862 | 5091 | 58 |
| H(31) | −234 | 3237 | 4159 | 55 |
| H(34A) | 7076 | −171 | 3664 | 53 |
| H(34B) | 7977 | 627 | 4158 | 53 |
| H(35A) | 6544 | 3532 | 3744 | 54 |
| H(35B) | 7942 | 2275 | 3247 | 54 |
| H(37A) | 5395 | 5013 | 2657 | 60 |
| H(37B) | 3415 | 4586 | 2459 | 60 |
| H(39A) | 8972 | 438 | 2032 | 72 |
| H(39B) | 7287 | 272 | 2582 | 72 |
| H(41A) | 3899 | 62 | 1643 | 131 |
| H(41B) | 2544 | 2088 | 1779 | 131 |
| H(41C) | 3555 | 683 | 2296 | 131 |
| H(44) | 7767 | 5913 | 1982 | 54 |
| H(46) | 9253 | 5443 | 259 | 70 |
| H(47) | 8143 | 2964 | 281 | 80 |

Examples 4 and 5
2-{[(1aS,6bS)-3-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (4) and 2-{[(1aR,6bR)-3-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (5)
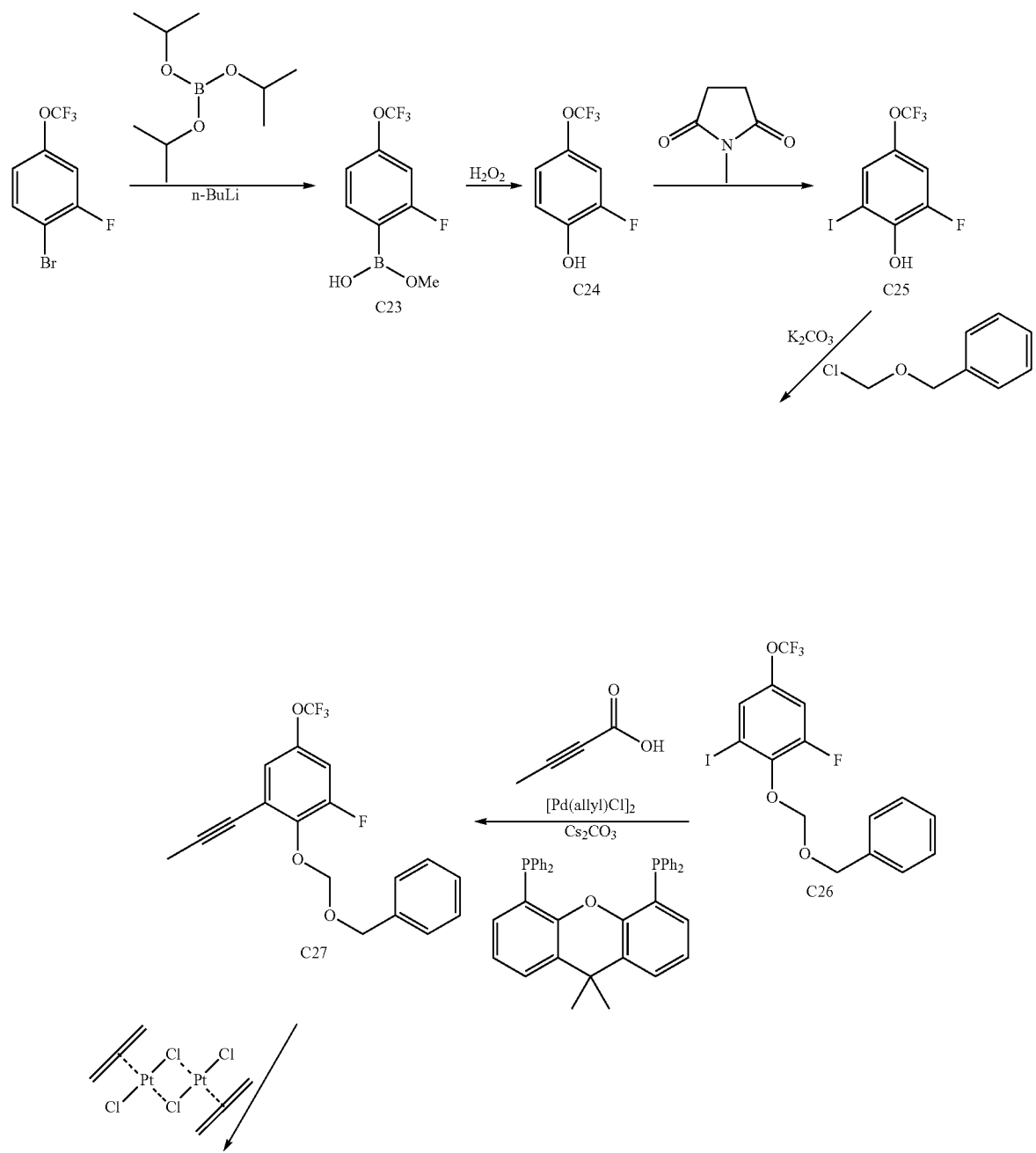

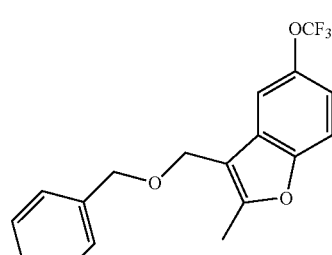
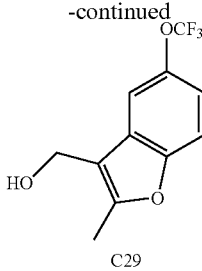
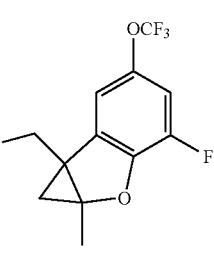
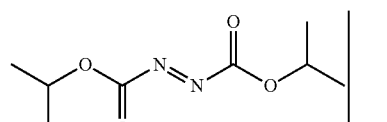
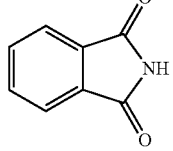
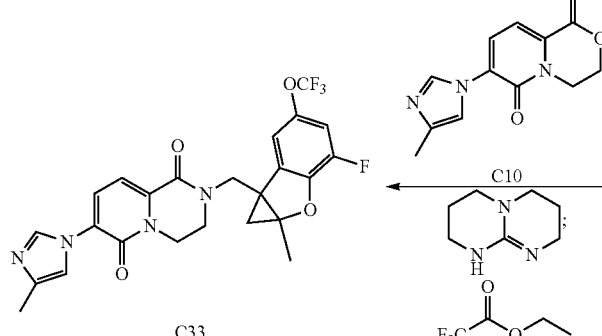
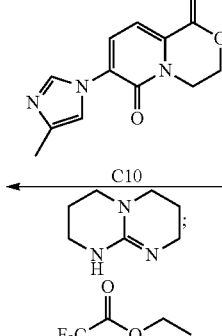
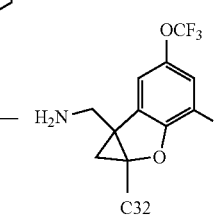
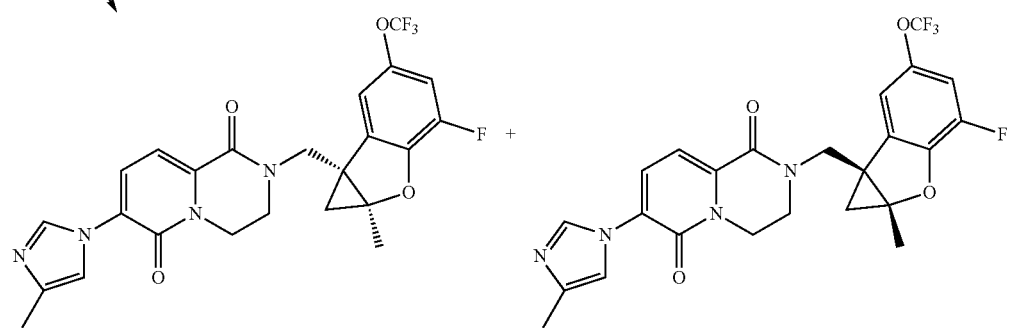

4 + 5

Step 1. Synthesis of [2-fluoro-4-(trifluoromethoxy)phenyl]boronic acid (C23)

Tripropan-2-yl borate (43.6 g, 232 mmol) was added to a solution of 4-bromo-3-fluorophenyl trifluoromethyl ether (50.0 g, 193 mmol) in toluene (400 mL) and tetrahydrofuran (100 mL), and the mixture was cooled to −78° C. n-Butyllithium (2.5 M solution; 92.7 mL, 232 mmol) was then added drop-wise, at a rate that maintained the reaction temperature below −60° C., and the reaction mixture was stirred at −70° C. for 4 hours. After the reaction mixture had been warmed to −20° C., it was quenched via addition of aqueous hydrochloric acid (2 M, 200 mL), and then stirred at room temperature (20° C.) for 40 minutes. The aqueous layer was extracted with ethyl acetate (3×50 mL), and the combined organic layers were washed with saturated aqueous sodium chloride solution (100 mL), dried over sodium sulfate, filtered, and concentrated in vacuo to afford the product (43 g) as a white solid, which was carried directly to the next step.

Step 2. Synthesis of 2-fluoro-4-(trifluoromethoxy)phenol (C24)

To a 20° C. solution of C23 (from the previous step; 43 g, 193 mmol) in dichloromethane (300 mL) was added hydrogen peroxide (30% solution, 99 mL, 1.0 mol), and the reaction mixture was stirred at 20° C. for 2 hours. It was then partitioned between water (200 mL) and dichloromethane (200 mL); the aqueous layer was extracted with dichloromethane (2×100 mL), and the combined organic layers were washed with saturated aqueous sodium chloride solution (200 mL), dried over sodium sulfate, filtered, and concentrated under reduced pressure. Silica gel chromatography (Eluent: 10% ethyl acetate in petroleum ether) provided the product (30 g, which by $^1$H NMR analysis consisted of a 1:0.3 molar ratio of product and ethyl acetate) as a yellow oil. Corrected yield: 26 g, 130 mol, 67% over 2 steps. LCMS m/z 195.0 [M−H$^+$]. $^1$H NMR (400 MHz, CDCl$_3$), product peaks only: δ 6.98-7.05 (m, 2H), 6.94 (br d, half of AB quartet, J=9 Hz, 1H) 5.54 (br d, J=3.3 Hz, 1H).

Step 3. Synthesis of 2-fluoro-6-iodo-4-(trifluoromethoxy)phenol (C25)

A mixture of C24 (9.5 g, 48 mmol) and N-iodosuccinimide (12 g, 53 mmol) in N,N-dimethylformamide (50 mL) was stirred at 25° C. for 4 hours, whereupon it was diluted with water (300 mL) and extracted with tert-butyl methyl ether (3×100 mL). The combined organic layers were washed sequentially with saturated aqueous sodium hydrogen sulfite solution (50 mL) and saturated aqueous sodium chloride solution (50 mL), dried over sodium sulfate, filtered, and concentrated in vacuo. Chromatography on silica gel (Gradient: 0% to 20% ethyl acetate in petroleum ether) afforded the product as a yellow oil. Yield: 12.0 g, 37.3 mmol, 78%. LCMS m/z 320.9 [M−H$^+$]. $^1$H NMR (400 MHz, CDCl$_3$) δ 7.40 (br s, 1H), 7.06 (dd, J=10.2, 2.0 Hz, 1H), 5.78 (br s, 1H).

Step 4. Synthesis of 2-[(benzyloxy)methoxy]-1-fluoro-3-iodo-5-(trifluoromethoxy)benzene (C26)

Benzyl chloromethyl ether (7.66 g, 48.9 mmol) was added to a mixture of C25 (10.5 g, 32.6 mmol) and potassium carbonate (9.01 g, 65.2 mmol) in acetonitrile (100 mL), and the resulting suspension was stirred at 25° C. for 2 hours. The reaction mixture was then diluted with water (400 mL) and extracted with dichloromethane (3×200 mL); the combined organic layers were dried over sodium sulfate, filtered, and concentrated in vacuo. Silica gel chromatography (Gradient: 0% to 20% ethyl acetate in petroleum ether) provided the product as a colorless oil. Yield: 12.3 g, 27.8 mmol, 85%. $^1$H NMR (400 MHz, CDCl$_3$) δ 7.46-7.51 (m, 1H), 7.30-7.41 (m, 5H), 7.06 (ddq, J=10.9, 2.8, 0.7 Hz, 1H), 5.33 (s, 2H), 4.93 (s, 2H).

Step 5. Synthesis of 2-[(benzyloxy)methoxy]-1-fluoro-3-(prop-1-yn-1-yl)-5-(trifluoromethoxy)benzene (C27)

A mixture of C26 (12.0 g, 27.1 mmol), but-2-ynoic acid (4.56 g, 54.2 mmol), and cesium carbonate (13.3 g, 40.8 mmol) in toluene (200 mL) was treated with allylpalladium chloride dimer (497 mg, 1.36 mmol) and 4,5-bis(diphenylphosphino)-9,9-dimethylxanthene (785 mg, 1.36 mmol). The reaction mixture was degassed twice with nitrogen, whereupon it was heated to 80° C. for 16 hours, then filtered through diatomaceous earth. The filtrate was concentrated in vacuo and purified by silica gel chromatography (Gradient: 0% to 30% ethyl acetate in petroleum ether), affording the product as a yellow oil. Yield: 9.2 g, 26 mmol, 96%. $^1$H NMR (400 MHz, CDCl$_3$) δ 7.30-7.40 (m, 5H), 7.05-7.09 (m, 1H), 6.96 (br dd, J=10.7, 2.6 Hz, 1H), 5.35 (s, 2H), 4.91 (s, 2H), 2.07 (s, 3H).

Step 6. Synthesis of 3-[(benzyloxy)methyl]-7-fluoro-2-methyl-5-(trifluoromethoxy)-1-benzofuran (C28)

Di-mu-chloro-dichlorobis(ethylene)diplatinum(II) (840 mg, 1.43 mmol) was added to a solution of C27 (9.2 g, 26 mmol) in toluene (200 mL); the reaction mixture was stirred at 35° C. for 16 hours, then allowed to stand at 25° C. for 2 days. The reaction mixture was concentrated in vacuo, and the residue was purified via silica gel chromatography (Gradient: 0% to 20% ethyl acetate in petroleum ether) to afford the product as a yellow oil. Yield: 6.5 g, 18 mmol, 69%. $^1$H NMR (400 MHz, CDCl$_3$) δ 7.30-7.41 (m, 5H), 7.19-7.23 (m, 1H), 6.91 (br d, J=10.5 Hz, 1H), 4.59 (s, 2H), 4.56 (s, 2H), 2.46 (s, 3H).

Step 7. Synthesis of [7-fluoro-2-methyl-5-(trifluoromethoxy)-1-benzofuran-3-yl]methanol (C29)

To a solution of C28 (3.0 g, 8.5 mmol) in ethanol (150 mL) was added palladium hydroxide on carbon (300 mg), and the reaction mixture was degassed three times with hydrogen. The resulting black suspension was stirred at 60° C. for 16 hours under 50 psi of hydrogen, whereupon it was filtered through diatomaceous earth. The filtrate was concentrated in vacuo; the residue was combined with material from a second reaction (carried out on 3.0 g of C28, 8.5 mmol) and subjected to chromatography on silica gel (Gradient: 0% to 50% ethyl acetate in petroleum ether), affording the product as a white solid. Yield: 3.60 g, 13.6 mmol, 80%. $^1$H NMR (400 MHz, CDCl$_3$) δ 7.28-7.31 (m, 1H), 6.92 (br d, J=10.7 Hz, 1H), 4.77 (br s, 2H), 2.52 (s, 3H).

Step 8. Synthesis of [3-fluoro-1a-methyl-5-(trifluoromethoxy)-1,1a-dihydro-6bH-cyclopropa[b][1]benzofuran-6b-yl]methanol (C30)

Diiodomethane (43.8 g, 164 mmol) and diethylzinc (1 M solution in toluene, 81.8 mmol, 81.8 mL) were added to a solution of C29 (2.70 g, 10.2 mmol) in toluene (200 mL), and the reaction mixture was stirred at 30° C. for 16 hours. It was then added drop-wise to water (200 mL) at 0° C.; the resulting mixture was stirred for 10 minutes, whereupon it was filtered through diatomaceous earth. The aqueous layer was extracted with ethyl acetate (3×100 mL), and the combined organic layers were washed with saturated aqueous sodium chloride solution (100 mL), dried over sodium sulfate, filtered, and concentrated under reduced pressure. Chromatography on silica gel (Gradient: 0% to 30% ethyl acetate in petroleum ether) provided the product as a yellow oil. Yield: 2.0 g, 7.2 mmol, 71%. LCMS m/z 261.0 [M−OH]$^+$. $^1$H NMR (400 MHz, CDCl$_3$) δ 7.10-7.12 (m, 1H), 6.85 (br d, J=10.5 Hz, 1H), 4.12 (d, J=12.0 Hz, 1H), 3.87 (d, J=12.0 Hz, 1H), 1.80 (s, 3H), 1.14 (d, J=6.5 Hz, 1H), 0.70 (d, J=6.5 Hz, 1H).

Step 9. Synthesis of 2-{[3-fluoro-1a-methyl-5-(trifluoromethoxy)-1,1a-dihydro-6bH-cyclopropa[b][1]benzofuran-6b-yl]methyl}-1H-isoindole-1,3(2H)-dione (C31)

Diisopropyl azodicarboxylate (640 mg, 3.16 mmol) was added drop-wise to a mixture of C30 (800 mg, 2.88 mmol), 1H-isoindole-1,3(2H)-dione (465 mg, 3.16 mmol), and triphenylphosphine (830 mg, 3.16 mmol) in tetrahydrofuran (60 mL). The reaction mixture was stirred at 25° C. for 20 hours, whereupon it was concentrated in vacuo. Silica gel chromatography (Gradient: 0% to 20% ethyl acetate in petroleum ether) provided the product as a colorless oil. Yield: 880 mg, 2.16 mmol, 75%. $^1$H NMR (400 MHz, CDCl$_3$) δ 7.86-7.91 (m, 2H), 7.73-7.78 (m, 2H), 7.46-7.49 (m, 1H), 6.81 (br d, J=10.3 Hz, 1H), 4.24 (d, J=15.2 Hz, 1H), 3.97 (d, J=15.3 Hz, 1H), 1.96 (s, 3H), 1.19 (d, J=6.6 Hz, 1H), 0.61 (d, J=6.8 Hz, 1H).

Step 10. Synthesis of 1-[3-fluoro-1a-methyl-5-(trifluoromethoxy)-1,1a-dihydro-6bH-cyclopropa[b][1]benzofuran-6b-yl]methanamine (C32)

To a solution of C31 (500 mg, 1.2 mmol) in methanol (30 mL) was added hydrazine monohydrate (50% aqueous solution, 5 mL, 50 mmol), and the reaction mixture was stirred at 25° C. for 16 hours. After solvent had been removed in vacuo, the residue was diluted with dichloromethane (5 mL) and filtered; the filtrate was concentrated under reduced pressure to afford the product as a colorless oil. Yield: 300 mg, 1.1 mmol, 92%. $^1$H NMR (400 MHz, DMSO-d$_6$) δ 7.39-7.43 (m, 1H), 7.21 (br d, J=10.9 Hz, 1H), 3.15 (d, J=13.8 Hz, 1H), 2.80 (d, J=13.9 Hz, 1H), 1.71 (s, 3H), 1.17 (d, J=6.3 Hz, 1H), 0.50 (d, J=6.3 Hz, 1H).

Step 11. Synthesis of 2-{[3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (C33)

1,3,4,6,7,8-Hexahydro-2H-pyrimido[1,2-a]pyrimidine (191 mg, 1.37 mmol) was added to a suspension of C10 (252 mg, 1.03 mmol) and C32 (190 mg, 0.685 mmol) in N,N-dimethylformamide (5 mL), and the reaction mixture was stirred at 25° C. for 30 minutes. Ethyl trifluoroacetate (386 mg, 2.72 mmol) was then added drop-wise over 5 minutes at 25° C., whereupon the reaction mixture was stirred at 60° C. for 1 hour, cooled, and combined with similar material derived from a second reaction (carried out on 42.2 mg of C32, 0.152 mmol). The mixture was diluted with aqueous sodium hydroxide solution (1 M, 5 mL) and saturated aqueous sodium chloride solution (5 mL), and extracted with dichloromethane (3×5 mL). The combined organic layers were dried over sodium sulfate, filtered, and concentrated in vacuo. Purification via silica gel chromatography (Gradient: 0% to 10% methanol in dichloromethane) provided the racemic product as a yellow gum. Yield: 180 mg, 0.357 mmol, 43%. LCMS m/z 505.2 [M+H]$^+$. $^1$H NMR (400 MHz, CDCl$_3$) δ 8.22 (br s, 1H), 7.45 (d, J=7.6 Hz, 1H), 7.29 (d, J=7.8 Hz, 1H), 7.12 (br s, 1H), 7.04-7.08 (m, 1H), 6.85 (br d, J=10 Hz, 1H), 5.06 (d, J=15.2 Hz, 1H), 4.23 (dd, J=5.9, 5.6 Hz, 2H), 3.57 (ddd, half of ABXY pattern, J=13, 6, 5 Hz, 1H), 3.48 (ddd, half of ABXY pattern, J=13, 6, 6 Hz, 1H), 3.16 (d, J=15.2 Hz, 1H), 2.28 (d, J=1Hz, 3H), 1.89 (s, 3H), 1.07 (d, J=6.8 Hz, 1H), 0.76 (d, J=6.6 Hz, 1H).

Step 12. Isolation of 2-{[(1aS,6bS)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (4) and 2-{[(1aR,6bR)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (5)

Racemate C33 (160 mg, 0.32 mmol) was separated into its component enantiomers using supercritical fluid chromatography [Column: Chiral Technologies Chiralpak AD, 10 μm; Mobile phase: 30% (methanol containing 0.1% ammonium hydroxide) in carbon dioxide]. The second-eluting enantiomer was 4, isolated as a white solid. Yield: 71 mg, 0.14 μmol, 44%. LCMS m/z 505.1 [M+H]$^+$. Retention time: 7.68 minutes (Column: Chiral Technologies Chiralpak AD-H, 4.6×250 mm, 5 μm; Mobile phase A: carbon dioxide; Mobile phase B: methanol containing 0.05% diethylamine; Gradient: 5% to 40% B; Flow rate: 2.5 mL/minute). $^1$H NMR (400 MHz, CDCl$_3$) δ 8.22 (br s, 1H), 7.45 (d, J=7.8 Hz, 1H), 7.29 (d, J=7.8 Hz, 1H), 7.12 (br s, 1H), 7.05-7.08 (m, 1H), 6.85 (br d, J=10.2 Hz, 1H), 5.05 (d, J=15.2 Hz, 1H), 4.23 (dd, J=6.2, 5.5 Hz, 2H), 3.57 (ddd, half of ABXY pattern, J=13, 5.5, 5.5 Hz, 1H), 3.48 (ddd, half of ABXY pattern, J=13, 6, 6 Hz, 1H), 3.17 (d, J=15.3 Hz, 1H), 2.28 (br s, 3H), 1.89 (s, 3H), 1.07 (d, J=6.8 Hz, 1H), 0.76 (d, J=6.6 Hz, 1H).

The first-eluting enantiomer, 5, was also obtained as a white solid. Yield: 73 mg, 0.14 μmol, 44%. LCMS m/z 505.2 [M+H]$^+$. Retention time: 6.42 minutes, using the same analytical conditions as those reported above for 4. $^1$H NMR (400 MHz, CDCl$_3$) δ 8.21 (br s, 1H), 7.45 (d, J=7.8 Hz, 1H), 7.29 (d, J=7.8 Hz, 1H), 7.12 (br s, 1H), 7.04-7.08 (m, 1H), 6.85 (br d, J=10.4 Hz, 1H), 5.06 (d, J=15.3 Hz, 1H), 4.23 (dd, J=6.0, 5.6 Hz, 2H), 3.57 (ddd, half of ABXY pattern, J=13, 5.5, 5.5 Hz, 1H), 3.48 (ddd, half of ABXY pattern, J=13, 6, 6 Hz, 1H), 3.16 (d, J=15.3 Hz, 1H), 2.28 (d, J=0.8 Hz, 3H), 1.89 (s, 3H), 1.07 (d, J=6.8 Hz, 1H), 0.76 (d, J=6.8 Hz, 1H).

Examples 6 and 7
2-{[(1aS,6bS)-4-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (6) and 2-{[(1aR,6bR)-4-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (7)
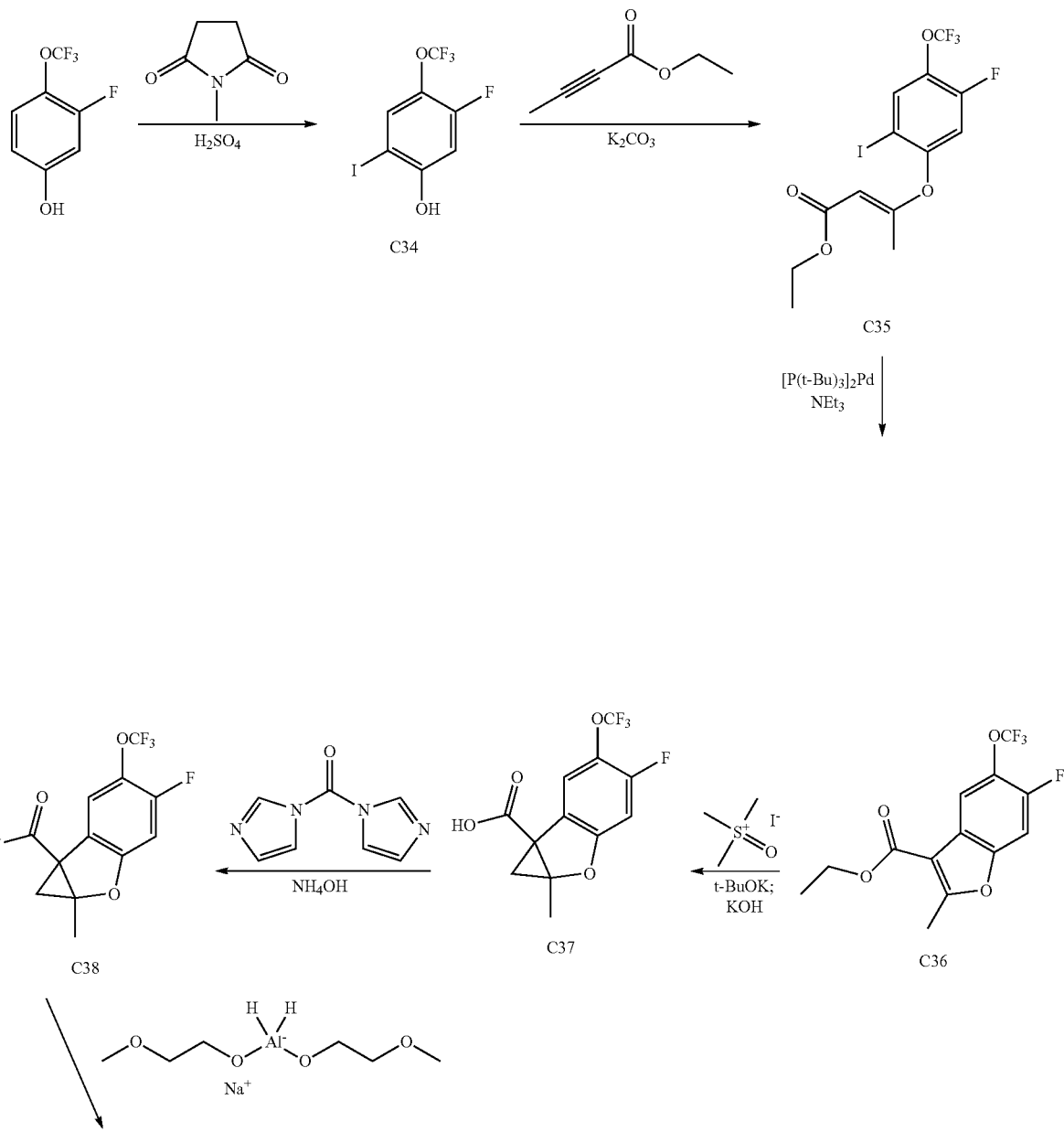

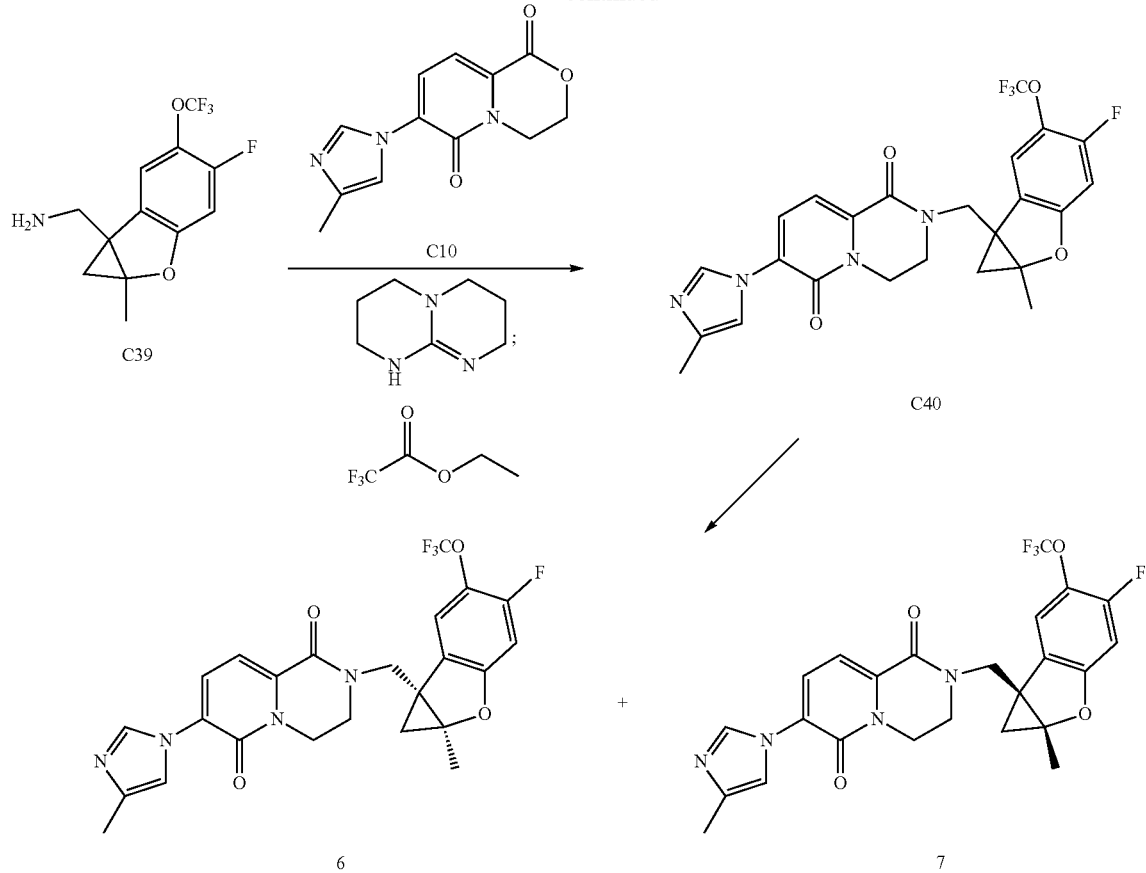

Step 1. Synthesis of 5-fluoro-2-iodo-4-(trifluoromethoxy)phenol (C34)

A mixture of 3-fluoro-4-(trifluoromethoxy)phenol (7.0 g, 36 mmol) and N-iodosuccinimide (95%, 8.45 g, 35.7 mmol) in acetic acid (10 mL) was stirred at room temperature for 5 minutes and then treated with concentrated sulfuric acid (18 M, 0.58 mL, 10.4 mmol). After the reaction mixture had stirred overnight, it was partitioned between water and diethyl ether. The organic layer was washed with water and with 2 M aqueous sodium thiosulfate solution, treated with activated carbon, and dried over magnesium sulfate. The mixture was filtered through a pad of diatomaceous earth and silica gel, and the filtrate was concentrated in vacuo, providing the product as an oil (11.0 g), which by $^1$H NMR analysis contained two molar equivalents of acetic acid. Yield, corrected for acetic acid: 8.0 g, 25 mmol, 70%. GCMS m/z 322.0 [M$^+$]. $^1$H NMR (400 MHz, CDCl$_3$) δ 7.60 (br d, J=8.1 Hz, 1H), 6.88 (d, J=10.9 Hz, 1H).

Step 2. Synthesis of ethyl (2E)-3-[5-fluoro-2-iodo-4-(trifluoromethoxy)phenoxy]but-2-enoate (C35)

A mixture of C34 [from the previous step; 11.0 g (corrected for acetic acid: 8.0 g, 25 mmol)], ethyl but-2-ynoate (4.0 mL, 34 mmol), and potassium carbonate (18.0 g, 130 mmol) in acetonitrile (100 mL) was heated at reflux for 6 hours, then allowed to stir at room temperature overnight. After the reaction mixture had been partitioned between water and diethyl ether, the organic layer was washed with water and with saturated aqueous sodium chloride solution, dried over magnesium sulfate, filtered, and concentrated in vacuo. Chromatography on silica gel (Gradient: 0% to 5% ethyl acetate in heptane) provided the product as an oil. Yield: 8.60 g, 19.8 mmol, 79%. GCMS m/z 434.1 [M$^+$]. $^1$H NMR (400 MHz, CDCl$_3$) δ 7.78 (br d, J=8.0 Hz, 1H), 6.98 (d, J=10.0 Hz, 1H), 4.78 (s, 1H), 4.13 (q, J=7.1 Hz, 2H), 2.53 (s, 3H), 1.25 (t, J=7.1 Hz, 3H).

Step 3. Synthesis of ethyl 6-fluoro-2-methyl-5-(trifluoromethoxy)-1-benzofuran-3-carboxylate (C36)

A stream of nitrogen was bubbled through a solution of C35 (250 mg, 0.576 mmol) in acetonitrile (5 mL) for 10 minutes, whereupon triethylamine (0.40 mL, 2.9 mmol) was added to the solution, followed by bis(tri-tert-butylphosphine)palladium(0) (14.9 mg, 29.2 µmol). The reaction mixture was heated to 90° C. for 20 hours, cooled to room temperature, and partitioned between diethyl ether and water. The organic layer was washed with water, dried over magnesium sulfate, filtered, and concentrated under reduced pressure; silica gel chromatography (Gradient: 0% to 5% ethyl acetate in heptane) provided the product as a white solid. Yield: 148 mg, 0.483 mmol, 84%. $^1$H NMR (400 MHz, CDCl$_3$) δ 7.91 (dq, J=7.7, 1.1 Hz, 1H), 7.30 (d, J=9.3 Hz, 1H), 4.43 (q, J=7.1 Hz, 2H), 2.78 (s, 3H), 1.45 (t, J=7.1 Hz, 3H).

Step 4. Synthesis of 4-fluoro-1a-methyl-5-(trifluoromethoxy)-1,1a-dihydro-6bH-cyclopropa[b][1]benzofuran-6b-carboxylic acid (C37)

A suspension of trimethylsulfoxonium iodide (98%, 1.35 g, 6.01 mmol) in dimethyl sulfoxide (10 mL) was treated with potassium tert-butoxide (645 mg, 5.75 mmol) and stirred at room temperature for 30 minutes. A solution of C36 (1.60 g, 5.22 mmol) in dimethyl sulfoxide (5 mL) and tetrahydrofuran (2 mL) was added; the reaction mixture was stirred for 2 hours, whereupon it was treated with additional trimethylsulfoxonium iodide (98%, 300 mg, 1.3 mmol) and potassium tert-butoxide (130 mg, 1.16 mmol). After 30 minutes, potassium hydroxide (85%, 700 mg, 11 mmol) was added, and stirring was continued for 2 hours. Water (10 mL) was added to the reaction mixture, which was then adjusted to a pH of 4-5 via addition of 1 M aqueous hydrochloric acid. The mixture was extracted with ethyl acetate (3×50 mL), and the combined organic layers were washed with water and with saturated aqueous sodium chloride solution, dried over sodium sulfate, filtered, and concentrated in vacuo. The resulting thick oil was treated with heptane (100 mL), concentrated under reduced pressure, dissolved in diethyl ether, washed twice with water, dried over sodium sulfate, filtered, and concentrated in vacuo. The product was obtained as a solid. Yield: 1.40 g, 4.79 mmol, 92%. $^1$H NMR (400 MHz, CD$_3$OD) δ 7.57 (br d, J=7.9 Hz, 1H), 6.83 (d, J=10.4 Hz, 1H), 1.98 (d, J=6.2 Hz, 1H), 1.83 (s, 3H), 0.92 (d, J=6.3 Hz, 1H).

Step 5. Synthesis of 4-fluoro-1a-methyl-5-(trifluoromethoxy)-1,1a-dihydro-6bH-cyclopropa[b][1]benzofuran-6b-carboxamide (C38)

1,1'-Carbonyldiimidazole (266 mg, 1.64 mmol) was added to a solution of C37 (400 mg, 1.37 mmol) in tetrahydrofuran (10 mL), and the reaction mixture was stirred at room temperature for 30 minutes. Concentrated ammonium hydroxide solution (0.7 mL) was added, and stirring was continued for 1 hour, whereupon the reaction mixture was partitioned between water and diethyl ether. The organic layer was washed with water, dried over sodium sulfate, filtered, and concentrated in vacuo, providing the product as a pasty solid. Yield: 390 mg, 1.34 mmol, 98%. GCMS m/z 291.2 [M$^+$]. $^1$H NMR (400 MHz, DMSO-d$_6$) δ 7.50 (br d, J=7.9 Hz, 1H), 7.41 (br s, 1H), 7.31 (br s, 1H), 7.15 (d, J=10.9 Hz, 1H), 1.96 (d, J=6.6 Hz, 1H), 1.65 (s, 3H), 0.75 (d, J=6.6 Hz, 1H).

Step 6. Synthesis of 1-[4-fluoro-1a-methyl-5-(trifluoromethoxy)-1,1a-dihydro-6bH-cyclopropa[b][1]benzofuran-6b-yl]methanamine (C39)

Sodium bis(2-methoxyethoxy)aluminum hydride (3.3 M solution in toluene; 7.0 mL, 23 mmol) was added to a solution of C38 (1.70 g, 5.84 mmol) in toluene (30 mL). The reaction mixture was stirred at room temperature for 2 hours, whereupon it was cooled in an ice bath and quenched with aqueous sodium hydroxide solution (1 M, 30 mL). The resulting mixture was extracted with diethyl ether; the combined organic layers were washed with saturated aqueous sodium chloride solution, dried over sodium sulfate, filtered, and concentrated in vacuo. Silica gel chromatography (Gradient: 0% to 5% methanol in dichloromethane) afforded the product as a thick oil. Yield: 1.2 g, 4.3 mmol, 74%. GCMS m/z 260.2 [M−NH$_3$]$^+$. $^1$H NMR (400 MHz, CDCl$_3$) δ 7.25-7.31 (m, 1H, assumed; partially obscured by solvent peak), 6.66 (d, J=10.2 Hz, 1H), 3.34 (d, J=14.0 Hz, 1H), 2.87 (d, J=14.0 Hz, 1H), 1.75 (s, 3H), 0.95 (d, J=6.3 Hz, 1H), 0.56 (d, J=6.3 Hz, 1H).

Step 7. Synthesis of 2-{[4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (C40)

Conversion of C39 to the product was carried out using the method described for synthesis of C22 from C21 in Examples 2 and 3. The product was obtained as a white solid. Yield: 560 mg, 1.11 mmol, 97%. LCMS m/z 505.1 [M+H]$^+$. $^1$H NMR (400 MHz, CDCl$_3$) δ 8.22 (d, J=1.2 Hz, 1H), 7.45 (d, J=7.7 Hz, 1H), 7.24-7.31 (m, 2H, assumed; partially obscured by solvent peak), 7.11-7.14 (m, 1H), 6.68 (d, J=10.0 Hz, 1H), 5.06 (d, J=15.1 Hz, 1H), 4.26 (ddd, half of ABXY pattern, J=14.2, 6.3, 4.7 Hz, 1H), 4.20 (ddd, half of ABXY pattern, J=14.3, 8.0, 4.4 Hz, 1H), 3.56 (ddd, half of ABXY pattern, J=13.2, 6.3, 4.5 Hz, 1H), 3.46 (ddd, half of ABXY pattern, J=13.2, 7.9, 4.5 Hz, 1H), 3.12 (d, J=15.2 Hz, 1H), 2.29 (br s, 3H), 1.84 (s, 3H), 1.00 (d, J=6.6 Hz, 1H), 0.68 (d, J=6.6 Hz, 1H).

Step 8. Isolation of 2-{[(1aS,6b5)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (6) and 2-{[(1aR,6bR)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (7)

Separation of C40 (560 mg, 1.1 mmol) into its component enantiomers was carried out via supercritical fluid chromatography [Column: Chiral Technologies Chiralpak AD-H, 5 μm; Mobile phase: 30% (0.2% ammonium hydroxide in methanol) in carbon dioxide]. Each enantiomer was then dissolved in ethyl acetate (15 mL), filtered, and concentrated in vacuo; suspension in diethyl ether followed by filtration provided the products, both as solids. Compound 6 was the second-eluting enantiomer. Yield: 160 mg, 0.317 mg, 28%. LCMS m/z 505.1 [M+H]$^+$. $^1$H NMR (400 MHz, CDCl$_3$) δ 8.22 (s, 1H), 7.45 (d, J=7.7 Hz, 1H), 7.26-7.31 (m, 2H, assumed; partially obscured by solvent peak), 7.13 (br s, 1H), 6.68 (d, J=10.0 Hz, 1H), 5.06 (d, J=15.2 Hz, 1H), 4.26 (ddd, half of ABXY pattern, J=14, 6, 5 Hz, 1H), 4.20 (ddd, half of ABXY pattern, J=14, 8, 4 Hz, 1H), 3.56 (ddd, half of ABXY pattern, J=13, 6, 5 Hz, 1H), 3.46 (ddd, half of ABXY pattern, J=13, 8, 5 Hz, 1H), 3.12 (d, J=15.2 Hz, 1H), 2.29 (s, 3H), 1.84 (s, 3H), 1.00 (d, J=6.6 Hz, 1H), 0.68 (d, J=6.6 Hz, 1H).

Compound 7 was the first-eluting enantiomer. Yield: 180 mg, 0.357 mmol, 31%. LCMS m/z 505.2 [M+H]$^+$. $^1$H NMR (400 MHz, CDCl$_3$) δ 8.22 (s, 1H), 7.45 (d, J=7.7 Hz, 1H), 7.26-7.31 (m, 2H, assumed; partially obscured by solvent peak), 7.13 (br s, 1H), 6.68 (d, J=10.0 Hz, 1H), 5.06 (d, J=15.2 Hz, 1H), 4.26 (ddd, half of ABXY pattern, J=14.5, 6, 5 Hz, 1H), 4.20 (ddd, half of ABXY pattern, J=14.3, 7.8, 4.3 Hz, 1H), 3.56 (ddd, half of ABXY pattern, J=13, 6, 4.5 Hz, 1H), 3.46 (ddd, half of ABXY pattern, J=13, 8, 5 Hz, 1H), 3.12 (d, J=15.1 Hz, 1H), 2.29 (s, 3H), 1.84 (s, 3H), 1.00 (d, J=6.6 Hz, 1H), 0.68 (d, J=6.6 Hz, 1H).

Examples 8 and 9
2-{[(1aS,6bS)-4-Fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione (8) and 2-{[(1aR,6bR)-4-Fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione (9)
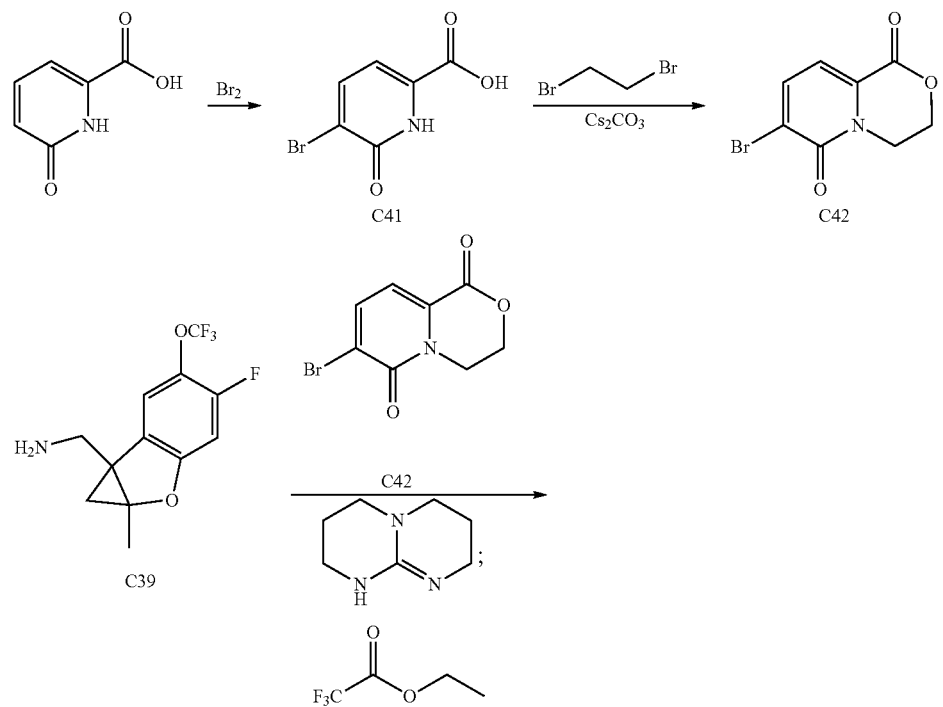
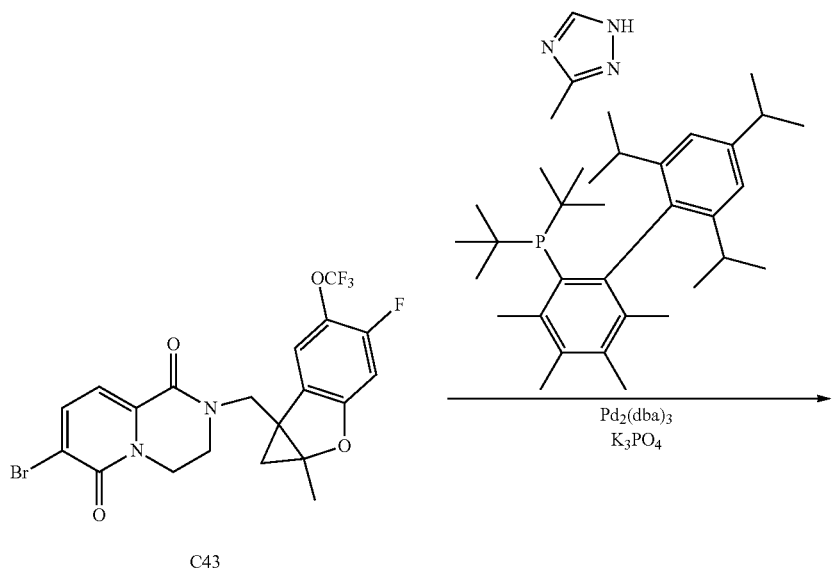

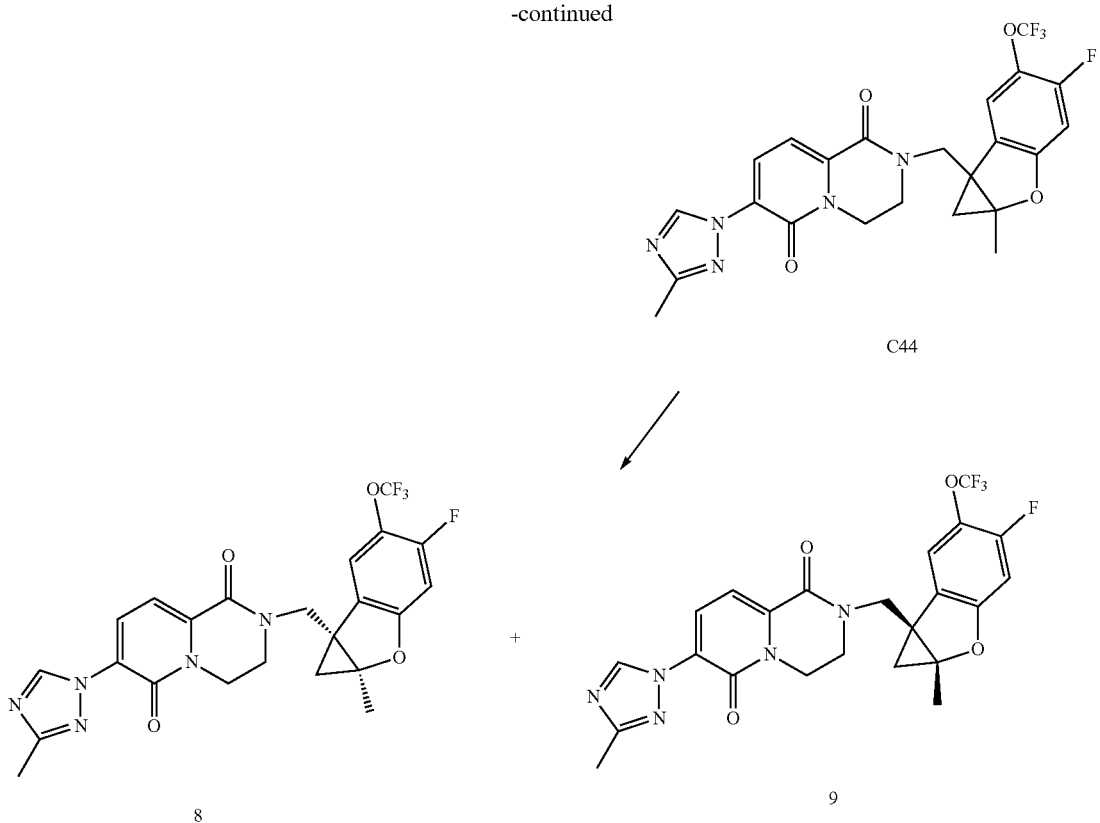

Step 1. Synthesis of 5-bromo-6-oxo-1,6-dihydropyridine-2-carboxylic acid (C41)

Bromine (115 g, 720 mmol) was added drop-wise to a suspension of 6-oxo-1,6-dihydropyridine-2-carboxylic acid (25 g, 180 mmol) in acetic acid (400 mL). The reaction mixture was heated to 80° C. for 16 hours, whereupon it was concentrated to dryness under reduced pressure. The residue was triturated with tert-butyl methyl ether (200 mL) and filtered; the filter cake was washed with tert-butyl methyl ether (3×100 mL) to provide the product as a gray solid. Yield: 39.0 g, 179 mmol, 99%. $^1$H NMR (400 MHz, DMSO-$d_6$) δ 8.03 (d, J=7.3 Hz, 1H), 6.83 (d, J=7.3 Hz, 1H).

Step 2. Synthesis of 7-bromo-3,4-dihydropyrido[2,1-c][1,4]oxazine-1,6-dione (C42)

This transformation was carried out in four identical batches. 1,2-Dibromoethane (9.48 g, 50.5 mmol) was added to a suspension of C41 (10.0 g, 45.9 mmol) and cesium carbonate (37.4 g, 115 mmol) in N,N-dimethylformamide (50 mL). The reaction mixture was stirred at 95° C. for 2 hours, whereupon it was cooled to about 30° C. and combined with the other three batches. This material was poured into dichloromethane (600 mL) and stirred at room temperature for 10 minutes, then filtered. The filter cake was washed with dichloromethane (200 mL), and the combined filtrates were concentrated to dryness under reduced pressure. The residue was mixed with dichloromethane (100 mL), stirred at 25° C. for 20 minutes, and then filtered. The collected solid was dissolved in a mixture of dichloromethane (500 mL) and methanol (30 mL), and filtered through silica gel (10 g). This filtrate was concentrated in vacuo and triturated with a mixture of dichloromethane (50 mL) and tert-butyl methyl ether (50 mL), affording the product as a pale yellow solid. Yield: 13 g, 53 mmol, 29%. LCMS m/z 245.8 [M+H]$^+$. $^1$H NMR (400 MHz, CDCl$_3$) δ 7.91 (d, J=7.5 Hz, 1H), 7.14 (d, J=7.5 Hz, 1H), 4.64 (dd, J=5.3, 5.1 Hz, 2H), 4.36 (dd, J=5.3, 5.1 Hz, 2H).

Step 3. Synthesis of 7-bromo-2-{[4-fluoro-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione (C43)

1,3,4,6,7,8-Hexahydro-2H-pyrimido[1,2-a]pyrimidine (97%, 932 mg, 6.49 mmol) was added to a mixture of C39 (1.20 g, 4.33 mmol) and C42 (1.37 g, 5.61 mmol) in N,N-dimethylformamide (5 mL). The reaction mixture was stirred at room temperature for 2 hours, then treated with ethyl trifluoroacetate (1.3 mL, 10.9 mmol). After 1 hour, aqueous sodium hydroxide solution (1 M, 10 mL) was added, and stirring was continued for 15 minutes. The mixture was then extracted with ethyl acetate, and the combined organic layers were washed with water, dried over sodium sulfate, filtered, and concentrated in vacuo. Chromatography on silica gel (Gradient: 30% to 100% ethyl acetate in heptane) provided the product as an oil. Yield: 1.76 g, 3.50 mmol, 81%. LCMS m/z 503.3, 505.3 [M+H]$^+$. $^1$H NMR (400 MHz, CDCl$_3$) δ 7.86 (d, J=7.6 Hz, 1H), 7.24-7.28 (m, 1H, assumed; partially obscured by solvent peak), 7.07 (d, J=7.6 Hz, 1H), 6.67 (d, J=9.9 Hz, 1H), 5.01 (d, J=15.2 Hz, 1H), 4.18 (dd, J=6.0, 5.8 Hz, 2H), 3.52 (ddd, half of ABXY pattern, J=13, 5.5, 5.5 Hz, 1H), 3.42 (ddd, half of ABXY pattern, J=13, 6, 6 Hz, 1H), 3.11 (d, J=15.2 Hz, 1H), 1.82 (s, 3H), 0.98 (d, J=6.6 Hz, 1H), 0.67 (d, J=6.6 Hz, 1H).

Step 4. Synthesis of 2-{[4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione (C44)

A mixture of tris(dibenzylideneacetone)dipalladium(0) (98%, 94.7 mg, 0.101 mmol) and di-tert-butyl[3,4,5,6-tetramethyl-2',4',6'-tri(propan-2-yl)biphenyl-2-yl]phosphane (95%, 103 mg, 0.203 mmol) in toluene (10 mL) was degassed with nitrogen for 5 minutes, then heated at 125° C. for 3 minutes. In a separate flask, a mixture of C43 (1.70 g, 3.38 mmol), 3-methyl-1H-1,2,4-triazole (561 mg, 6.75 mmol), and potassium phosphate (1.48 g, 6.97 mmol) in toluene (10 mL) and 1,4-dioxane (10 mL) was degassed with nitrogen for 10 minutes. The catalyst solution was transferred to the reaction flask via syringe, and the reaction mixture was heated at 125° C. for 2 hours, whereupon it was partitioned between water and ethyl acetate. The organic layer was dried over sodium sulfate, filtered, and concentrated in vacuo; silica gel chromatography (Gradient: 50% to 100% ethyl acetate in heptane) provided the product as an off-white solid. Yield: 1.3 g, 2.6 mmol, 77%. LCMS m/z 506.4 [M+H]$^+$. $^1$H NMR (400 MHz, CDCl$_3$), characteristic peaks: δ 9.52 (br s, 1H), 8.21 (d, J=7.9 Hz, 1H), 7.38 (d, J=7.8 Hz, 1H), 7.25-7.31 (m, 1H, assumed; partially obscured by solvent peak), 6.68 (d, J=10.0 Hz, 1H), 5.05 (d, J=15.2 Hz, 1H), 4.20-4.32 (m, 2H), 3.53-3.62 (m, 1H), 3.14 (d, J=15.2 Hz, 1H), 2.49 (s, 3H), 1.84 (s, 3H), 1.00 (d, J=6.6 Hz, 1H), 0.69 (d, J=6.5 Hz, 1H).

Step 5. Isolation of 2-{[(1aS,6bS)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione (8) and 2-{[(1aR,6bR)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione (9)

Compound C44 (1.3 g, 2.6 mmol) was separated into its component enantiomers via supercritical fluid chromatography [Column: Phenomenex Lux Cellulose-4, 5 μm; Mobile phase: 30% (1:1 acetonitrile/methanol) in carbon dioxide]. The individual enantiomers from the separation were dissolved in ethyl acetate (10 mL), passed through a syringe filter, concentrated in vacuo, and then precipitated with diethyl ether; both enantiomers were obtained as solids. Example 8 was the second-eluting enantiomer. Yield: 415 mg, 0.821 mmol, 32%. LCMS m/z 506.4 [M+H]$^+$. $^1$H NMR (400 MHz, CDCl$_3$) δ 9.53 (br s, 1H), 8.21 (d, J=7.9 Hz, 1H), 7.38 (d, J=7.8 Hz, 1H), 7.29 (dq, J=7.5, 1.0 Hz, 1H), 6.68 (d, J=10.0 Hz, 1H), 5.05 (d, J=15.2 Hz, 1H), 4.20-4.32 (m, 2H), 3.57 (ddd, half of ABXY pattern, J=13.2, 6.0, 4.9 Hz, 1H), 3.44-3.51 (m, 1H), 3.14 (d, J=15.2 Hz, 1H), 2.48 (s, 3H), 1.84 (s, 3H), 1.00 (d, J=6.6 Hz, 1H), 0.69 (d, J=6.6 Hz, 1H).

The first-eluting enantiomer was compound 9. Yield: 412 mg, 0.815 mmol, 31%. LCMS m/z 506.4 [M+H]$^+$. $^1$H NMR (400 MHz, CDCl$_3$) δ 9.52 (br s, 1H), 8.21 (d, J=7.9 Hz, 1H), 7.38 (d, J=7.9 Hz, 1H), 7.28 (dq, J=7.6, 1.0 Hz, 1H), 6.68 (d, J=10.0 Hz, 1H), 5.05 (d, J=15.2 Hz, 1H), 4.20-4.32 (m, 2H), 3.57 (ddd, half of ABXY pattern, J=13.2, 6.0, 4.9 Hz, 1H), 3.44-3.51 (m, 1H), 3.14 (d, J=15.2 Hz, 1H), 2.49 (s, 3H), 1.84 (s, 3H), 1.00 (d, J=6.6 Hz, 1H), 0.69 (d, J=6.7 Hz, 1H).

Examples 10 and 11

2-{[(1aS,6bS)-4-Chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (10) and 2-{[(1aR,6bR)-4-Chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (11)

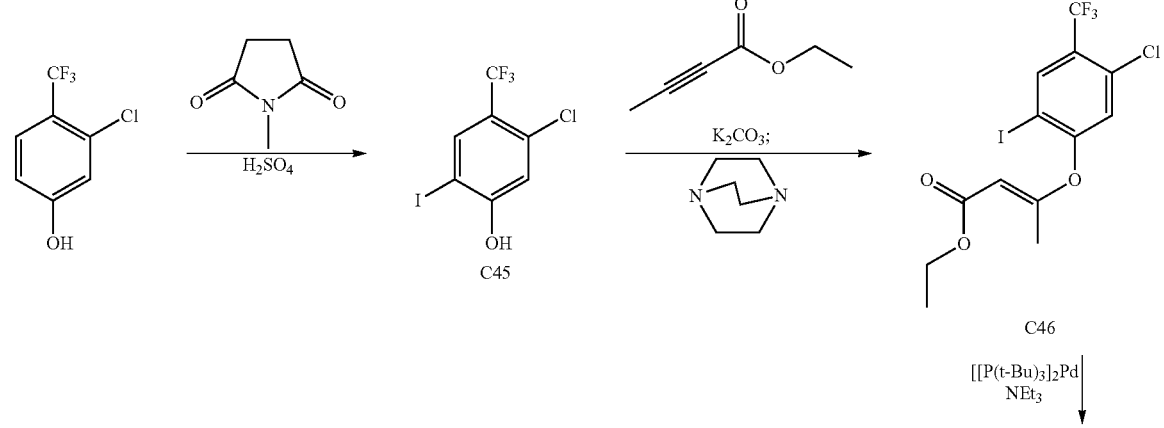

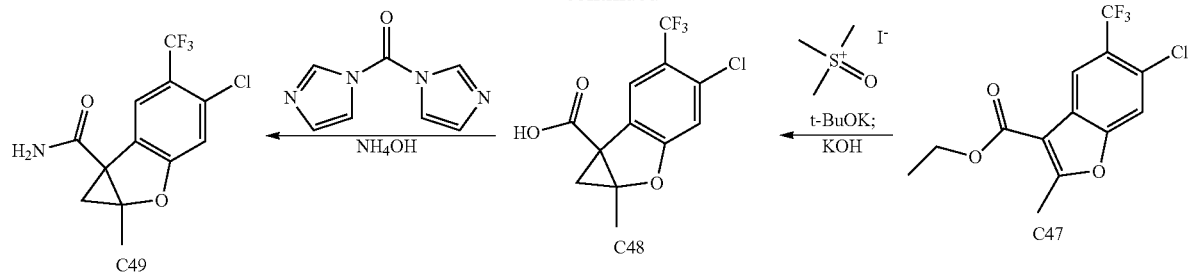

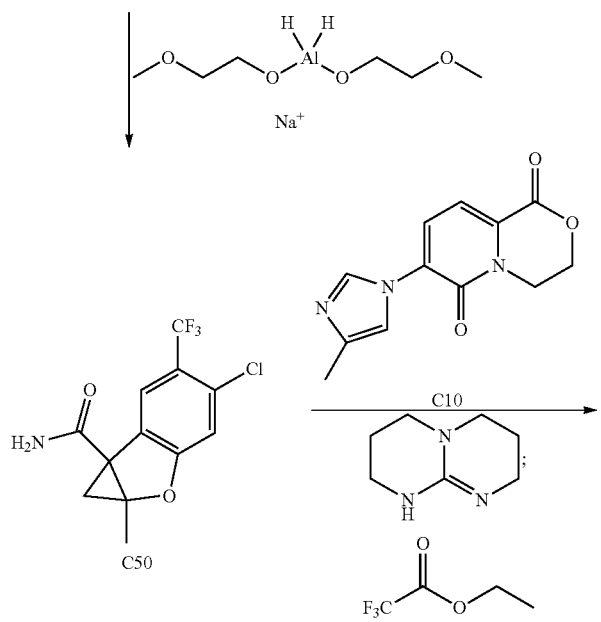

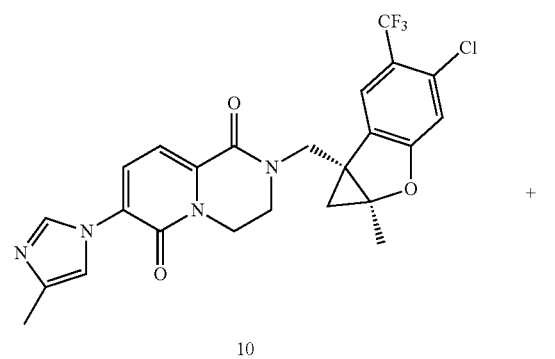

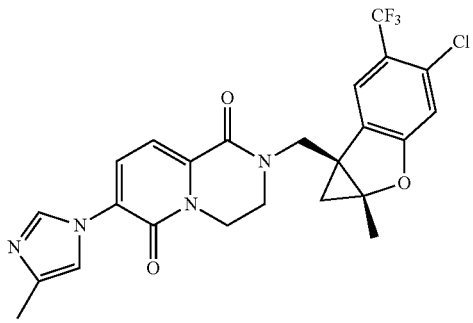

Step 1. Synthesis of 5-chloro-2-iodo-4-(trifluoromethyl)phenol (C45)

A mixture of 3-chloro-4-(trifluoromethyl)phenol (3.00 g, 15.3 mmol) and N-iodosuccinimide (95%, 3.61 g, 15.2 mmol) in acetic acid (10 mL) was stirred for 5 minutes, whereupon sulfuric acid (18 M, 0.25 mL, 4.5 mmol) was added. After the reaction mixture had been stirred at room temperature for 2 days, it was partitioned between diethyl ether and water. The organic layer was washed with water and with 2 M aqueous sodium thiosulfate solution, then treated with activated carbon and dried over magnesium sulfate. The mixture was filtered through a pad of diatomaceous earth and silica gel, and the filtrate was concentrated in vacuo to afford an oil (4.9 g) containing product, acetic acid, and solvent. This material was taken into the following step without additional purification. GCMS m/z 322.0 [M+]. $^1$H NMR (400 MHz, CDCl$_3$), product peaks only: δ 7.95 (s, 1H), 7.12 (s, 1H).

Step 2. Synthesis of ethyl (2E)-3-[5-chloro-2-iodo-4-(trifluoromethyl)phenoxy]but-2-enoate (C46)

A mixture of C45 (from the previous step; 4.9 g, mmol) and potassium carbonate (10.5 g, 76.0 mmol) in acetonitrile (100 mL) was stirred for 10 minutes. Ethyl but-2-ynoate (2.0 mL, 17 mmol) was added, and the reaction mixture was heated at reflux overnight; GCMS analysis indicated partial conversion to product. The reaction mixture was partitioned between 1 M aqueous hydrochloric acid and a 1:1 mixture of diethyl ether and heptane. The organic layer was washed with water and with saturated aqueous sodium chloride solution, then dried over sodium sulfate, filtered, and concentrated in vacuo. Silica gel chromatography (Gradient: 0% to 25% ethyl acetate in heptane) afforded recovered C45 (2.84 g) and a mixture of product and the des-iodo analogue (0.88 g). The recovered C45 was resubjected to the reaction conditions and worked up in the same manner, affording the product (1.2 g) as a thick oil that slowly solidified, and recovered C45 (1.6 g). A portion of this C45 (1.2 g, 3.7 mmol) was dissolved in toluene (10 mL) and treated with 1,4-diazabicyclo[2.2.2]octane (411 mg, 3.66 mmol), followed by ethyl but-2-ynoate (1 mL, 9 mmol). The reaction mixture was heated at 100° C. for 18 hours, then cooled to room temperature and combined with the 0.88 g of material isolated above. This mixture was partitioned between diethyl ether and 1 M aqueous hydrochloric acid; the organic layer was washed with 1 M aqueous hydrochloric acid and with water, then dried over magnesium sulfate, filtered, and concentrated under reduced pressure. Chromatography on silica gel (Gradient: 0% to 5% ethyl acetate in heptane) afforded additional product (2.0 g) as an oil. Combined yield: 3.2 g, 7.4 mmol, 48% over 2 steps. GCMS m/z 434.1 [M$^+$]. $^1$H NMR (400 MHz, CDCl$_3$) δ 8.14 (s, 1H), 7.20 (br s, 1H), 4.80-4.82 (m, 1H), 4.14 (q, J=7.1 Hz, 2H), 2.54 (d, J=0.6 Hz, 3H), 1.26 (t, J=7.1 Hz, 3H).

Step 3. Synthesis of ethyl 6-chloro-2-methyl-5-(trifluoromethyl)-1-benzofuran-3-carboxylate (C47)

A solution of C46 (3.10 g, 7.13 mmol) in acetonitrile (20 mL) was purged with nitrogen for 10 minutes, then treated with triethylamine (5.0 mL, 36 mmol), followed by bis(tri-tert-butylphosphine)palladium(0) (184 mg, 0.360 mmol). The reaction mixture was heated at 90° C. for 1 hour, whereupon it was partitioned between diethyl ether and 1 M aqueous hydrochloric acid. The organic layer was washed with water and with saturated aqueous sodium chloride solution, dried over magnesium sulfate, and treated with activated carbon. The mixture was filtered through a pad of diatomaceous earth, and the filtrate was concentrated in vacuo. Silica gel chromatography (Gradient: 0% to 5% ethyl acetate in heptane) afforded the product as an off-white/tan solid. Yield: 1.00 g, 3.26 mmol, 46%. GCMS m/z 306.1 [M$^+$]. $^1$H NMR (400 MHz, CDCl$_3$) δ 8.33 (s, 1H), 7.60 (s, 1H), 4.44 (q, J=7.1 Hz, 2H), 2.80 (s, 3H), 1.46 (t, J=7.1 Hz, 3H).

Step 4. Synthesis of 4-chloro-1a-methyl-5-(trifluoromethyl)-1,1a-dihydro-6bH-cyclopropa[b][1]benzofuran-6b-carboxylic acid (C48)

A suspension of trimethylsulfoxonium iodide (98%, 820 mg, 3.7 mmol) in dimethyl sulfoxide (5 mL) was treated with potassium tert-butoxide (1 M solution in tetrahydrofuran; 3.59 mL, 3.59 mmol) and allowed to stir at room temperature for 20 minutes. A solution of C47 (1.00 g, 3.26 mmol) in dimethyl sulfoxide (5 mL) and tetrahydrofuran (3 mL) was added, and stirring was continued for 1.5 hours. At this point, additional trimethylsulfoxonium iodide (98%, 125 mg, 0.557 mmol) and potassium tert-butoxide (1 M solution in tetrahydrofuran; 0.5 mL, 0.5 mmol) were introduced, and the reaction was allowed to proceed for 1.5 hours. Crushed potassium hydroxide pellets (85%, 540 mg, 8.2 mmol) were added, and the reaction mixture was stirred for 2 hours; it was then adjusted to a pH of 4-5 via addition of 1 M aqueous hydrochloric acid. The mixture was extracted with ethyl acetate, and the combined organic layers were washed with water and with saturated aqueous sodium chloride solution, dried over sodium sulfate, filtered, and concentrated in vacuo to afford the product as a pasty solid (1.16 g); this material was impure by $^1$H NMR analysis, and was used in the following step without further purification. $^1$H NMR (400 MHz, DMSO-d$_6$), product peaks only: δ 13.2-13.4 (v br s, 1H), 7.94 (s, 1H), 7.35 (s, 1H), 1.97 (d, J=6.4 Hz, 1H), 1.80 (s, 3H), 1.07 (d, J=6.4 Hz, 1H).

Step 5. Synthesis of 4-chloro-1a-methyl-5-(trifluoromethyl)-1,1a-dihydro-6bH-cyclopropa[b][1]benzofuran-6b-carboxamide (C49)

Conversion of C48 (from the previous step; 1.10 g, mmol) to the product was carried out according to the method described for synthesis of C38 from C37 in Examples 6 and 7. The product was isolated as a thick oil (1.1 g), which was impure by $^1$H NMR analysis; this material was taken to the next step without additional purification. GCMS m/z 291.1 [M$^+$]. $^1$H NMR (400 MHz, DMSO-d$_6$), product peaks only: δ 7.76 (s, 1H), 7.33 (s, 1H), 2.03 (d, J=6.6 Hz, 1H), 1.68 (s, 3H), 0.79 (d, J=6.6 Hz, 1H).

Step 6. Synthesis of 1-[4-chloro-1a-methyl-5-(trifluoromethyl)-1,1a-dihydro-6bH-cyclopropa[b][1]benzofuran-6b-yl]methanamine (C50)

Sodium bis(2-methoxyethoxy)aluminum hydride (3.3 M solution in toluene; 4.2 mL, 13.9 mmol) was added to a solution of C49 (from the previous step; 1.0 g, ≤2.8 mmol) in toluene (25 mL) and tetrahydrofuran (5 mL). After 2 hours at room temperature, the reaction mixture was cooled in an ice bath, quenched with aqueous sodium hydroxide solution (1 M, 25 mL, 25 mmol), and extracted with diethyl ether. The organic layer was washed with saturated aqueous sodium chloride solution, dried over sodium sulfate, filtered, and concentrated in vacuo, affording the product as a thick gum (865 mg). By $^1$H NMR analysis, this material was impure; it was used in the following step without additional purification. $^1$H NMR (400 MHz, CDCl$_3$), product peaks only: δ 7.66 (s, 1H), 6.94 (s, 1H), 3.39 (d, J=14.0 Hz, 1H), 2.89 (d, J=14.1 Hz, 1H), 1.77 (s, 3H), 1.01 (d, J=6.4 Hz, 1H), 0.54 (d, J=6.3 Hz, 1H).

Step 7. Synthesis of 2-{[(1aS,6bS)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (10) and 2-{[(1aR,6bR)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (11)

1,3,4,6,7,8-Hexahydro-2H-pyrimido[1,2-a]pyrimidine (97%, 671 mg, 4.68 mmol) was added to a mixture of C50 (from the previous step; 865 mg, ≤2.8 mmol) and C10 (993 mg, 4.05 mmol) in N,N-dimethylformamide (5 mL). After 2 hours, ethyl trifluoroacetate (0.93 mL, 7.8 mmol) was added to the reaction mixture, and stirring was continued for 1 hour. Aqueous sodium hydroxide solution (1 M, 10 mL, 10 mmol) was added and the mixture was stirred for 15 minutes, whereupon it was partitioned between water and ethyl acetate. The organic layer was washed with water, dried over sodium sulfate, filtered, and concentrated in vacuo. After the residue had been purified via chromatography on silica gel (Gradient: 0% to 10% methanol in ethyl acetate), it was triturated with diethyl ether, and the resulting solid (470 mg) was separated into its component enantiomers via supercritical fluid chromatography [Column: Chiral Technologies Chiralpak AD-H, 5 μm; Mobile phase: 20% (1:1 acetonitrile/methanol) in carbon dioxide]. Each enantiomer was then dissolved in ethyl acetate (10 mL) and passed through a syringe filter. The eluents were concentrated in vacuo and triturated with diethyl ether, to afford each product as a solid.

Compound 10 was the second-eluting enantiomer. Yield: 114 mg, 0.226 mmol, 8% over 4 steps. LCMS m/z 505.4, 507.4 [M+H]+. $^1$H NMR (400 MHz, CD$_3$OD) δ 8.31 (br s, 1H), 7.79 (s, 1H), 7.77 (d, J=7.8 Hz, 1H), 7.31 (br s, 1H), 7.27 (d, J=7.8 Hz, 1H), 7.04 (s, 1H), 4.85 (d, J=15.1 Hz, 1H), 4.33 (ddd, half of ABXY pattern, J=14, 6, 4 Hz, 1H), 4.19 (ddd, half of ABXY pattern, J=14, 9, 4 Hz, 1H), 3.73 (ddd, half of ABXY pattern, J=13, 6, 4 Hz, 1H), 3.5-3.58 (m, 1H), 3.50 (d, J=15.3 Hz, 1H), 2.23 (br s, 3H), 1.87 (s, 3H), 1.23 (d, J=6.8 Hz, 1H), 0.63 (d, J=6.7 Hz, 1H).

The first-eluting enantiomer was 11. Yield: 122 mg, 0.242 mmol, 9% over 4 steps. LCMS m/z 505.4, 507.3 [M+H]+. $^1$H NMR (400 MHz, CD$_3$OD) δ 8.30 (br s, 1H), 7.79 (s, 1H), 7.77 (d, J=7.7 Hz, 1H), 7.30 (br s, 1H), 7.27 (d, J=7.7 Hz, 1H), 7.04 (s, 1H), 4.85 (d, J=15.2 Hz, 1H), 4.33 (ddd, half of ABXY pattern, J=14, 6, 4 Hz, 1H), 4.19 (ddd, half of ABXY pattern, J=14, 9, 4 Hz, 1H), 3.73 (ddd, half of ABXY pattern, J=13, 6, 4 Hz, 1H), 3.54 (ddd, half of ABXY pattern, J=13, 9, 4 Hz, 1H), 3.50 (d, J=15.3 Hz, 1H), 2.23 (d, J=0.8 Hz, 3H), 1.87 (s, 3H), 1.23 (d, J=6.8 Hz, 1H), 0.63 (d, J=6.6 Hz, 1H).

Examples 12 and 13

2-{[(1aS,6bS)-5-(Difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (12) and 2-{[(1aR,6bR)-5-(Difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (13)

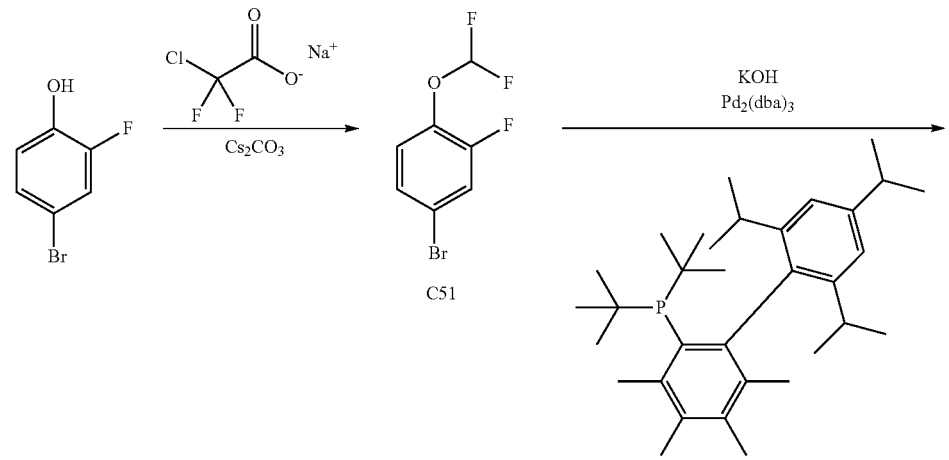

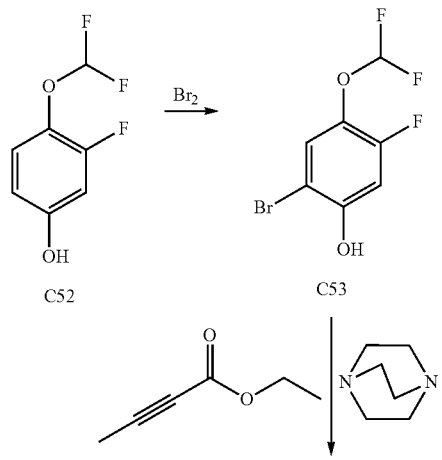

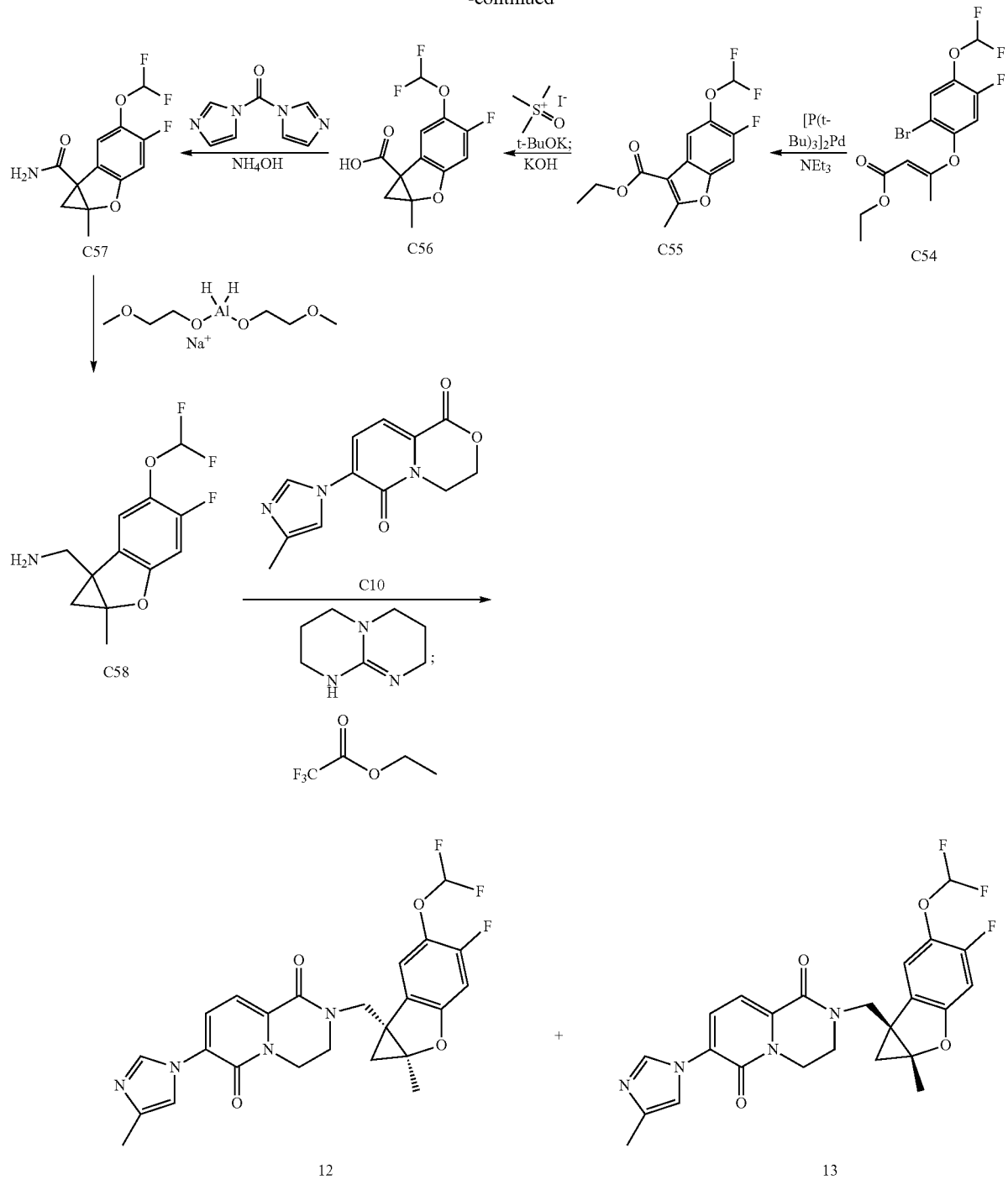

Step 1. Synthesis of 4-bromo-1-(difluoromethoxy)-2-fluorobenzene (C51)

4-Bromo-2-fluorophenol (2.78 mL, 25.4 mmol) was added to a mixture of cesium carbonate (97%, 12.8 g, 38.1 mmol), N,N-dimethylformamide (100 mL), and water (10 mL) at 70° C. Sodium chloro(difluoro)acetate (9.69 g, 63.6 mmol) was then introduced portion-wise, over 30 minutes. The reaction mixture was allowed to stir at 70° C. overnight, whereupon it was cooled to room temperature and poured into water. The resulting mixture was extracted three times with ethyl acetate; the combined organic layers were washed sequentially with 1 M aqueous sodium hydroxide solution, water, and saturated aqueous sodium chloride solution, dried over magnesium sulfate, filtered, and concentrated in vacuo. Silica gel chromatography (Gradient: 0% to 20% ethyl acetate in heptane) afforded the product as a colorless oil. Yield: 1.50 g, 6.22 mmol, 24%. $^1$H NMR (400 MHz, CDCl$_3$) δ 7.36 (dd, J=9.7, 2.3 Hz, 1H), 7.28 (ddd, J=8.7, 2.2, 1.6 Hz, 1H), 7.14 (br dd, J=8.6, 8.4 Hz, 1H), 6.54 (t, J$_{HF}$=73.0 Hz, 1H).

Step 2. Synthesis of 4-(difluoromethoxy)-3-fluorophenol (C52)

A mixture of water (3 mL) and 1,4-dioxane (3 mL) was purged with nitrogen for 15 minutes, whereupon potassium hydroxide (85%, 1.64 g, 24.8 mmol), tris(dibenzylideneacetone)dipalladium(0) (57 mg, 62 mmol), and di-tert-butyl [3,4,5,6-tetramethyl-2',4',6'-tri(propan-2-yl)biphenyl-2-yl]phosphane (97%, 123 mg, 0.248 mmol) were added. After addition of C51 (1.50 g, 6.22 mmol), the reaction mixture was heated at 100° C. for 1 hour, then cooled to room temperature and treated with aqueous sodium hydroxide solution (1 M, 100 mL). The resulting mixture was washed with diethyl ether (50 mL), adjusted to acidic pH via addition of concentrated hydrochloric acid, and extracted with diethyl ether (2×150 mL). These extracts were combined, treated with decolorizing carbon, dried over magnesium sulfate, filtered, and concentrated in vacuo, affording the product (1.36 g) as an oil. This material contained significant solvent by $^1$H NMR analysis, and was taken to the following step without additional manipulation. $^1$H NMR (400 MHz, CDCl$_3$), product peaks only: δ 7.08 (br dd, J=8.9, 8.9 Hz, 1H), 6.65 (dd, J=11.6, 2.9 Hz, 1H), 6.56 (ddd, J=8.9, 2.9, 1.5 Hz, 1H), 6.45 (t, $J_{HF}$=73.9 Hz, 1H).

Step 3. Synthesis of 2-bromo-4-(difluoromethoxy)-5-fluorophenol (C53)

A solution of C52 (from the previous step; 1.36 g, ≤6.22 mmol; estimated to contain ~4.6 mmol of C52 from analysis of the $^1$H NMR spectrum) in dichloromethane (23 mL) was cooled in an ice bath and treated with bromine (0.24 mL, 4.6 mmol) in a drop-wise manner. The reaction mixture was allowed to warm slowly to room temperature overnight, whereupon it was washed with aqueous sodium thiosulfate solution, dried over magnesium sulfate, filtered, and concentrated in vacuo. The product was obtained as an oil (1.4 g), which contained solvent as judged by $^1$H NMR analysis; this material was used directly in the following step. GCMS m/z 256.0 [M$^+$]. $^1$H NMR (400 MHz, CDCl$_3$), product peaks only: δ 7.40 (br d, J=7.9 Hz, 1H), 6.88 (d, J=11.0 Hz, 1H), 6.47 (t, $J_{HF}$=73.2 Hz, 1H), 5.67-5.78 (br s, 1H).

Step 4. Synthesis of ethyl (2E)-3-[2-bromo-4-(difluoromethoxy)-5-fluorophenoxy]but-2-enoate (C54)

1,4-Diazabicyclo[2.2.2]octane (589 mg, 5.25 mmol) was added to a solution of C53 (from the previous step; 1.4 g, estimated to contain ~4.3 mmol of C53 from analysis of the $^1$H NMR spectrum) and ethyl but-2-ynoate (0.90 mL, 7.7 mmol) in toluene (13 mL). The reaction mixture was heated at 90° C. for 6 hours, whereupon it was cooled to room temperature and partitioned between 1 M aqueous hydrochloric acid and diethyl ether. The organic layer was washed sequentially with 1 M aqueous hydrochloric acid, 1 M aqueous sodium hydroxide solution, and with water. It was then dried over magnesium sulfate, filtered, and concentrated in vacuo. Chromatography on silica gel (Gradient: 0% to 5% ethyl acetate in heptane) afforded the product as a thick oil. Yield: 1.23 g, 3.33 mmol, 54% over 3 steps. GCMS m/z 323, 325 [M−(OEt)]$^+$. $^1$H NMR (400 MHz, CDCl$_3$) δ 7.55 (br d, J=7.9 Hz, 1H), 6.99 (d, J=10.0 Hz, 1H), 6.56 (t, $J_{HF}$=72.5 Hz, 1H), 4.78 (s, 1H), 4.13 (q, J=7.1 Hz, 2H), 2.52 (s, 3H), 1.25 (t, J=7.1 Hz, 3H).

Step 5. Synthesis of ethyl 5-(difluoromethoxy)-6-fluoro-2-methyl-1-benzofuran-3-carboxylate (C55)

A solution of C54 (1.23 g, 3.33 mmol) and triethylamine (2.0 mL, 14 mmol) in acetonitrile (10 mL) was purged with nitrogen for 15 minutes. Bis(tri-tert-butylphosphine)palladium(0) (170 mg, 0.33 mmol) was introduced, and the reaction mixture was heated at 90° C. for 2 hours, whereupon it was cooled to room temperature and partitioned between heptane and 1 M aqueous hydrochloric acid. The organic layer was washed with 1 M aqueous hydrochloric acid and with water, then dried over magnesium sulfate, filtered, and concentrated in vacuo. The resulting solid was dissolved in methanol (30 mL), treated with decolorizing carbon, stirred for 10 minutes, and filtered through diatomaceous earth. Removal of solvent under reduced pressure provided the product as an off-white solid. Yield: 510 mg, 1.77 mmol, 53%. GCMS m/z 288.1 [M$^+$]. $^1$H NMR (400 MHz, CDCl$_3$) δ 7.83 (d, J=7.8 Hz, 1H), 7.27 (d, J=9.6 Hz, 1H), 6.57 (t, $J_{HF}$=73.8 Hz, 1H), 4.42 (q, J=7.2 Hz, 2H), 2.77 (s, 3H), 1.45 (t, J=7.1 Hz, 3H).

Step 6. Synthesis of 5-(difluoromethoxy)-4-fluoro-1a-methyl-1,1a-dihydro-6bH-cyclopropa[b][1]benzofuran-6b-carboxylic acid (C56)

Potassium tert-butoxide (1.0 M solution, 2.1 mL, 2.1 mmol) was added to a suspension of trimethylsulfoxonium iodide (98%, 0.477 g, 2.12 mmol) in dimethyl sulfoxide (4.5 mL), and the mixture was allowed to stir at room temperature for 30 minutes. A solution of C55 (510 mg, 1.77 mmol) in tetrahydrofuran (2.5 mL) was then introduced in a drop-wise manner over 15 minutes, and the reaction mixture was stirred at room temperature for 1 hour. Crushed potassium hydroxide pellets (85%, 0.292 g, 4.42 mmol) were added, and stirring was continued for 1 hour, whereupon the reaction mixture was cooled in an ice bath, diluted with water (25 mL), and washed with heptane (50 mL). The aqueous layer was cooled in an ice bath and adjusted to a pH of 4-5 via addition of concentrated hydrochloric acid. The mixture was extracted with diethyl ether, and the combined organic layers were washed with water and with saturated aqueous sodium chloride solution, dried over sodium sulfate, filtered, and concentrated in vacuo. The product was obtained as a thick oil, which solidified to a yellow-orange solid upon standing. Yield: 214 mg, 0.780 mmol, 44%. LCMS m/z 273.4 [M−H$^+$]. $^1$H NMR (400 MHz, CDCl$_3$) δ 7.52 (d, J=7.9 Hz, 1H), 6.68 (d, J=10 Hz, 1H), 6.48 (t, $J_{HF}$=73.9 Hz, 1H), 2.04 (d, J=6.2 Hz, 1H), 1.88 (s, 3H), 0.99 (d, J=6.2 Hz, 1H).

Step 7. Synthesis of 5-(difluoromethoxy)-4-fluoro-1a-methyl-1,1a-dihydro-6bH-cyclopropa[b][1]benzofuran-6b-carboxamide (C57)

Compound C56 (214 mg, 0.780 mmol) was converted to the product using the method described for synthesis of C38 from C37 in Examples 6 and 7. The product was obtained as a thick oil (200 mg) that contained significant solvent via $^1$H NMR analysis; this material was taken directly to the following step. GCMS m/z 273.1 [M$^+$]. $^1$H NMR (400 MHz, CDCl$_3$), product peaks only: δ 7.33 (d, J=7.6 Hz, 1H), 6.73 (d, J=10.2 Hz, 1H), 6.49 (t, $J_{HF}$=73.5 Hz, 1H), 5.77-5.99 (br m, 2H), 2.11 (d, J=6.3 Hz, 1H), 1.74 (s, 3H), 0.77 (d, J=6.3 Hz, 1H).

Step 8. Synthesis of 1-[5-(difluoromethoxy)-4-fluoro-1a-methyl-1,1a-dihydro-6bH-cyclopropa[b][1]benzofuran-6b-yl]methanamine (C58)

A solution of C57 (from the previous step; 200 mg, <0.73 mmol) in toluene (2 mL) was cooled in an ice bath and slowly treated with sodium bis(2-methoxyethoxy)aluminum hydride (3.3 M solution in toluene, 0.56 mL, 1.8 mmol), while the internal reaction temperature was kept below 15° C. Upon completion of the addition, the ice bath was removed and the reaction mixture was allowed to warm to room temperature and stir overnight. Sodium bis(2-methoxyethoxy)aluminum hydride (3.3 M solution in toluene, 2.2 mL, 7.3 mmol) was again added, and stirring was continued at room temperature for 24 hours, whereupon additional sodium bis(2-methoxyethoxy)aluminum hydride (3.3 M solution in toluene, 2.7 mL, 8.9 mmol) was introduced. After the reaction mixture had stirred at room temperature for 24 hours, it was heated at 50° C. for 24 hours. It was then allowed to cool to room temperature, further cooled in an ice bath, and quenched via slow addition of aqueous sodium hydroxide solution (1 M, 50 mL), while the internal temperature was maintained below 30° C. This mixture was stirred for 15 minutes, whereupon it was extracted with diethyl ether (3×20 mL); the combined organic layers were dried over sodium sulfate, filtered, and concentrated in vacuo to afford the product as a thick oil (105 mg), which was substantially impure via $^1$H NMR analysis. This material was used directly in the following step. GCMS m/z 242.1 [M–NH$_3$]$^+$.

Step 9. Synthesis of 2-{[(1aS,6b5)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione (12) and 2-{[(1aR,6bR)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1, 6-dione (13)

1,3,4,6,7,8-Hexahydro-2H-pyrimido[1,2-a]pyrimidine (97%, 94.7 mg, 0.660 mmol) was added to a mixture of C58 (from the previous step; 105 mg, <0.40 mmol) and C10 (129 mg, 0.526 mmol) in N,N-dimethylformamide (1 mL), and the reaction mixture was stirred at room temperature for 2 hours. Ethyl trifluoroacetate (0.12 mL, 1.01 mmol) was added, and after an additional hour of stirring, the reaction mixture was treated with aqueous sodium hydroxide solution (1 M, 1.5 mL) and allowed to stir for 30 minutes, whereupon it was extracted three times with ethyl acetate. The combined organic layers were washed twice with saturated aqueous sodium chloride solution, dried over magnesium sulfate, filtered, and concentrated in vacuo. The residue was subjected to chromatography on silica gel (Gradient: 0% to 3% methanol in dichloromethane), followed by purification using supercritical fluid chromatography [Column: Chiral Technologies Chiralpak AD-H, 5 μm; Mobile phase: 30% (methanol containing 0.6% ammonium hydroxide) in carbon dioxide].

Compound 12 was the second-eluting enantiomer. Yield: 4.4 mg, 9.0 μmol, 1.2% over three steps. LCMS m/z 487.3 [M+H]$^+$. Retention time: 3.86 minutes {Analysis via supercritical fluid chromatography [Column: Chiral Technologies Chiralpak AD-H, 4.6×100 mm, 5 μm; Mobile phase: 40% (methanol containing 0.6% ammonium hydroxide) in carbon dioxide; Flow rate: 1.5 mL/minute]}.

The first-eluting enantiomer was 13. Yield: 4.4 mg, 9.0 μmol, 1.2% over three steps. LCMS m/z 487.3 [M+H]$^+$. Retention time: 2.81 minutes using an analytical system identical to that employed for 12.

Example 14

2-{[(1aS,6bS)-4-Fluoro-1a-methyl-5-(trifluoromethoxy)-1,1a-dihydro-6bH-cyclopropa[b][1]benzofuran-6b-yl]methyl}-7-[4-(hydroxymethyl)-1H-imidazol-1-yl]-3,4-dihydro-2H-pyrido[1,2-a]pyrazine-1,6-dione (14)

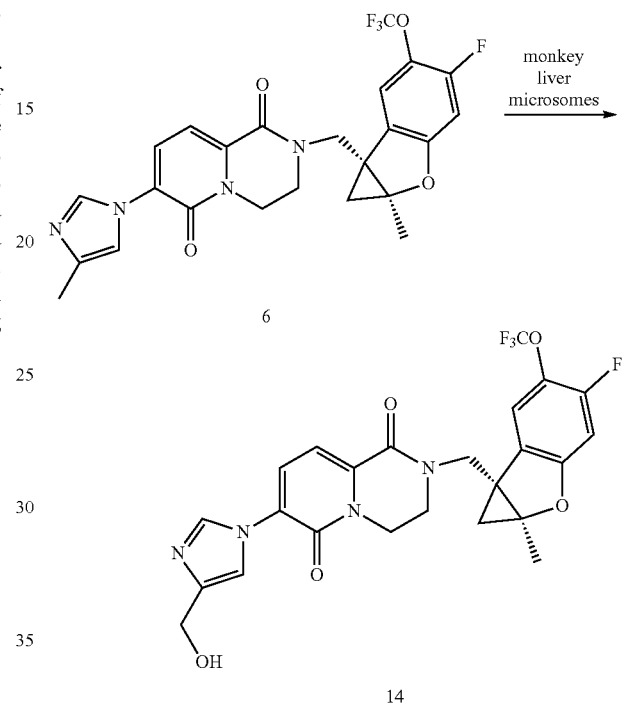

Compound 6 (0.4 mg, 800 nmol) was incubated with liver microsomes (from male monkeys; 1.5 mg/mL), magnesium chloride (3.3 mM), and NADPH (1.3 mM), in 0.1 M potassium phosphate buffer (pH 7.4; total volume of incubation solution, 40 mL). The reaction mixture was shaken at 37° C. in a water bath for 67 minutes, whereupon acetonitrile (40 mL) was added and the mixture was spun at 1700 g for 5 minutes. The supernatant was subjected to vacuum centrifugation to a volume of approximately 15 mL, to which was added formic acid (0.5 mL), acetonitrile (0.5 mL), and water (sufficient to reach a total volume of 50 mL). This mixture was spun at 40000 g for 30 minutes. The supernatant was purified via reversed phase chromatography (Column: Agilent Polaris C18, 5 μm; Mobile phase A: 0.1% aqueous formic acid; Mobile phase B: acetonitrile; Gradient: 1% to 90% B) to afford the product. Yield: 17 μg, 32 nmol, 4%. LCMS m/z 521.1 [M+H]$^+$. $^1$H NMR (600 MHz, DMSO-d$_6$), characteristic peaks: δ 8.25 (s, 1H), 7.84 (d, J=7.8 Hz, 1H), 7.52 (s, 1H), 7.49 (d, J=7.8 Hz, 1H), 7.07-7.12 (m, 2H), 4.58 (d, J=15.0 Hz, 1H), 4.39 (s, 2H), 4.16-4.22 (m, 1H), 4.13 (ddd, half of ABXY pattern, J=14, 8, 4 Hz, 1H), 3.68-3.74 (m, 1H), 3.54 (d, J=15.1 Hz, 1H), 3.50 (ddd, J=13, 8, 4 Hz, 1H), 1.80 (s, 3H), 0.59 (d, J=6.4 Hz, 1H).

TABLE 6

Method of Synthesis and Physicochemical Data for Examples 15-22.

| Example Number | Method of Preparation; Non-commercial starting materials | Structure | $^1$H NMR (400 MHz, CDCl$_3$,) δ; LCMS, observed ion m/z [M + H]$^+$ |
|---|---|---|---|
| 15 | Examples 4 and 5[1] | 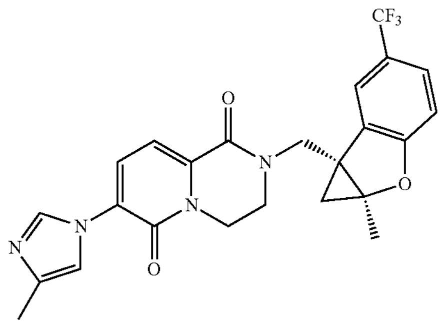 [SMILES: Cc1cn(-c2ccc3n(c2=O)CCN(C[C@@]24C[C@]2(C)Oc2ccc(C(F)(F)F)cc24)C3=O)cn1] | 8.19-8.25 (m, 1H), 7.56-7.59 (m, 1H), 7.45 (d, J = 7.6 Hz, 1H), 7.40 (br d, J = 8.4 Hz, 1H), 7.30 (d, J = 7.8 Hz, 1H), 7.09-7.15 (m, 1H), 6.90 (d, J = 8.3 Hz, 1H), 5.04 (d, J = 15.2 Hz, 1H), 4.25-4.33 (m, 1H), 4.20 (ddd, half of ABXY pattern, J = 14, 8, 4 Hz, 1H), 3.58 (ddd, half of ABXY pattern, J = 13, 6, 4 Hz, 1H), 3.46 (ddd, half of ABXY pattern, J = 13, 8, 4 Hz, 1H), 3.27 (d, J = 15.1 Hz, 1H), 2.28 (br s, 3H), 1.86 (s, 3H), 1.04 (d, J = 6.5 Hz, 1H), 0.67 (d, J = 6.5 Hz, 1H); 471.0 |
| 16 | Examples 4 and 5[1] | 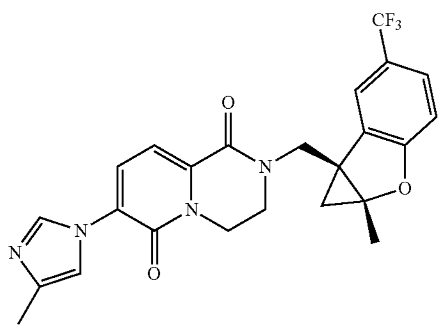 [SMILES: Cc1cn(-c2ccc3n(c2=O)CCN(C[C@]24C[C@@]2(C)Oc2ccc(C(F)(F)F)cc24)C3=O)cn1] | 8.19-8.23 (m, 1H), 7.56-7.59 (m, 1H), 7.45 (d, J = 7.8 Hz, 1H), 7.40 (br d, J = 8.3 Hz, 1H), 7.30 (d, J = 7.6 Hz, 1H), 7.10-7.14 (m, 1H), 6.90 (d, J = 8.3 Hz, 1H), 5.04 (d, J = 15.3 Hz, 1H), 4.25-4.33 (m, 1H), 4.20 (ddd, half of ABXY pattern, J = 14, 8.5, 4 Hz, 1H), 3.54-3.62 (m, 1H), 3.46 (ddd, half of ABXY pattern, J = 13, 8.5, 4 Hz, 1H), 3.27 (d, J = 15.2 Hz, 1H), 2.28 (s, 3H), 1.86 (s, 3H), 1.04 (d, 7= 6.6 Hz, 1H), 0.67 (d, J = 6.5 Hz, 1H); 471.0 |
| 17 | Examples 2 and 3[2,3] | 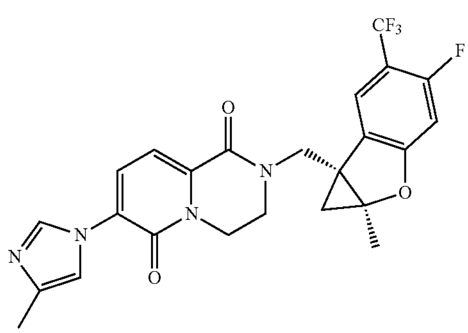 [SMILES: Cc1cn(-c2ccc3n(c2=O)CCN(C[C@@]24C[C@]2(C)Oc2cc(F)c(C(F)(F)F)cc24)C3=O)cn1] | $^1$H NMR (400 MHz, CD$_3$OD), δ 8.42-8.49 (br s, 1H), 7.81 (d, J = 7.7 Hz, 1H), 7.67 (br d, J = 7.4 Hz, 1H), 7.34-7.39 (br s, 1H), 7.28 (d, J = 7.8 Hz, 1H), 6.79 (br d, J = 11 Hz, 1H), 4.81-4.90 (m, 1H, assumed; partially obscured by water peak), 4.29-4.37 (m, 1H), 4.20 (ddd, half of ABXY pattern, J = 14, 9, 4 Hz, 1H), 3.69-3.78 (m, 1H), 3.50-3.59 (m, 1H), 3.50 (d, J = 15.2 Hz, 1H), 2.26 (s, 3H), 1.87 (s, 3H), 1.20 (d, J = 6.6 Hz, 1H), 0.62 (d, J = 6.6 Hz, 1H); 489.4 |

TABLE 6-continued

Method of Synthesis and Physicochemical Data for Examples 15-22.

| Example Number | Method of Preparation; Non-commercial starting materials | Structure | $^1$H NMR (400 MHz, CDCl$_3$,) δ; LCMS, observed ion m/z [M + H]$^+$ |
|---|---|---|---|
| 18 | Examples 2 and 3[2,3] | 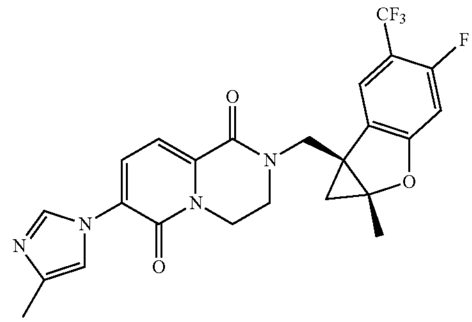 [SMILES: Cc1cn(-c2ccc3n(c2=O)CCN(C[C@]24C[C@@]2(C)Oc2cc(F)c(C(F)(F)F)cc24)C3=O)cn1] | $^1$H NMR (400 MHz, CD$_3$OD), δ 8.28 (br s, 1H), 7.77 (d, J = 7.8 Hz, 1H), 7.67 (br d, J = 7.3 Hz, 1H), 7.28-7.31 (br s, 1H), 7.27 (d, J = 7.7 Hz, 1H), 6.79 (br d, J = 11.2 Hz, 1H), 4.82-4.87 (m, 1H, assumed; partially obscured by water peak), 4.33 (ddd, half of ABXY pattern, J = 14.2, 6.2, 4.3 Hz, 1H), 4.20 (ddd, half of ABXY pattern, J = 14.2, 8.7, 4.2 Hz, 1H), 3.73 (ddd, J = 13.2, 6.2, 4.3 Hz, 1H), 3.54 (ddd, J = 13.3, 8.7, 4.2 Hz, 1H), 3.50 (d, J = 15.2 Hz, 1H), 2.23 (d, J = 0.8 Hz, 3H), 1.87 (s, 3H), 1.20 (d, J = 6.6 Hz, 1H), 0.62 (d, J = 6.7 Hz, 1H); 489.4 |
| 19 | Examples 4 and 5[4] | 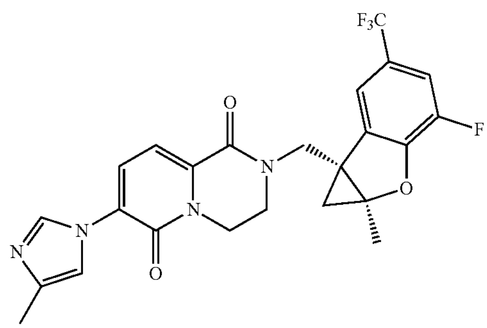 [SMILES: Cc1cn(-c2ccc3n(c2=O)CCN(C[C@@]24C[C@]2(C)Oc2c(F)cc(C(F)(F)F)cc24)C3=O)cn1] | 8.20 (br s, 1H), 7.44 (d, J = 7.8 Hz, 1H), 7.40-7.42 (m, 1H), 7.28 (d, J = 7.6 Hz, 1H), 7.20 (br d, J = 10.3 Hz, 1H), 7.11 (br s, 1H), 5.03 (d, J = 15.2 Hz, 1H), 4.34 (ddd, half of ABXY pattern, J = 14.3, 6.3, 4.3 Hz, 1H), 4.18 (ddd, half of ABXY pattern, J = 14.3, 8.7, 4.3 Hz, 1H), 3.58 (ddd, half of ABXY pattern, J = 13.0, 6.2, 4.3 Hz, 1H), 3.48 (ddd, half of ABXY pattern, J = 13.1, 8.6, 4.1 Hz, 1H), 3.24 (d, J = 15.2 Hz, 1H), 2.27 (br s, 3H), 1.90 (s, 3H), 1.11 (d, J = 6.9 Hz, 1H), 0.75 (d, J = 6.8 Hz, 1H); 489.2 |
| 20 | Examples 4 and 5[4] | 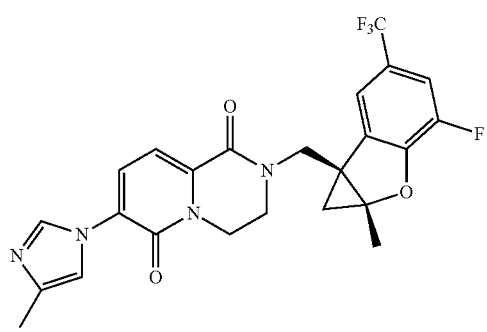 [SMILES: Cc1cn(-c2ccc3n(c2=O)CCN(C[C@]24C[C@@]2(C)Oc2c(F)cc(C(F)(F)F)cc24)C3=O)cn1] | 8.21 (br s, 1H), 7.44 (d, J = 7.8 Hz, 1H), 7.40-7.43 (m, 1H), 7.28 (d, J = 8.0 Hz, 1H), 7.21 (br d, J = 10.4 Hz, 1H), 7.11 (br s, 1H), 5.04 (d, J = 15.2 Hz, 1H), 4.35 (ddd, half of ABXY pattern, J = 14, 6, 4 Hz, 1H), 4.19 (ddd, half of ABXY pattern, J = 14, 8.5, 4 Hz, 1H), 3.58 (ddd, half of ABXY pattern, J = 13, 6, 4 Hz, 1H), 3.48 (ddd, half of ABXY pattern, J = 13, 8.5, 4 Hz, 1H), 3.25 (d, J = 15.3Hz, 1H), 2.28 (s, 3H), 1.90 (s, 3H), 1.11 (d J = 6.9 Hz, 1H), 0.75 (d, J = 6.9 Hz, 1H); 489.2 |

TABLE 6-continued

Method of Synthesis and Physicochemical Data for Examples 15-22.

| Example Number | Method of Preparation; Non-commercial starting materials | Structure | $^1$H NMR (400 MHz, CDCl$_3$,) δ; LCMS, observed ion m/z [M + H]$^+$ |
|---|---|---|---|
| 21 | Examples 4 and 5[5,6] | 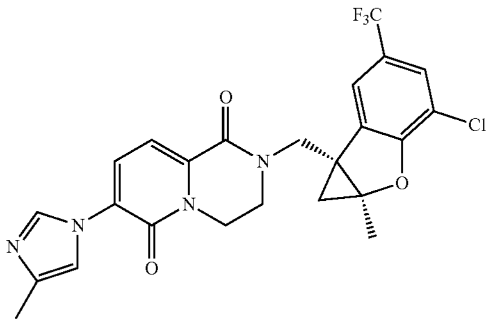 [SMILES: Cc1cn(-c2ccc3n(c2=O)CCN(C[C@@]24C[C@]2(C)Oc2c(Cl)cc(C(F)(F)F)cc24)C3=O)cn1] | 8.20-8.23 (m, 1H), 7.50-7.53 (m, 1H), 7.44 (d, J = 7.6 Hz, 1H), 7.42-7.45 (m, 1H), 7.28 (d, J = 7.6 Hz, 1H), 7.10-7.13 (m, 1H), 5.07 (d, J = 15.2 Hz, 1H), 4.37 (ddd, half of ABXY pattern, J = 14, 6, 4 Hz, 1H), 4.18 (ddd, half of ABXY pattern, J = 14, 9, 4 Hz, 1H), 3.53-3.61 (m, 1H), 3.48 (ddd, half of ABXY pattern, J = 13, 9, 4 Hz, 1H), 3.22 (d, J = 15.3 Hz, 1H), 2.28 (br s, 3H), 1.92 (s, 3H), 1.11 (d, J = 6.8 Hz, 1H), 0.75 (br d, J = 6.7 Hz, 1H); 505.0 |
| 22 | Examples 4 and 5[5,6] | 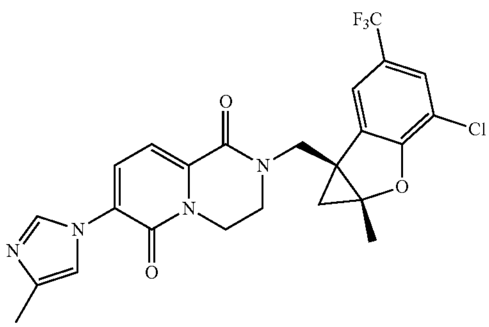 [SMILES: Cc1cn(-c2ccc3n(c2=O)CCN(C[C@]24C[C@@]2(C)Oc2c(Cl)cc(C(F)(F)F)cc24)C3=O)cn1] | 8.21 (d, J = 1.1 Hz, 1H), 7.50-7.53 (m, 1H), 7.44 (d, J = 7.8 Hz, 1H), 7.42-7.44 (m, 1H), 7.28 (d, J = 7.9 Hz, 1H), 7.10-7.13 (m, 1H), 5.07 (d, J = 15.2 Hz, 1H), 4.37 (ddd, half of ABXY pattern, J = 14.3, 6.0, 4.2 Hz, 1H), 4.18 (ddd, half of ABXY pattern, J = 14.4, 8.8, 4.2 Hz, 1H), 3.57 (ddd, half of ABXY pattern, J = 13.0, 6.2, 4.2 Hz, 1H), 3.48 (ddd, half of ABXY pattern, J = 13.0, 8.7, 4.1 Hz, 1H), 3.22 (d, J = 15.2 Hz, 1H), 2.28 (d, J = 0.8 Hz, 3H), 1.92 (s, 3H), 1.11 (d, J = 6.8 Hz, 1H), 0.75 (d, J = 6.9 Hz, 1H); 505.0 |

1. Examples 15 and 16 were isolated from the racemic mixture via supercritical fluid chromatography (Column: Chiral Technologies Chiralpak AD-3, 3 μm; Mobile phase A: carbon dioxide; Mobile phase B: methanol containing 0.05% diethylamine; Gradient: 5% to 40% B). Analytical supercritical fluid chromatography (Column: Chiralpak AD-3, 150×4.6 mm, 3 μm; Mobile phase A: carbon dioxide; Mobile phase B: methanol containing 0.05% diethylamine; Gradient: 5% to 40% B over 5.5 min, then 40% B for 2 minutes; Flow rate: 2.5 mL/minute) yielded a retention time of 5.69 minutes for Example 15, and a retention time of 5.42 minutes for Example 16.

2. The requisite 5-fluoro-2-iodo-4-(trifluoromethyl)phenol was synthesized via treatment of a solution of 3-fluoro-4-(trifluoromethyl)phenol in acetic acid with N-iodosuccinimide and sulfuric acid.

3. Examples 17 and 18 were isolated from the racemic mixture via supercritical fluid chromatography [Column: Princeton PPU, 5 μm; Mobile phase: 30% (0.2% ammonium hydroxide in ethanol) in carbon dioxide]. Example 17 was the second-eluting enantiomer in this system, with Example 18 eluting first.

4. Examples 19 and 20 were isolated from the racemic mixture via supercritical fluid chromatography [Column: Chiral Technologies Chiralpak AD, 10 μm; Mobile phase: 35% (methanol containing 0.1% ammonium hydroxide) in carbon dioxide]. Example 19 was the second-eluting enantiomer in this system, with Example 20 eluting first.

5. In this case, cleavage of the benzyl ether was not carried out via hydrogenation; instead, treatment with 2,3-dichloro-5,6-dicyano-1,4-benzoquinone in dichloromethane afforded the corresponding aldehyde, which was reduced using sodium borohydride.

6. Examples 21 and 22 were isolated from the racemic mixture via supercritical fluid chromatography [Column: Chiral Technologies Chiralpak AD, 5 μm, Mobile phase: 40% (methanol containing 0.05% diethylamine) in carbon dioxide]. Example 21 was the second-eluting enantiomer in this system, with Example 22 eluting first.

Cell-Based γ-Secretase Assay with ELISA Readout

The ability of compounds to modulate production of amyloid beta protein Aβ(1-42) was determined using human WT-APP overexpressing CHO cells. Cells were plated at 22,000 cells/100 μL well in 96 well tissue culture treated, clear plates (Falcon) in DMEM/F12 based medium and incubated for 24 h at 37° C. Compounds for testing were diluted in 100% DMSO to achieve an eleven point, half log, dose response for $IC_{50}$ determinations. Compounds were added in fresh medium to achieve 1% final DMSO. Appropriate vehicle or inhibitor controls were added into control wells individually to obtain minimum or maximum inhibition values, respectively, for the assay signal window before the plates were incubated for ~24 h at 37° C. This procedure produces conditioned media in each well, which is tested for Aβ(1-42) levels in the ELISA detection step described next. The remaining cell cultures in each well are also tested for cell toxicity as described below.

Coating of ELISA assay plates was initiated by addition of 50 μL/well of an in-house Aβ(1-42) specific antibody (3 μg/mL) in 0.1 M $NaHCO_3$ (pH 9.0) into black 384-well Maxisorp® plates (Nunc); incubation was carried out overnight at 4° C. The capture antibody was then aspirated from the ELISA assay plates and plates were washed either 2×100 μL with a Matrical Squirt plate washer, or 3×90 μL with a Thermo Combi, using Wash Buffer (Dulbecco's PBS, 0.05% Tween 20). 90 μL/well of Blocking Buffer (Dulbecco's PBS, 1.0% BSA (Sigma A7030) was then added to plates. Ambient temperature incubation was allowed to proceed for a minimum of 2 h. Blocking Buffer was then removed and 20 μL/well Assay Buffer (Dulbecco's PBS, 1.0% BSA (Sigma A7030), 0.05% Tween 20) was then added. At this point, 35 μL (40 μL prior to August, 2012) (in duplicate) of experimental conditioned media (described above) was transferred into wells of the blocked ELISA plates containing the capture antibody, followed by overnight incubation at 4° C. Cell toxicity was also measured in the corresponding remaining cells after removal of the conditioned media for the Aβ(1-42) assay by a colorimetric cell proliferation assay (CellTiter 96® $AQ_{ueous}$ One Solution Cell Proliferation Assay, Promega) according to the manufacturer's instructions.

After overnight incubation of the ELISA assay plates at 4° C., unbound Aβ peptides were removed via either 2×100 μL washes with a Matrical Squirt plate washer, or 3×90 μL washes with a Thermo Combi, using Wash Buffer. Europium (Eu) labeled (custom labeled, PerkinElmer) Aβ(1-16) 6e10 Monoclonal Antibody (Covance #SIG-39320) was added, (50 μL/well Eu-6e10@1:10,000, 20 uM EDTA) in Assay Buffer. Incubation at ambient temperature for a minimum of 2 h was followed by either 2×100 μL washes with a Matrical Squirt plate washer, or 3×90 μL washes with a Thermo Combi, using Wash Buffer, before 30 μL/well of Delfia Enhancement Solution (PerkinElmer) was added. Following 30 to 60 min ambient temperature incubation, the plates were read on an EnVision plate reader (PerkinElmer) using standard DELFIA TRF settings. Data analysis including inhibitory $IC_{50}$ determination was performed using nonlinear regression fit analysis (in-house software) and the appropriate plate mean values for the maximum and minimum inhibition controls.

Biological data for the compounds of Examples 1-22 and C22, C33, C40 and C44 are found in Table 7 below:

TABLE 7

| Example Number | Aβ 42B $IC_{50}$ (nM) Geometric mean of 2-4 determinations (unless otherwise indicated) | IUPAC Name |
|---|---|---|
| 1 | 48.5 | 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione |
| C22 | 19.5 | 7-(4-methyl-1H-imidazol-1-yl)-2-{[1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione |
| 2 | 6.5 | 7-(4-methyl-1H-imidazol-1-yl)-2-{[(1aS,6bS)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione |
| 3 | 59.2 | 7-(4-methyl-1H-imidazol-1-yl)-2-{[(1aR,6bR)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione |
| C33 | 9.3[a] | 2-{[3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 4 | 4.9 | 2-{[(1aS,6bS)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 5 | 59.2 | 2-{[(1aR,6bR)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| C40 | 11.2 | 2-{[4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 6 | 7.0 | 2-{[(1aS,6bS)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |

TABLE 7-continued

| Example Number | Aβ 42B IC$_{50}$ (nM) Geometric mean of 2-4 determinations (unless otherwise indicated) | IUPAC Name |
|---|---|---|
| 7 | 38.0 | 2-{[(1aR,6bR)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| C44 | 68.9 | 2-{[4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione |
| 8 | 36.6 | 2-{[(1aS,6bS)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione |
| 9 | 519 | 2-{[(1aR,6bR)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione |
| 10 | 3.0[b] | 2-{[(1aS,6bS)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 11 | 10.0 | 2-{[(1aR,6bR)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 12 | 17.8 | 2-{[(1aS,6bS)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 13 | 84.9 | 2-{[(1aR,6bR)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 14 | 18.7 | 2-{[(1aS,6bS)-4-fluoro-1a-methyl-5-(trifluoromethoxy)-1,1a-dihydro-6bH-cyclopropa[b][1]benzofuran-6b-yl]methyl}-7-[4-(hydroxymethyl)-1H-imidazol-1-yl]-3,4-dihydro-2H-pyrido[1,2-a]pyrazine-1,6-dione |
| 15 | 8.5[b] | 7-(4-methyl-1H-imidazol-1-yl)-2-{[(1aS,6bS)-1a-methyl-5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione |
| 16 | 47.3 | 7-(4-methyl-1H-imidazol-1-yl)-2-{[(1aR,6bR)-1a-methyl-5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione |
| 17 | 4.4[b] | 2-{[(1aS,6bS)-4-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 18 | 20.2 | 2-{[(1aR,6bR)-4-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 19 | 11.1 | 2-{[(1aS,6bS)-3-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 20 | 50.1 | 2-{[(1aR,6bR)-3-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |
| 21 | 16.0 | 2-{[(1aS,6bS)-3-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |

TABLE 7-continued

| Example Number | Aβ 42B IC$_{50}$ (nM) Geometric mean of 2-4 determinations (unless otherwise indicated) | IUPAC Name |
|---|---|---|
| 22 | 58.3 | 2-{[(1aR,6bR)-3-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione |

[a]Reported IC$_{50}$ value is from a single determination.
[b]Reported IC$_{50}$ value is the geometric mean of ≥5 determinations.

The invention claimed is:
1. A compound having the structure of Formula I:

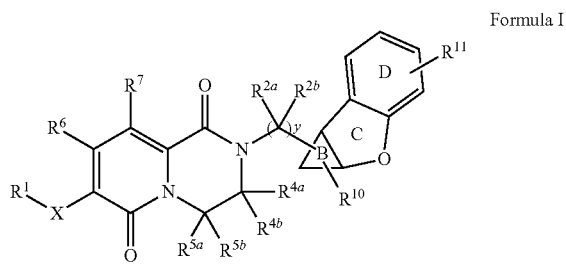

Formula I or pharmaceutically acceptable salts thereof, wherein:
X is a (5- to 14-membered)heteroaryl containing 1-3 heteroatoms;
$R^1$ is selected from the group consisting of hydrogen, halogen, cyano, hydroxy, oxo, —SF$_5$, nitro, optionally substituted (C$_1$-C$_6$)alkyl, optionally substituted (C$_2$-C$_6$) alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_3$-C$_8$)cycloalkyl, —N(R$^4$)(R$^5$), —N(R$^4$)(C=(O)R$^5$), —C(=O)N(R$^4$)(R$^5$), —O—C(=O)N(R$^4$)(R$^5$), —C(=O)—R$^4$, and —C(=O)—OR$^4$;
$R^{2a}$ and $R^{2b}$ at each occurrence, are independently selected from the group consisting of hydrogen, halogen, cyano, hydroxy, oxo, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_1$-C$_6$)alkoxy (C$_1$-C$_6$)alkyl, optionally substituted (C$_3$-C$_8$)cycloalkyl, optionally substituted phenyl, —N(R$^4$)(R$^5$), —N(R$^4$) (C=(O)R$^5$), —C(=O)N(R$^4$)(R$^5$), —O—C(=O)N (R$^4$)(R$^5$), —C(=O)—R$^4$, and —C(=O)—OR$^4$; or R$^{2a}$ and R$^{2b}$ together with the carbon atom(s) to which they are attached form a (C$_3$-C$_8$)cycloalkyl or a (4- to 10-membered)heterocycloalkyl, wherein the (C$_3$-C$_8$) cycloalkyl and the (4- to 10-membered)heterocycloalkyl are optionally substituted with one to three R$^8$;
$R^{4a}$ and $R^{4b}$ are each independently selected from the group consisting of hydrogen, halogen, cyano, hydroxy, oxo, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_1$-C$_6$)alkoxy(C$_1$-C$_6$)alkyl, optionally substituted (C$_3$-C$_8$)cycloalkyl, optionally substituted phenyl, —N(R$^4$)(R$^5$), —N(R$^4$) (C=(O)R$^5$), —C(=O)N(R$^4$)(R$^5$), —O—C(=O)N (R$^4$)(R$^5$), —C(=O)—R$^4$, and —C(=O)—OR$^4$; or R$^{4a}$ and R$^{4b}$ together with the carbon atom to which they are attached form a (C$_3$-C$_8$)cycloalkyl, wherein the (C$_3$-C$_8$)cycloalkyl is optionally substituted with one to three R$^8$;
$R^{5a}$ and $R^{5b}$, at each occurrence, are independently selected from the group consisting of hydrogen, halogen, cyano, hydroxy, oxo, —SF$_5$, nitro, optionally substituted (C$_1$-C$_6$)alkyl, optionally substituted (C$_2$-C$_6$) alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_1$-C$_6$)alkoxy (C$_1$-C$_6$)alkyl, optionally substituted (C$_3$-C$_8$)cycloalkyl, optionally substituted phenyl, —N(R$^4$)(R$^5$), (R$^4$)(C=(O)R$^5$), —C(=O)N(R$^4$)(R$^5$), —O—C(=O)N(R$^4$) (R$^5$), —C(=O)—R$^4$, and —C(=O)—OR$^4$; or R$^{5a}$ and R$^{5b}$ together with the carbon atom to which they are attached form a (C$_3$-C$_8$)cycloalkyl, wherein said (C$_3$-C$_8$)cycloalkyl is optionally substituted with one to three R$^8$;
$R^6$ and $R^7$ are each independently selected from the group consisting of hydrogen, halogen, cyano, —SF$_5$, nitro, optionally substituted (C$_1$-C$_6$)alkyl, optionally substituted (C$_2$-C$_6$)alkenyl, optionally substituted (C$_2$-C$_6$) alkynyl, optionally substituted thio(C$_1$-C$_6$)alkyl, optionally substituted (C$_1$-C$_6$)alkoxy, optionally substituted (C$_1$-C$_6$)alkoxy(C$_1$-C$_6$)alkyl, optionally substituted (C$_3$-C$_8$)cycloalkyl, optionally substituted phenyl, —N(R$^4$)(R$^5$), —N(R$^4$)(C=(O)R$^5$), —C(=O)N(R$^4$) (R$^5$), —O—C(=O)N(R$^4$)(R$^5$), —C(=O)—R$^4$, —C(=O)—OR$^4$, and —OR$^9$; provided that R$^6$ and R$^7$ cannot both be hydroxy;
$R^8$, at each occurrence, is independently selected from the group consisting of cyano, halogen, hydroxy, —SF$_5$, nitro, optionally substituted (C$_1$-C$_6$)alkyl, optionally substituted (C$_1$-C$_6$)alkoxy, and optionally substituted (C$_1$-C$_6$)alkoxy(C$_1$-C$_6$)alkyl;
$R^9$ is selected from the group consisting of hydrogen and optionally substituted (C$_1$-C$_6$)alkyl;
y is an integer selected from 1, 2, 3 or 4;
ring B is optionally substituted with one to three R$^{10}$, wherein each R$^{10}$ is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted thio(C$_1$-C$_6$)alkyl, optionally substituted (C$_1$-C$_6$)alkoxy, optionally substituted (C$_3$-C$_8$)cycloalkyl, —N(R$^4$)(R$^5$), —N(R$^4$)(C=(O)R$^5$), —C(=O)N(R$^4$)(R$^5$), —O—C(=O)N(R$^4$) (R$^5$), —C(=O)—R$^4$, and —C(=O)—OR$^4$; or two R$^{10}$ substituents taken together with the carbon atom(s) to which they are attached form an optionally substituted (C$_3$-C$_8$)cycloalkyl;

ring D is optionally substituted with one to four $R^{11}$, wherein each $R^{11}$ is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, optionally substituted (4- to 6-membered)heterocycloalkyl; —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, —$C(=O)$—$OR^4$; and $R^4$ and $R^5$, at each occurrence, are each independently selected from hydrogen or optionally substituted ($C_1$-$C_6$)alkyl;

provided that the compound is not 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione, or a pharmaceutically acceptable salt of said compound.

2. The compound according to claim 1, or a pharmaceutically acceptable salt thereof, wherein X is represented by:
   i) a (5- to 6-membered)heteroaryl containing 1-3 heteroatoms;
   ii) a (6-membered)heteroaryl containing 1-3 heteroatoms; or
   iii) a (5-membered)heteroaryl containing 1-3 heteroatoms.

3. The compound according to claim 2, or a pharmaceutically acceptable salt thereof, wherein X is a (5-membered)heteroaryl selected from the group consisting of triazolyl, imidazolyl, furanyl, thiophenyl, pyrazolyl, isothiazolyl, thiazolyl, isoxazolyl, and oxazolyl.

4. The compound according to claim 3, or a pharmaceutically acceptable salt thereof, wherein X is imidazolyl.

5. The compound according to claim 3, or a pharmaceutically acceptable salt thereof, wherein X is triazolyl.

6. The compound according to claim 3, or a pharmaceutically acceptable salt thereof, wherein:

$R^1$ is selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, and —$C(=O)$—$OR^4$;

$R^{2a}$ and $R^{2b}$ at each occurrence, are independently selected from the group consisting of hydrogen, halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, and —$C(=O)$—$OR^4$;

$R^{4a}$ and $R^{4b}$ are each independently selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, and —$C(=O)$—$OR^4$;

$R^{5a}$ and $R^{5b}$, at each occurrence, are independently selected from the group consisting of hydrogen, halogen, cyano, hydroxy, oxo, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, and —$C(=O)$—$OR^4$;

$R^6$ and $R^7$ are each independently selected from the group consisting of hydrogen, halogen, cyano, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_1$-$C_6$)alkoxy($C_1$-$C_6$)alkyl, optionally substituted ($C_3$-$C_8$)cycloalkyl, optionally substituted phenyl, —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, —$C(=O)$—$OR^4$, and —$OR^9$; provided that $R^6$ and $R^7$ cannot both be hydroxy;

$R^9$ is selected from the group consisting of hydrogen and optionally substituted ($C_1$-$C_6$)alkyl;

y is an integer selected from 1, 2, 3 or 4;

ring B is optionally substituted with one to three $R^{10}$, wherein each $R^{10}$ is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, —$C(=O)$—$OR^4$;

ring D is optionally substituted with one to four $R^{11}$, wherein each $R^{11}$ is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted thio($C_1$-$C_6$)alkyl, optionally substituted ($C_1$-$C_6$)alkoxy, optionally substituted ($C_3$-$C_8$)cycloalkyl, optionally substituted (4- to 6-membered)heterocycloalkyl; —$N(R^4)(R^5)$, —$N(R^4)(C(=O)R^5)$, —$C(=O)N(R^4)(R^5)$, —O—$C(=O)N(R^4)(R^5)$, —$C(=O)$—$R^4$, —$C(=O)$—$OR^4$; and $R^4$ and $R^5$, at each occurrence, are each independently selected from hydrogen or optionally substituted ($C_1$-$C_6$)alkyl.

7. The compound according to claim 3, or a pharmaceutically acceptable salt thereof, wherein:

$R^1$ is selected from the group consisting of hydrogen, halogen, cyano, hydroxy, optionally substituted ($C_1$-$C_6$)alkyl, and optionally substituted ($C_1$-$C_6$)alkoxy; wherein the ($C_1$-$C_6$)alkyl and ($C_1$-$C_6$)alkoxy are optionally substituted with one to three substituents selected from halogen, oxo, cyano, hydroxy, or —$SF_5$;

$R^{2a}$ and $R^{2b}$ are each independently selected from hydrogen, halogen, cyano, hydroxy or optionally substituted ($C_1$-$C_6$)alkyl;

$R^{4a}$, $R^{4b}$, $R^{5a}$ and $R^{5b}$ are each independently selected from the group consisting of hydrogen, halogen, cyano, hydroxy, oxo, —$SF_5$, optionally substituted ($C_1$-$C_6$)alkyl, and optionally substituted ($C_1$-$C_6$)alkoxy, wherein the $(C_1-C_6)$alkyl and $(C_1-C_6)$alkoxy are optionally substituted with one to three substituents selected from halogen, oxo, cyano, hydroxy, or —$SF_5$;

$R^6$ and $R^7$ are each independently selected from the group consisting of hydrogen, cyano, halogen, —$SF_5$, optionally substituted $(C_1-C_6)$alkyl, and optionally substituted $(C_1-C_6)$alkoxy, wherein the $(C_1-C_6)$alkyl and $(C_1-C_6)$alkoxy are optionally substituted with one to three substituents selected from halogen, oxo, cyano, hydroxy, or —$SF_5$;

y is 1, ring B is optionally substituted with one to two $R^{10}$, wherein each $R^{10}$ is independently selected from halogen, cyano, hydroxy, —$SF_5$, optionally substituted $(C_1-C_6)$alkyl, and optionally substituted $(C_1-C_6)$alkoxy, wherein the $(C_1-C_6)$alkyl and $(C_1-C_6)$alkoxy are optionally substituted with one to three substituents selected from halogen, oxo, cyano, hydroxy, or —$SF_5$; and ring D is optionally substituted with one to three $R^{11}$, wherein each $R^{11}$ is independently selected from the group consisting of halogen, cyano, hydroxy, optionally substituted $(C_1-C_6)$alkyl, optionally substituted $(C_1-C_6)$alkoxy, —$SF_5$, —$N(R^4)(R^5)$, nitro, and optionally substituted $(C_3-C_8)$cycloalkyl, wherein the $(C_1-C_6)$alkyl, $(C_1-C_6)$alkoxy, and $(C_3-C_8)$cycloalkyl are optionally substituted with one to three substituents independently selected from halogen, cyano, hydroxy, —$SF_5$, and optionally substituted $(C_1-C_6)$alkyl, wherein $R^4$ and $R^5$ are each independently selected from hydrogen or optionally substituted $(C_1-C_6)$alkyl.

8. The compound according to claim 7, or a pharmaceutically acceptable salt thereof, wherein:

$R^1$ is an optionally substituted $(C_1-C_6)$alkyl, wherein the $(C_1-C_6)$alkyl is substituted with one to three substituents selected from halogen, oxo, cyano, hydroxy, or —$SF_5$; and $R^{2a}$, $R^{2b}$, $R^{4a}$, $R^{4b}$, $R^{5a}$ and $R^{5b}$ are each independently i) hydrogen; or ii) optionally substituted $(C_1-C_6)$alkyl, wherein the $(C_1-C_6)$alkyl is substituted with one to three substituents selected from halogen, oxo, cyano, hydroxy, or —$SF_5$.

9. The compound according to claim 8, or a pharmaceutically acceptable salt thereof, wherein $R^1$ is methyl; and $R^{2a}$, $R^{2b}$, $R^{4a}$, $R^{4b}$, $R^{5a}$ and $R^{5b}$ are each independently hydrogen.

10. The compound according to claim 8, or a pharmaceutically acceptable salt thereof, wherein $R^1$ is methyl; $R^{2a}$, $R^{2b}$, $R^{5a}$ and $R^{5b}$ are each independently hydrogen; and one of $R^{4a}$ and $R^{4b}$ is hydrogen and the other is methyl.

11. The compound according to claim 8, or a pharmaceutically acceptable salt thereof, wherein $R^1$ is methyl; one of $R^{2a}$ and $R^{2b}$ is hydrogen and the other is methyl; $R^{4a}$, $R^{4b}$, $R^{5a}$ and $R^{5b}$ are each independently hydrogen.

12. A compound having the structure of Formula II:

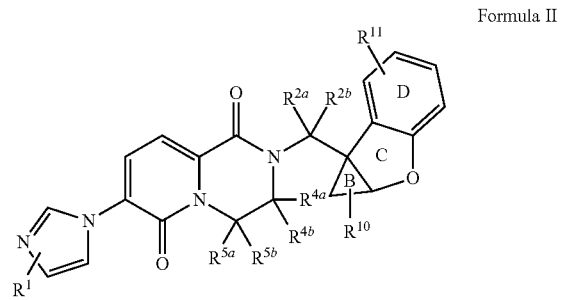

Formula II or a pharmaceutically acceptable salt thereof, wherein:

$R^1$ is selected from the group consisting of hydrogen, halogen, cyano, hydroxy, optionally substituted $(C_1-C_6)$alkyl, and optionally substituted $(C_1-C_6)$alkoxy; wherein the $(C_1-C_6)$alkyl and $(C_1-C_6)$alkoxy are optionally substituted with one to three substituents selected from halogen, oxo, cyano, hydroxy, or —$SF_5$;

$R^{2a}$, $R^{2b}$, $R^{4a}$, $R^{4b}$, $R^{5a}$ and $R^{5b}$ are each independently selected from hydrogen, halogen, cyano, hydroxy or optionally substituted $(C_1-C_6)$alkyl;

ring B is optionally substituted with one to two $R^{10}$, wherein each $R^{10}$ is independently selected from halogen or optionally substituted $(C_1-C_6)$alkyl; and ring D is optionally substituted with one to three $R^{11}$, wherein each $R^{11}$ is independently selected from halogen, optionally substituted $(C_1-C_6)$alkyl, and optionally substituted $(C_1-C_6)$alkoxy;

provided that the compound is not 7-(4-methyl-1H-imidazol-1-yl)-2-{[5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione, or a pharmaceutically acceptable salt of said compound.

13. The compound according to claim 12, wherein:

$R^1$ is selected from the group consisting of hydrogen, halogen, cyano, hydroxy, $(C_1-C_6)$alkyl, and $(C_1-C_6)$alkoxy; wherein the $(C_1-C_6)$alkyl and $(C_1-C_6)$alkoxy are optionally substituted with one to three fluoro atoms;

$R^{2a}$, $R^{2b}$, $R^{4a}$, $R^{4b}$, $R^{5a}$ and $R^{5b}$ are each independently selected from hydrogen or $(C_1-C_6)$alkyl, wherein the $(C_1-C_6)$alkyl is methyl;

ring B is optionally substituted with one to two $R^{10}$, wherein each $R^{10}$ is selected from:

i) halogen selected from fluoro or chloro, or ii) $(C_1-C_6)$alkyl, wherein the $(C_1-C_6)$alkyl is methyl; and ring D is optionally substituted with one to three $R^{11}$, wherein each $R^{11}$ is selected from:

i) halogen selected from fluoro or chloro;

ii) optionally substituted $(C_1-C_6)$alkyl selected from the group consisting of fluoromethyl, difluoromethyl, and trifluoromethyl; and iii) optionally substituted $(C_1-C_6)$alkoxy, wherein the optionally substituted $(C_1-C_6)$alkoxy is selected from the group consisting of fluoromethoxy, difluoromethoxy, trifluoromethoxy.

14. The compound according to claim 12, wherein $R^1$ is a $(C_1-C_6)$alkyl wherein the alkyl is methyl.

15. A compound having the structure of Formula III:

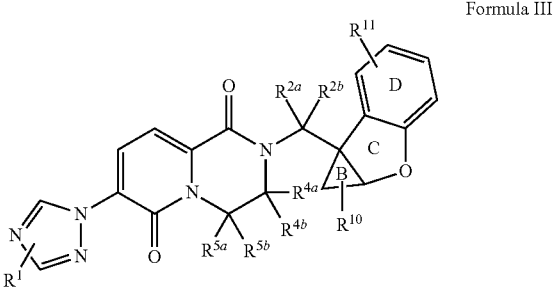

Formula III or a pharmaceutically acceptable salt thereof, wherein:
$R^1$ is selected from the group consisting of hydrogen, halogen, cyano, hydroxy, optionally substituted ($C_1$-$C_6$)alkyl, and optionally substituted ($C_1$-$C_6$)alkoxy; wherein the ($C_1$-$C_6$)alkyl and ($C_1$-$C_6$)alkoxy are optionally substituted with one to three substituents selected from halogen, oxo, cyano, hydroxy, or —$SF_5$;
$R^{2a}$, $R^{2b}$, $R^{4a}$, $R^{4b}$, $R^{5a}$ and $R^{5b}$ are each independently selected from hydrogen, halogen, cyano, hydroxy or optionally substituted ($C_1$-$C_6$)alkyl;
 ring B is optionally substituted with one to two $R^{10}$, wherein each $R^{10}$ is independently selected from halogen or optionally substituted ($C_1$-$C_6$)alkyl; and
 ring D is optionally substituted with one to three $R^{11}$, wherein each $R^{11}$ is independently selected from halogen, optionally substituted ($C_1$-$C_6$)alkyl, and optionally substituted ($C_1$-$C_6$)alkoxy.

16. The compound according to claim 15, wherein:
$R^1$ is selected from the group consisting of hydrogen, halogen, cyano, hydroxy, ($C_1$-$C_6$)alkyl, and ($C_1$-$C_6$)alkoxy; wherein the ($C_1$-$C_6$)alkyl and ($C_1$-$C_6$)alkoxy are optionally substituted with one to three fluoro atoms;
$R^{2a}$, $R^{2b}$, $R^{4a}$, $R^{4b}$, $R^{5a}$ and $R^{5b}$ are each independently selected from hydrogen or ($C_1$-$C_6$)alkyl, wherein the ($C_1$-$C_6$)alkyl is methyl;
 ring B is optionally substituted with one to two $R^{10}$, wherein each $R^{10}$ is selected from:
  i) halogen selected from fluoro or chloro, or
  ii) ($C_1$-$C_6$)alkyl, wherein the ($C_1$-$C_6$)alkyl is methyl; and
 ring D is optionally substituted with one to three $R^{11}$, wherein each $R^{11}$ is selected from:
  i) halogen selected from fluoro or chloro;
  ii) optionally substituted ($C_1$-$C_6$)alkyl selected from the group consisting of fluoromethyl, difluoromethyl, and trifluoromethyl; and
  iii) optionally substituted ($C_1$-$C_6$)alkoxy, wherein the optionally substituted ($C_1$-$C_6$)alkoxy is selected from the group consisting of fluoromethoxy, difluoromethoxy, and trifluoromethoxy.

17. A compound selected from the group consisting of:
7-(4-methyl-1H-imidazol-1-yl)-2-{[1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione;
7-(4-methyl-1H-imidazol-1-yl)-2-{[(1aS,6bS)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione;
7-(4-methyl-1H-imidazol-1-yl)-2-{[(1aR,6bR)-1a-methyl-5-(trifluoromethoxy)-1,1a-dihydro-6bH-cyclopropa[b][1]benzofuran-6b-yl]methyl}-3,4-dihydro-2H-pyrido[1,2-a]pyrazine-1,6-dione;
2-{[3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aS,6bS)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aR,6bR)-3-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aS,6bS)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aR,6bR)-4-fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione;
2-{[(1aS,6bS)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione;
2-{[(1aR,6bR)-4-fluoro-1a-methyl-5-(trifluoromethoxy)-1,1a-dihydro-6bH-cyclopropa[b][1]benzofuran-6b-yl]methyl}-7-(3-methyl-1H-1,2,4-triazol-1-yl)-3,4-dihydro-2H-pyrido[1,2-a]pyrazine-1,6-dione;
2-{[(1aS,6bS)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aR,6bR)-4-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aS,6bS)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aR,6bR)-5-(difluoromethoxy)-4-fluoro-1a-methyl-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;
2-{[(1aS,6bS)-4-fluoro-1a-methyl-5-(trifluoromethoxy)-1,1a-dihydro-6bH-cyclopropa[b][1]benzofuran-6b-yl]methyl}-7-[4-(hydroxymethyl)-1H-imidazol-1-yl]-3,4-dihydro-2H-pyrido[1,2-a]pyrazine-1,6-dione;
7-(4-methyl-1H-imidazol-1-yl)-2-{[(1aS,6bS)-1a-methyl-5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione;
7-(4-methyl-1H-imidazol-1-yl)-2-{[(1aR,6bR)-1a-methyl-5-(trifluoromethyl)-1,1a-dihydro-6bH-cyclopropa[b][1]benzofuran-6b-yl]methyl}-3,4-dihydro-2H-pyrido[1,2-a]pyrazine-1,6-dione;

2-{[(1aS,6bS)-4-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-4-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-3-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-3-fluoro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aS,6bS)-3-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione;

2-{[(1aR,6bR)-3-chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione; or a pharmaceutically acceptable salt thereof.

18. 2-{[(1aS,6bS)-4-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione, or a pharmaceutically acceptable salt thereof.

19. 2-{[(1aR,6bR)-4-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione, or a pharmaceutically acceptable salt thereof.

20. 2-{[(1aS,6bS)-3-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione, or a pharmaceutically acceptable salt thereof.

21. 2-{[(1aR,6bR)-3-Fluoro-1a-methyl-5-(trifluoromethoxy)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione, or a pharmaceutically acceptable salt thereof.

22. 2-{[(1aS,6bS)-4-Chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione, or a pharmaceutically acceptable salt thereof.

23. 2-{[(1aR,6bR)-4-Chloro-1a-methyl-5-(trifluoromethyl)-1,1a-dihydro-6bH-cyclopropa[b][1]benzofuran-6b-yl]methyl}-7-(4-methyl-1H-imidazol-1-yl)-3,4-dihydro-2H-pyrido[1,2-a]pyrazine-1,6-dione, or a pharmaceutically acceptable salt thereof.

24. 2-(((1aS,6bS)-4-fluoro-1a-methyl-5-(trifluoromethyl)-1,1a-dihydro-6bH-cyclopropa[b]benzofuran-6b-yl)methyl)-7-(4-methyl-1H-imidazol-1-yl)-3,4-dihydro-2H-pyrido[1,2-a]pyrazine-1,6-dione, or a pharmaceutically acceptable salt thereof.

25. 2-(((1aR,6bR)-4-fluoro-1a-methyl-5-(trifluoromethyl)-1,1a-dihydro-6bH-cyclopropa[b]benzofuran-6b-yl)methyl)-7-(4-methyl-1H-imidazol-1-yl)-3,4-dihydro-2H-pyrido[1,2-a]pyrazine-1,6-dione, or a pharmaceutically acceptable salt thereof.

26. 2-(((1aS,6bS)-3-fluoro-1a-methyl-5-(trifluoromethyl)-1,1a-dihydro-6bH-cyclopropa[b]benzofuran-6b-yl)methyl)-7-(4-methyl-1H-imidazol-1-yl)-3,4-dihydro-2H-pyrido[1,2-a]pyrazine-1,6-dione, or a pharmaceutically acceptable salt thereof.

27. 2-(((1aR,6bR)-3-fluoro-1a-methyl-5-(trifluoromethyl)-1,1a-dihydro-6bH-cyclopropa[b]benzofuran-6b-yl)methyl)-7-(4-methyl-1H-imidazol-1-yl)-3,4-dihydro-2H-pyrido[1,2-a]pyrazine-1,6-dione, or a pharmaceutically acceptable salt thereof.

28. A method for reducing the production of amyloid beta (Aβ) peptides, in a subject in need thereof, the method comprising administering to said subject a therapeutically effective amount of a compound according to claim 1, or a pharmaceutically acceptable salt thereof.

29. A method for reducing the production of amyloid beta Aβ42 peptide, in a subject in need thereof, the method comprising administering to said subject a therapeutically effective amount of a compound according to claim 1, or a pharmaceutically acceptable salt thereof.

30. A method for treating Alzheimer's disease in a subject in need thereof, the method comprising administering to a subject a therapeutically effective amount of a compound according to claim 1, or a pharmaceutically acceptable salt thereof.

31. A pharmaceutical composition comprising a compound of claim 1, or a pharmaceutically acceptable salt thereof, and a pharmaceutically acceptable excipient.

32. A method for reducing the production of amyloid beta Aβ42 peptide, in a subject in need thereof, the method comprising administering to said subject a therapeutically effective amount of a compound according to claim 18, or a pharmaceutically acceptable salt thereof.

33. A method for reducing the production of amyloid beta Aβ42 peptide, in a subject in need thereof, the method comprising administering to said subject a therapeutically effective amount of a compound according to claim 19, or a pharmaceutically acceptable salt thereof.

34. A method for reducing the production of amyloid beta Aβ42 peptide, in a subject in need thereof, the method comprising administering to said subject a therapeutically effective amount of a compound according to claim 20, or a pharmaceutically acceptable salt thereof.

35. A method for reducing the production of amyloid beta Aβ42 peptide, in a subject in need thereof, the method comprising administering to said subject a therapeutically effective amount of a compound according to claim 21, or a pharmaceutically acceptable salt thereof.

36. A method for reducing the production of amyloid beta Aβ42 peptide, in a subject in need thereof, the method comprising administering to said subject a therapeutically effective amount of a compound according to claim 22, or a pharmaceutically acceptable salt thereof.

37. A method for reducing the production of amyloid beta Aβ42 peptide, in a subject in need thereof, the method comprising administering to said subject a therapeutically effective amount of a compound according to claim 23, or a pharmaceutically acceptable salt thereof.

38. A method for reducing the production of amyloid beta Aβ42 peptide, in a subject in need thereof, the method comprising administering to said subject a therapeutically effective amount of a compound according to claim 24, or a pharmaceutically acceptable salt thereof.

39. A method for reducing the production of amyloid beta Aβ42 peptide, in a subject in need thereof, the method comprising administering to said subject a therapeutically effective amount of a compound according to claim 25, or a pharmaceutically acceptable salt thereof.

40. A method for reducing the production of amyloid beta Aβ42 peptide, in a subject in need thereof, the method comprising administering to said subject a therapeutically effective amount of a compound according to claim 26, or a pharmaceutically acceptable salt thereof.

41. A method for reducing the production of amyloid beta Aβ42 peptide, in a subject in need thereof, the method comprising administering to said subject a therapeutically effective amount of a compound according to claim 27, or a pharmaceutically acceptable salt thereof.

42. A method for treating Alzheimer's disease in a subject in need thereof, the method comprising administering to a subject a therapeutically effective amount of a compound according to claim 18, or a pharmaceutically acceptable salt thereof.

43. A method for treating Alzheimer's disease in a subject in need thereof, the method comprising administering to a subject a therapeutically effective amount of a compound according to claim 19, or a pharmaceutically acceptable salt thereof.

44. A method for treating Alzheimer's disease in a subject in need thereof, the method comprising administering to a subject a therapeutically effective amount of a compound according to claim 20, or a pharmaceutically acceptable salt thereof.

45. A method for treating Alzheimer's disease in a subject in need thereof, the method comprising administering to a subject a therapeutically effective amount of a compound according to claim 21, or a pharmaceutically acceptable salt thereof.

46. A method for treating Alzheimer's disease in a subject in need thereof, the method comprising administering to a subject a therapeutically effective amount of a compound according to claim 22, or a pharmaceutically acceptable salt thereof.

47. A method for treating Alzheimer's disease in a subject in need thereof, the method comprising administering to a subject a therapeutically effective amount of a compound according to claim 23, or a pharmaceutically acceptable salt thereof.

48. A method for treating Alzheimer's disease in a subject in need thereof, the method comprising administering to a subject a therapeutically effective amount of a compound according to claim 24, or a pharmaceutically acceptable salt thereof.

49. A method for treating Alzheimer's disease in a subject in need thereof, the method comprising administering to a subject a therapeutically effective amount of a compound according to claim 25, or a pharmaceutically acceptable salt thereof.

50. A method for treating Alzheimer's disease in a subject in need thereof, the method comprising administering to a subject a therapeutically effective amount of a compound according to claim 26, or a pharmaceutically acceptable salt thereof.

51. A method for treating Alzheimer's disease in a subject in need thereof, the method comprising administering to a subject a therapeutically effective amount of a compound according to claim 27, or a pharmaceutically acceptable salt thereof.

52. A method for treating Alzheimer's disease in a subject in need thereof, the method comprising administering to a subject a therapeutically effective amount of a compound according to claim 12, or a pharmaceutically acceptable salt thereof.

53. A method for reducing the production of amyloid beta Aβ42 peptide, in a subject in need thereof, the method comprising administering to said subject a therapeutically effective amount of a compound according to claim 12, or a pharmaceutically acceptable salt thereof.

\* \* \* \* \*